(12) United States Patent
Hartmann et al.

(10) Patent No.: US 9,394,290 B2
(45) Date of Patent: Jul. 19, 2016

(54) SELECTIVE CYP11B1 INHIBITORS FOR THE TREATMENT OF CORTISOL DEPENDENT DISEASES

(75) Inventors: Rolf Hartmann, Saarbruecken (DE); Ulrike Hille, Loerrach (DE); Christina Zimmer, Voelklingen (DE); Carsten A. Vock, Friedland (DE); Qingzhong Hu, Saarbruecken (DE)

(73) Assignee: UNIVERSITAET DES SAARLANDES CAMPUS SAARBRUECKEN, Saarbruecken (DE)

( * ) Notice: Subject to any disclaimer, the term of this patent is extended or adjusted under 35 U.S.C. 154(b) by 0 days.

(21) Appl. No.: 13/880,701

(22) PCT Filed: Oct. 21, 2011

(86) PCT No.: PCT/EP2011/068418
§ 371 (c)(1),
(2), (4) Date: Oct. 14, 2013

(87) PCT Pub. No.: WO2012/052540
PCT Pub. Date: Apr. 26, 2012

(65) Prior Publication Data
US 2014/0155407 A1 Jun. 5, 2014

(30) Foreign Application Priority Data
Oct. 21, 2010 (EP) ..................................... 10188380
Oct. 27, 2010 (EP) ..................................... 10188975

(51) Int. Cl.
| | | |
|---|---|---|
| C07D 409/14 | (2006.01) | |
| C07D 405/14 | (2006.01) | |
| C07D 401/06 | (2006.01) | |
| C07D 213/06 | (2006.01) | |
| C07D 403/06 | (2006.01) | |
| C07D 239/26 | (2006.01) | |
| C07D 405/04 | (2006.01) | |
| C07D 413/06 | (2006.01) | |
| C07D 417/06 | (2006.01) | |

(52) U.S. Cl.
CPC ............ *C07D 409/14* (2013.01); *C07D 213/06* (2013.01); *C07D 239/26* (2013.01); *C07D 401/06* (2013.01); *C07D 403/06* (2013.01); *C07D 405/04* (2013.01); *C07D 405/14* (2013.01); *C07D 413/06* (2013.01); *C07D 417/06* (2013.01)

(58) Field of Classification Search
None
See application file for complete search history.

(56) References Cited

U.S. PATENT DOCUMENTS 4,284,641 A * 8/1981 Thorogood ................... 514/396
4,591,377 A * 5/1986 Leone-Bay ............ A01N 43/50
504/253
8,232,289 B2 * 7/2012 Benito Collado et al. .... 514/279

FOREIGN PATENT DOCUMENTS

| EP | 2095819 A1 | 9/2009 |
|---|---|---|
| WO | 02/060877 A1 | 8/2002 |
| WO | 2007/139992 A2 | 12/2007 |

OTHER PUBLICATIONS

Ferretti et al., 13(4) Bioorg. & Med. Chem. Letts. 733-735 (2003).*
Ehmer, P.B., et al., "Development of a test system for inhibitors of human aldosterone synthase (CYP11B2): screening in fission yeast and evaluation of selectivity in V79 cells", Journal of Steroid Biochemistry and Molecular Biology, 81 (2002) p. 173-179.
Hille, U.E., et al., "First Selective CYP11B1 Inhibitors for the Treatment of Cortisol-Dependent Diseases", ACS Med. Chem. Lett., 2 (2011) p. 2-6.
Jagusch, C., et al., "Synthesis, biological evaluation and molecular modelling studies of methyleneimidazole substituted biaryls as inhibitors of human 17(alpha-hydroxylase-17,20-lyase (CYP17). Part 1: Heterocyclic modifications of the core structure", Bioorganic & Medicinal Chemistry, 16 (2008) p. 1992-2010.
International Application No. PCT/EP2011/068418, International Search Report and Written Opinion mailed Oct. 21, 2011, 17 pgs.
Denner et al., Cloning of CYP11B1 and CYP11B2 From Normal Human Adrenal and Their Functional Expression in COS-7 and V79 Chinese Hamster Cells, Endocr. Res., 1995, 443-448, 21 (1-2).
Ehmer et al., Development of a simple and rapid assay for the evaluation of inhibitors of human 17alpha-hydroxylase-C17,20-lyase (P450c17) by coexpression of P450cl7 with NADPH-cytochrome-P450-reductase in *Escherichia coli*, J.Steroid Biochem. Mol. Biol., 2000, 57-63, 75(1).
Ehmer et al., Development of a test system for inhibitors of human aldosterone synthase (CYP11B2): screening in fission yeast and evaluation of selectivity in V79 cells, J. Steroid Biochem. Mol. Biol., 2002, 173-179, 81(2).
Hutschenreuter et al., Synthesis of Hydroxy Derivatives of Highly Potent Non-steroidal CYP 17 Inhibitors as Potential Metabolites and Evaluation of their Activity by a Non Cellular Assay using Recombinant Human Enzyme, J. Enz. Inhib. Med. Chem., 2004, 17-32, 19(1).
Jagusch et al., Synthesis, biological evaluation and molecular modelling studies of methyleneimidazole substituted biaryls as inhibitors of human 17alpha-hydroxylase-17,20-lyase (CYP17). Part I: Heterocyclic modifications of the core structure, Bioorg. Med. Chem., 2008, 1992-2010, 16(4).
Mornet et al., Characterization of Two Genes Encoding Human Steroid 11Beta-Hydroxylase(P-45011Beta), J. Biol. Chem., 1989, 20961-20967, 264(35).

(Continued)

*Primary Examiner* — Timothy R Rozof
(74) *Attorney, Agent, or Firm* — Kagan Binder, PLLC

(57) ABSTRACT

The present invention relates to compounds which selectively inhibit CYP11B1. Preferably, the compounds of the present invention do not substantially inhibit CYP11B2. Moreover, the compounds of the present invention do not substantially inhibit CYP17 and/or CYP19, either. Amongst other applications of the compounds of the present invention, they can be used for the treatment of Cushing's syndrome or metabolic disease.

7 Claims, 1 Drawing Sheet

(56) References Cited

OTHER PUBLICATIONS

Roumen et al., Synthesis, Biological Evaluation, and Molecular Modeling of 1-Benzyl-1H-imidazoles as Selective Inhibitors of Aldosterone Synthase (CYP11B2), J. Med. Chem., 2010, 1712-1725, 53(4).

Swearingen et al. (Eds.), Contemporary Endocrinology: Diagnosis and management of Pituitary Disorders, 2008, Humana Press, Totowa, NJ (Table of Contents).

Thompson et al., Utilization of Oxygen and Reduced Nicotinamide Adenine Dinucleotide Phosphate by Human Placental Microsomes during Aromatization of Androstenedione, J. Biol. Chem., 1974, 5364-5372, 249(17).

Zolle et al., New Selective Inhibitors of Steroid 11Beta-Hydroxylation in the Adrenal Cortex. Synthesis and Structure—Activity Relationship of Potent Etomidate Analogues, J. Med. Chem., 2008, 2244-2253, 51(7).

* cited by examiner

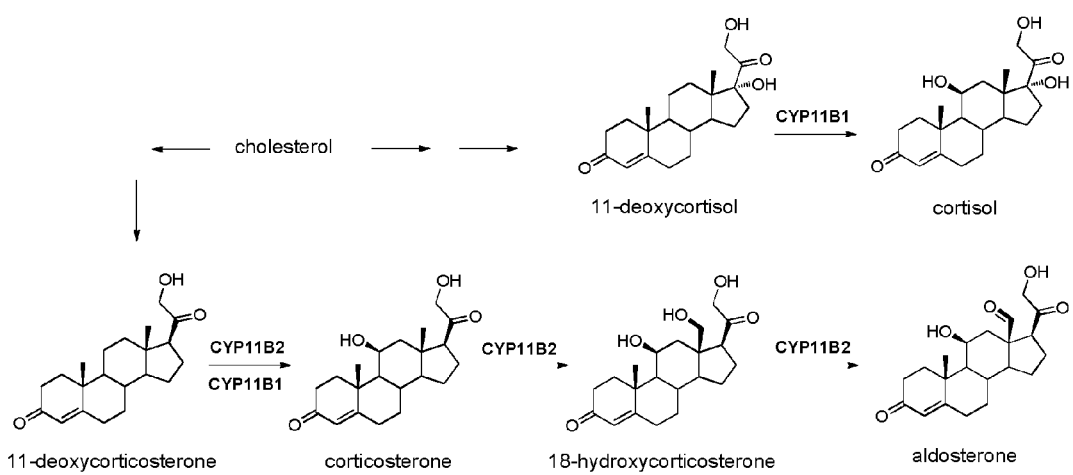

SELECTIVE CYP11B1 INHIBITORS FOR THE TREATMENT OF CORTISOL DEPENDENT DISEASES

FIELD OF THE INVENTION

The present invention relates to compounds which selectively inhibit CYP11B1. Preferably, the compounds of the present invention do not substantially inhibit CYP11B2. Moreover, the compounds of the present invention do not substantially inhibit CYP17 and/or CYP19, either. Amongst other applications of the compounds of the present invention, they can be used for the treatment of Cushing's syndrome or metabolic disease.

BACKGROUND OF THE INVENTION

Corticosteroids are a class of steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Glucocorticoids such as cortisol control carbohydrate, fat and protein metabolism and are anti-inflammatory by preventing phospholipid release, decreasing eosinophil action and a number of other mechanisms. Mineralocorticoids such as aldosterone control electrolyte and water levels, mainly by promoting sodium retention in the kidney. Some common natural hormones are corticosterone, cortisone, 17-hydroxy-11-dehydrocorticosterone and aldosterone.

Aldosterone is mainly produced in the adrenal cortex, where its biosynthesis from the precursor cholesterol involves a number of catalytic steps and enzymes. The early steps of aldosterone biosynthesis share pathways and precursors with other steroidal hormones. The final steps of aldosterone biosynthesis are conducted by the cytochrome P450 enzymes 11B1 (cortisol synthase or steroid-11μ-hydroxylase) and 11B2 (aldosterone synthase), which will further be denoted as CYP11B1 and CYP11B2, respectively. These enzymes catalyze the 11-hydroxylation of 11-deoxycorticosterone to corticosterone, which is then further hydroxylated by CYP11B2 to 18-hydroxycorticosterone (18OH—B). Finally, CYP11B2 (but not CYP11B1) oxidizes the 18-hydroxyl group of 18OH—B to the corresponding aldehyde, thus resulting in the formation of aldosterone.

CYP11B1, however, is also involved in the biosynthesis of cortisol (hydrocortisone). Specifically, it catalyzes the conversion from 11-deoxycortisol to cortisol, i.e. the key reaction in cortisol biosynthesis. Cortisol is the main glucocorticoid in humans. It regulates energy mobilization and thus the stress response. In addition, it is involved in the immune response of the human body. Abnormally increased Cortisol level is the cause of a variety of diseases including Cushing's syndrome.

Endogenous Cushing's syndrome is a hormonal disorder caused by prolonged exposure to excessive levels of circulating glucocorticoids, therefore also called hypercortisolism. Signs and symptoms of this disorder vary, but most people develop central obesity, a round face and very often also diabetes and hypertension. Cushing's syndrome is the cause of considerable morbidity and mortality. In about 80% of all cases a pituitary hypersecretion of ACTH is observed, which is mostly related to an ACTH-secreting pituitary adenoma (Cushing's disease). Benign or malignant adrenocortical tumors are the most common reasons for ACTH-independent hypercortisolism. The standard treatment for most patients is the surgical removal of the tumor or radiation therapy. However, a third of all patients are not treatable with these therapies and require temporary or permanent medication. Therefore, the application of drugs lowering the elevated cortisol levels or reducing glucocorticoid activity is considered as method of choice.

However, results with the glucocorticoid receptor antagonist mifepristone show, that administration of these agents triggers a massive secretion of cortisol which is probably caused by the hypothalamic pituitary feedback mechanism. A decrease of glucocorticoid formation should be a better therapeutic option. The best target for such an approach is steroid-11β-hydroxylase (CYP11B1), an adrenal CYP enzyme which directly affects cortisol production by catalyzing the final step in cortisol biosynthesis, namely hydroxylation of deoxycortisol in 11β-position (FIG. 1).

A major problem in the development of CYP enzyme inhibitors is the selectivity versus other CYP enzymes. Aromatase (estrogen synthase, CYP19) and 17α-hydroxylase-C17,20-lyase (CYP17) inhibitors are first line drugs for the treatment of breast cancer and upcoming therapeutics for castration refractory prostate cancer, respectively. In case of adrenal CYP11B enzymes matters are much more challenging as the homology between CYP11B1 and CYP11B2 is very high (93%) (Mornet et al. *J. Biol. Chem.* 1989, 264, 20961-20967) and for a long time it was considered impossible to obtain selective inhibitors.

Nevertheless, CYP11B1 is the key enzyme in cortisol biosynthesis and its inhibition with selective compounds is a promising strategy for the treatment of diseases associated with elevated cortisol levels like Cushing's syndrome or metabolic disease which are otherwise not appropriately treatable.

Until recently, selective inhibitors of mineralo- and glucocorticoids were not in the focus of research efforts. This was due to the fact that the sequence identity between aldosterone synthase (CYP11B2) and cortisol synthase (steroid-11μ-hydroxylase, CYP11B1) is very high (93%), and it was considered impossible to obtain selective inhibitors of one enzyme versus the other. Thus, although there is a high medical need for drugs interfering with excessive glucocorticoid formation resulting, for example, in Cushing's syndrome, there are only few inhibitors of CYP11B1 described so far. Because of their unselective action, their application is associated with severe side effects: The CYP19 inhibitor aminoglutethimide, metyrapone, the antimycotics ketoconazole and fluconazole, and the hypnotic etomidate are also inhibitors of other adrenal and gonadal Cytochrom P450 (CYP) enzymes. However, all of them show severe side effects due to the fact that they are unselective, i.e. they inhibit a broad range of CYP enzymes or hydroxysteroid dehydrogenases (HSDs). Some common side effects include gastrointestinal upset, edema, rash, malaise, gynecomastia and elevated transaminases (see Contemporary Endocrinology: Diagnosis and management of Pituitary Disordwers, Ed. By: Swearingen and Biller, Humana Press (2008), Totowa, N.J.).

Accordingly, the hypnotic and unselective CYP inhibitor etomidate was recently used as starting point in several drug discovery programs. While Roumen et al. (*J. Med. Chem.* 2010, 53, 1712-1725) discovered selective CYP11B2 inhibitors outgoing from etomidate and fadrozole, Zolle et al. (*J. Med. Chem.* 2008, 51, 2244-2253) described etomidate derived CYP11B1 inhibitors without investigating selectivity toward other CYPs. Also, WO 2007/139992 describes both CYP11B2 and CYP11B1 inhibitors based on imidazole derivatives. However, it does not provide selective CYP11B1 inhibitors.

Jagusch et al. (*Bioorg. Med. Chem.* 16 (2008) 1992-2010) discloses imidazole based molecules as substrate mimetic of CYP17 (an enzyme involved in the biosynthesis of androgen) that are useful in the treatment of prostate cancer.

PCT patent application publication number WO02/060877 discloses imidazole derivative which are NMDA (N-methyl-D-aspartate) receptor subtype 2B selective blockers which have as possible therapeutic indications acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, depression and chronic and acute pain.

SUMMARY OF THE INVENTION

Having regard to the state of the art, there is a need to provide further, alternative selective CYP11B1 inhibitors. These inhibitors can then be applied for the treatment of medical conditions characterized by an abnormal activity or abnormal expression/level of CYP11B1 in a subject. Accordingly, the technical problem of the present invention is to comply with this need.

The present invention addresses this need and thus provides as a solution to the technical problem embodiments pertaining to novel imidazole compounds described herein, shown in the formulas and Tables and exemplified in the appended Examples. These compounds are contemplated to be selective CYP11B1 inhibitors and are, for example, illustrated in formula (1), formula (2) or formula (3). Preferably, the imidazole compounds of the present invention are for use as a medicament. Preferably, for use in the treatment of a condition characterized by abnormal activity or abnormal expression/level of steroid-11β-hydroxylase (CYP11B1). Advantageously, the compounds of the present invention can be used in treating cortisol dependent disorders such as Cushing's syndrome or metabolic disease or metabolic syndrome.

Indeed, despite the challenging homology between CYP11B1 and CYP11B2 and overlapping ligand specificity, the present inventors have surprisingly discovered compounds which selectively inhibit CYP11B1.

Preferably, the compounds of the present invention have an $IC_{50}$ of less than about 200, more preferably less than about 175, more preferably less than about 150, even more preferably less than about 125, even yet more preferably less than about 115, particularly preferable less than about 105, most preferably less than about 100, 75, 50, 25 or 20 nM.

In the alternative or addition the compounds of the present invention can preferably be characterized by having a selectivity factor (SF) ($IC_{50}$ (CYP11B2)/$IC_{50}$ (CYP11B1) of greater than about 5, 10, 15, 20, 25, 30, 35, 40, 45, 46, 47, 48, 49 or 50.

Furthermore, in the alternative or addition, the compounds of the present invention can be characterized in that they selectively inhibit CYP11B1, and do not substantially inhibit CYP17 and/or CYP19. Preferably, the compounds of the present invention do not inhibit CYP17 more than 30, 25, 20, 15, 10 or 5%. Preferably, the compounds of the present invention do not inhibit CYP19 more than 30, 25, 20, 15, 10 or 5%.

Accordingly, in some preferred embodiments, the compounds of the present invention selectively inhibit CYP11B1 and do not substantially inhibit CYP17 (not more than 30, 25, 20, 15, 10 or 5%) and/or CYP19 (not more than 30, 25, 20, 15, 10 or 5%) and can be further characterized by having a selectivity factor ($IC_{50}$ (CYP11B2)/$IC_{50}$ (CYP11B1)) greater than about 5, 10, 15, 20, 25, 30, 35, 40, 45, 46, 47, 48, 49 or 50.

Accordingly, the compounds of the present invention as CYP11B1 inhibitors are also useful for the treatment of a disorder or a disease or a condition characterized by abnormal activity or abnormal level of CYP11B1. This is so because the compounds of the present invention when used as medicaments are envisaged to exhibit either reduced side effects or negligible side effects due to the fact that they are selective CYP11B1 inhibitors and hence can be used in a targeted treatment regime. For example, the compounds of the present invention can be used for the treatment of a disorder, a disease or a condition such as Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

When used herein, the term "about" is understood to mean that there can be variation in the respective values (e.g. $IC_{50}$ or the selectivity factor) that can be to 5%, 10%, 15%, 20% or up to and including 25% of the given value.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

As described herein, "preferred embodiment" means "preferred embodiment of the present invention". Likewise, as described herein, "various embodiments" and "another embodiment" means "various embodiments of the present invention" and "another embodiment of the present invention", respectively.

In one embodiment, the present invention provides a compound of formula (1):

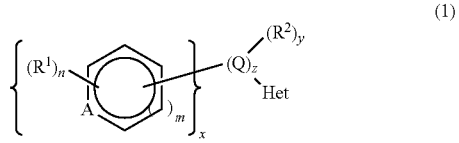

(1)

wherein,

Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^1$ or $R^2$ can be independently H, $C_1$-$C_{12}$ alkyl, haloalkyl, $C_1$-$C_5$ alkoxy, hydroxy, $C_6$-$C_{13}$ aryl, napthyl, benzo[b]thiophen, thiophen, amino, amido, $C(O)R^4$, $OC(O)R^4$, ester, ether, $SO_2R^4$, furanyl, het, halogen, trityl, CN, $NO_2$ or OAc; either of which is unsubstituted or can be independently substituted further with $R^3$ (wherein where multiple substitution with $R^3$ is possible, the substituents can be independently selected from $R^3$), $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, trityl, CN, $NO_2$ or OAc, $R^4$ is H, OH, $C_1$-$C_5$ alkoxy, alkyl or aryl, A is one or more heteroatoms independently selected from N, O, S or Se. Wherein A is N, preferably heterocycles are pyridine, pyrimidine or pyridazine; which can be further annelated by 5- or 6-membered rings.

m is selected from 0-3 carbons, preferably 1, n is 0-6,

Q is C, O, S, CH=CH, N, CO, $CO_2$, CONH, $SO_2$, $SO_2NH$,

X is 1-3,

Y is 0-2,

Z is 1-2; if z>1, multi-Q can be any linker described above, or a pharmaceutically acceptable derivative.

It is envisaged that the compounds of the present invention such as the compound of formula (1) selectively inhibit CYP11B1. Accordingly, in some preferred embodiments, said compound of formula (1) selectively inhibits CYP11B1 and has an $IC_{50}$ of less than about 200, more preferably less than about 175, more preferably less than about 150, even more preferably less than about 125, even yet more preferably less than about 115, particularly preferable less than about 105, most preferably less than about 100, 75, 50, 25 or 20 nM.

The compound of formula (1) of the present invention does preferably not substantially inhibit CYP17 and/or CYP19. Accordingly, in some preferred embodiments, the inhibition of CYP17 and/or 19 is not more than 30, 25, 20, 15 or 10 or 5%.

In a preferred embodiment for the compounds of formula (1), the compound is characterized by having a selectivity factor ($IC_{50}$ (CYP11B2)/$IC_{50}$ (CYP11B1)) greater than about 5, 10, 15, 20, 25, 30, 35, 40, 45, 46, 47, 48, 49 or 50.

In certain embodiments, provided that in said compound of formula (1), when Het is imidazolyl, Q is C, z is 1, $R^2$ is H, y is 2, m is 1, A is N and n is 1—if $R^1$ is $C_6$-$C_{13}$ aryl it cannot be phenyl (non-substituted), 2-methoxy substituted phenyl or a 3-amino substituted phenyl, 4-fluorine substituted phenyl, 3,4-methoxy substituted phenyl, 3-methoxy substituted phenyl, 3,4-fluorine substituted phenyl, 4-substituted methoxy phenyl.

In a further embodiment, the compound of formula 1 has Q=C, z=1, $R^2$=H, y=2, x=1, m=1, A=N and n=1-3, more preferably 2, most preferably 1.

In another embodiment, the present invention provides a compound of formula (2):

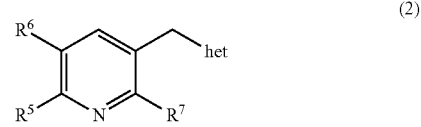

(2)

wherein, $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, CN, $NO_2$ or OAc, $R^4$ is H, OH, $C_1$-$C_5$ alkoxy, alkyl or aryl, $R^5$ is H, $C_1$-$C_{12}$ alkyl, haloalkyl, cycloalkyl, alkenyl, cycloalkylene, alkynyl, $C_6$-$C_{13}$ aryl, naphthyl, $C_1$-$C_5$ alkoxy, hydroxy, halogen, furanyl, benzo[b]thiophen, thiophen, CN, $NO_2$, OAc, amino, amido, $C(O)R^4$, $OC(O)R^4$, trityl or Het; which may be unsubstituted or substituted further with $R^3$ (wherein where multiple substitution with $R^3$ is possible, the substituents can be independently selected from $R^3$), Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazoltl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^6$ is H, $C_1$-$C_{12}$ alkyl, haloalkyl, cycloalkyl, $C_1$-$C_5$ alkoxy, hydroxy, halogen, alkenyl, cycloalkylene, alkynyl, $C_6$-$C_{13}$ aryl, naphthyl, furanyl, thiophen, benzo[b]thiophen, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), $R^7$ is H, Halogen, $C_1$-$C_{12}$ alkyl, haloalkyl, cycloalkyl, $C_2$-$C_{12}$ alkenyl, cycloalkylene, alkynyl, $C_6$-$C_{13}$ aryl, $C_1$-$C_5$ alkoxy, hydroxy, thiophen, het, furanyl, benzo[b]thiophen, naphthyl, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), or a pharmaceutically acceptable derivative.

It is envisaged that the compounds of the present invention such as the compound of formula (2) selectively inhibit CYP11B1. Accordingly, in some preferred embodiments, said compound of formula (2) selectively inhibits CYP11B1 and has an $IC_{50}$ of less than about 200, more preferably less than about 175, more preferably less than about 150, even more preferably less than about 125, even yet more preferably less than about 115, particularly preferable less than about 105, most preferably less than about 100, 75, 50, 25 or 20 nM.

The compound of formula (2) of the present invention does preferably not substantially inhibit CYP17 and/or CYP19. Accordingly, in some preferred embodiments, the inhibition of CYP17 and/or 19 is not more than 30, 25, 20, 15 or 10 or 5%.

In a preferred embodiment for the compounds of formula (2), the compound is characterized by having a selectivity factor ($IC_{50}$ (CYP11B2)/$IC_{50}$ (CYP11B1) greater than about 5, 10, 15, 20, 25, 30, 35, 40, 45, 46, 47, 48, 49 or 50.

In certain embodiments, provided that in said compound of formula (2), when $R^5$ is $C_6$-$C_{13}$ aryl it cannot be phenyl (non-substituted), 2-methoxy substituted phenyl or a 3-amino substituted phenyl, 4-fluorine substituted phenyl, 3,4-methoxy substituted phenyl, 3-methoxy substituted phenyl, 3,4-fluorine substituted phenyl, 4-substituted methoxy phenyl.

In other embodiments, provided that in said compound of formula (2), when $R^7$ is H and that one or both of $R^5$ or $R^6$ are independently either H, aryl or heteroaryl; wherein aryl or heteroaryl may be unsubstituted or substituted further with $R^3$ (wherein where multiple substitution with $R^3$ is possible, the substituents can be independently selected from $R^3$). If only one of $R^5$ or $R^6$ is independently either H, aryl or heteroaryl, the other $R^5$ or $R^6$ can be as defined herein.

In one embodiment the compounds of the present invention are the compounds of formula (2) with the exclusion of the following compounds:

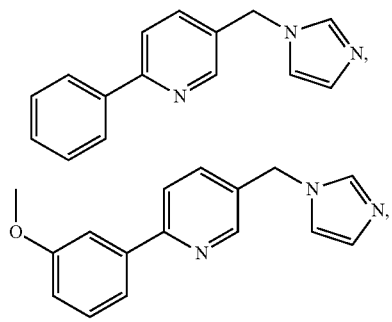

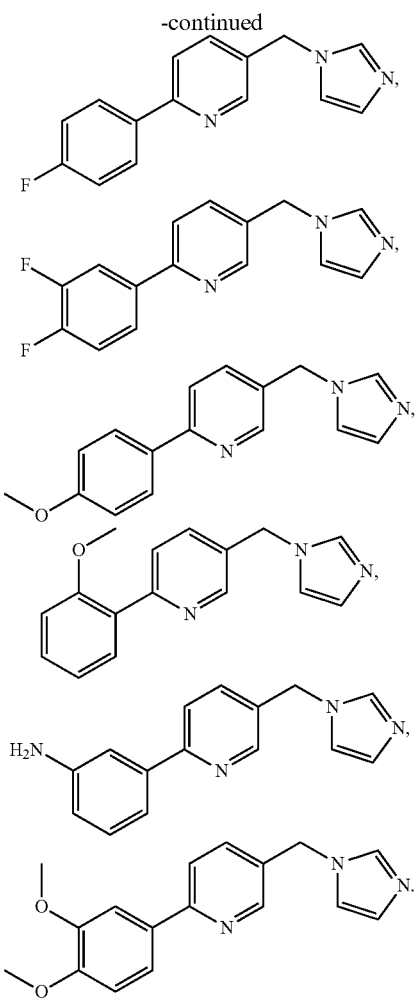

In a yet further (preferred) embodiment, the present invention provides an imidazol-1-ylmethyl-pyridine compound of formula (3):

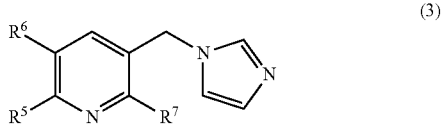

wherein, $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, CN, $NO_2$ or OAc, $R^4$ is H, OH, $C_1$-$C_5$ alkoxy, alkyl or aryl, $R^5$ is H, $C_1$-$C_{12}$ alkyl, haloalkyl, cycloalkyl, alkenyl, cycloalkylene, alkynyl, $C_6$-$C_{13}$ aryl, naphthyl, $C_1$-$C_5$ alkoxy, hydroxy, halogen, furanyl, benzo[b]thiophen, thiophen, CN, $NO_2$, OAc, amino, amido, $C(O)R^4$, $OC(O)R^4$, trityl or Het; which may be unsubstituted or substituted further with $R^3$ (wherein where multiple substitution with $R^3$ is possible, the substituents can be independently selected from $R^3$), Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^6$ is H, $C_1$-$C_{12}$ alkyl, haloalkyl, cycloalkyl, $C_1$-$C_5$ alkoxy, hydroxy, halogen, alkenyl, cycloalkylene, alkynyl, $C_6$-$C_{13}$ aryl, naphthyl, furanyl, thiophen, benzo[b]thiophen, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), $R^7$ is H, Halogen, $C_1$-$C_{12}$ alkyl, haloalkyl, cycloalkyl, $C_2$-$C_{12}$ alkenyl, cycloalkylene, alkynyl, $C_6$-$C_{13}$ aryl, $C_1$-$C_5$ alkoxy, hydroxy, thiophen, het, furanyl, benzo[b]thiophen, naphthyl, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), or a pharmaceutically acceptable derivative.

It is envisaged that the compounds of the present invention such as the compound of formula (3) selectively inhibit CYP11B1. Accordingly, in some preferred embodiments, said compound of formula (3) selectively inhibits CYP11B1 and has an $IC_{50}$ of less than about 200, more preferably less than about 175, more preferably less than about 150, even more preferably less than about 125, even yet more preferably less than about 115, particularly preferable less than about 105, most preferably less than about 100, 75, 50, 25 or 20 nM.

The compound of formula (3) of the present invention does preferably not substantially inhibit CYP17 and/or CYP19. Accordingly, in some preferred embodiments, the inhibition of CYP17 and/or 19 is not more than 30, 25, 20, 15 or 10 or 5%.

In a preferred embodiment for the compounds of formula (3), the compound is characterized by having a selectivity factor ($IC_{50}$ (CYP11B2)/$IC_{50}$ (CYP11B1) greater than about 5, 10, 15, 20, 25, 30, 35, 40, 45, 46, 47, 48, 49 or 50.

In certain embodiments, provided that in said compound of formula (3), when $R^5$ is $C_6$-$C_{13}$ aryl it cannot be phenyl (non-substituted), 2-methoxy substituted phenyl or a 3-amino substituted phenyl, 4-fluorine substituted phenyl, 3,4-methoxy substituted phenyl, 3-methoxy substituted phenyl, 3,4-fluorine substituted phenyl, 4-substituted methoxy phenyl.

In one embodiment the compounds of the present invention are the compounds of formula (3) with the exclusion of the following compounds:

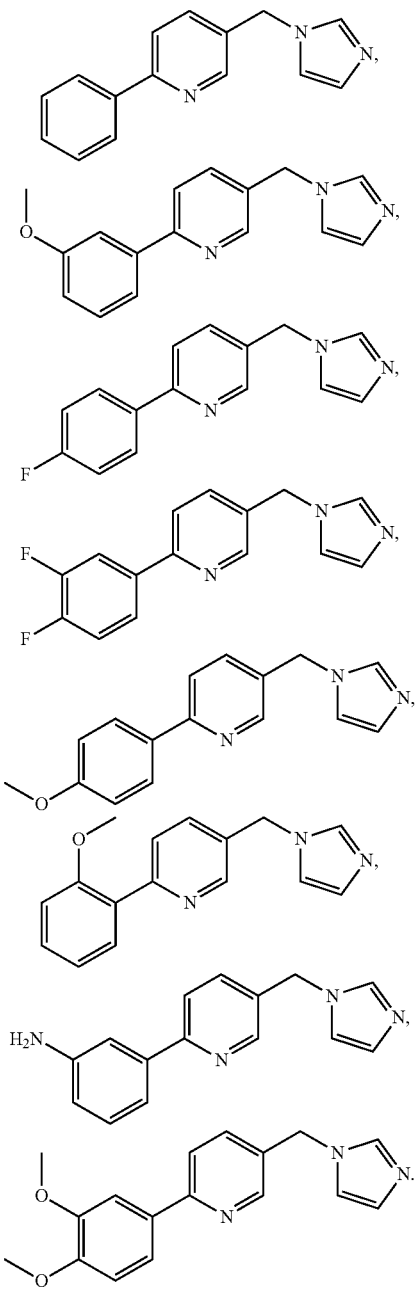

In some embodiments, said compound of formula (3) is for use in the treatment of a condition characterized by abnormal activity or abnormal expression/level of steroid-11μ-hydroxylase (CYP11B1).

In one embodiment, the selective CYP11B1 inhibitor is a compound selected from 5-Imidazol-1-ylmethyl-2-naphthalen-1-yl-pyridine, 2-Furan-3-yl-5-imidazol-1-ylmethyl-pyridine, 2,3-Di-furan-2-yl-5-imidazol-1-ylmethyl-pyridine, 2-Benzo[b]thiophen-3-yl-5-imidazol-1-ylmethyl-pyridine, 2-(2-Fluoro-phenyl)-5-imidazol-1-ylmethyl-pyridine, 5-Imidazol-1-ylmethyl-2-thiophen-3-yl-pyridine, 3-(5-Imidazol-1-ylmethyl-pyridin-2-yl)-phenylamine, 2-(5-(midazol-1-ylmethyl-pyridin-2-yl)-phenylamine, 2-Furan-2-yl-5-imidazol-1-ylmethyl-pyridine, 5-Imidazol-1-ylmethyl-2-(2-methoxy-phenyl)-pyridine, 5-(5-Imidazol-1-ylmethyl-pyridin-2-yl)-thiophene-2-carbaldehyde, 5-Imidazol-1- ylmethyl-2-thiophen-2-yl-pyridine, 3-Imidazol-1-ylmethyl-2-thiophen-2-yl-pyridine, 2-Bromo-3-imidazol-1-ylmethyl-pyridine, 2-Fluoro-4-(5-imidazol-1-ylmethyl-pyridin-2-yl)-phenol, 5-Imidazol-1-ylmethyl-2-phenyl-pyridine or 5-Imidazol-1-ylmethyl-2-naphthalen-2-yl-pyridine for use in the treatment of Cushing's syndrome or metabolic disease or metabolic syndrome.

In a most preferred embodiment for the selective CYP11B1 inhibitor of the current invention, the compound is selected from:

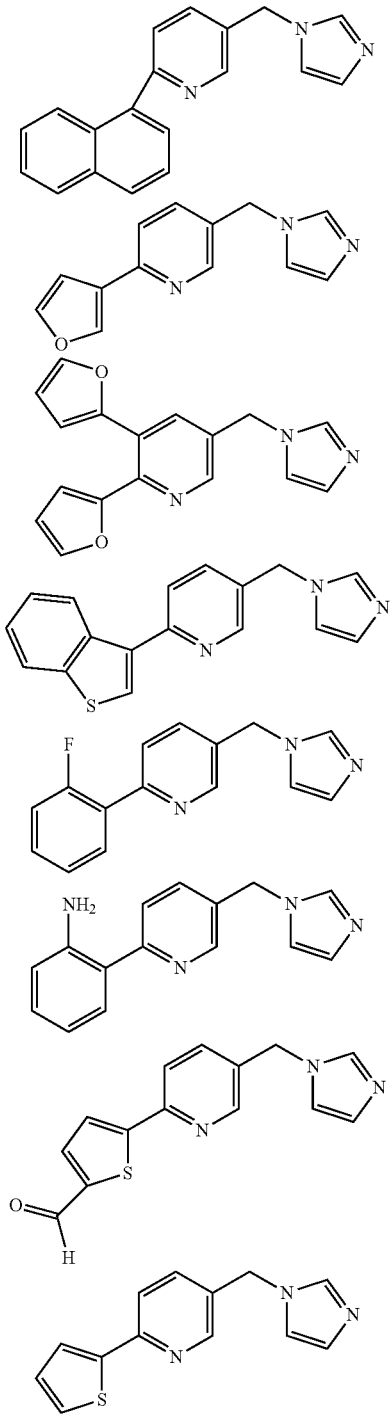

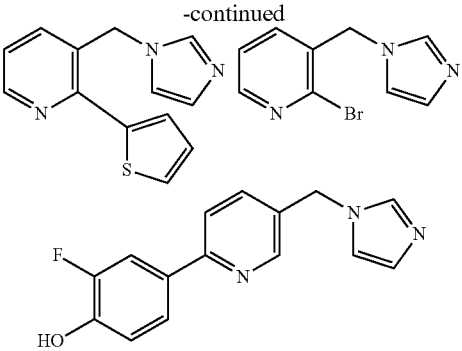

In another embodiment for the selective CYP11B1 inhibitor of the current invention, the compound is 5-Imidazol-1-ylmethyl-2-naphthalen-1-yl-pyridine, 2-Furan-3-yl-5-imidazol-1-ylmethyl-pyridine, 2,3-Di-furan-2-yl-5-imidazol-1-ylmethyl-pyridine, 2-Benzo[b]thiophen-3-yl-5-imidazol-1-ylmethyl-pyridine, 2-(2-Fluoro-phenyl)-5-imidazol-1-ylmethyl-pyridine, 2-(5-Imidazol-1-ylmethyl-pyridin-2-yl)-phenylamine, 5-(5-Imidazol-1-ylmethyl-pyridin-2-yl)-thiophene-2-carbaldehyde, 5-Imidazol-1-ylmethyl-2-thiophen-2-yl-pyridine, 3-Imidazol-1-ylmethyl-2-thiophen-2-yl-pyridine, 2-Bromo-3-imidazol-1-ylmethyl-pyridine or 2-Fluoro-4-(5-imidazol-1-ylmethyl-pyridin-2-yl)-phenol.

In some aspects of the compounds of the present invention are preferably for use as a medicament.

Similarly, a compound of the present invention is preferably present in a pharmaceutical composition comprising a therapeutically effective amount of a compound and one or more pharmaceutically acceptable carriers. In some preferred embodiments, the pharmaceutical composition comprising an additional pharmacologically active compound.

Preferably, the compounds of the present invention are for use in the treatment of a disorder characterized by an abnormal activity or abnormal expression/level of CYP11B1 in a subject Likewise, the compounds of the present invention may also be used in a method of treating a disorder characterized by an abnormal activity or abnormal expression/level of CYP11B1 in a subject, wherein the method comprises administering to the subject a therapeutically effective amount of the compound of the present invention.

Also, the compounds of the present invention are for use in treating cortisol dependent disorder. In preferred aspects, the disorder is selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after stroke and the cortisol-induced mineralocorticoid excess.

More preferably, the disorder is Cushing's syndrome or metabolic syndrome.

In other preferred embodiments, the compounds of the present invention are for use in treating weight loss.

DETAILED DESCRIPTION OF THE INVENTION

The present inventors have discovered imidazole compounds. These compounds are envisaged for use as a medicament or for use in the treatment of a condition characterized by abnormal activity or abnormal expression/level of steroid-11μ-hydroxylase (CYP11B1). The inventors have suprisingly found that amongst other things, the compounds of the present invention can be used in treating cortisol dependent disorders such as Cushing's syndrome or metabolic disease or metabolic syndrome.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder. The disease or disorder is preferably one described herein such as a cortisol dependent disorder. In preferred aspects, the disorder is selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after stroke and the cortisol-induced mineralocorticoid excess. More preferably, the disorder is Cushing's syndrome or metabolic syndrome.

Preferably, the compounds of the present invention have an $IC_{50}$ of less than about 200, more preferably less than about 175, more preferably less than about 150, even more preferably less than about 125, even yet more preferably less than about 115, particularly preferable less than about 105, most preferably less than about 100, 75, 50, 25 or 20 nM. As used herein, $IC_{50}$ refers to an amount, concentration or dosage of a particular test compound that achieves a 50% inhibition of a maximal response, in an assay that measures such response. The $IC_{50}$ values are determined in accordance with common general knowledge and means and methods. However, preferably $IC_{50}$ values are determined in accordance with the assays described in the appended Examples.

In the alternative or addition the compounds of the present invention can preferably be characterized by having a selectivity factor ($IC_{50}$ (CYP11B2)/$IC_{50}$ (CYP11B1) of greater than about 5, 10, 15, 20, 25, 30, 35, 40, 45, 46, 47, 48, 49 or 50.

Furthermore, in the alternative or addition, the compounds of the present invention can be characterized in that they do not only selectively inhibit CYP11B1, but also do not substantially inhibit CYP17 and/or CYP19. Preferably, the compounds of the present invention do not inhibit CYP17 more than 30, 25, 20, 15, 10 or 5%. Preferably, the compounds of the present invention do not inhibit CYP19 more than 30, 25, 20, 15, 10 or 5%).

Inhibition of CYP17 or CYP19, respectively, is determined in accordance with common general knowledge and means and methods. However, preferably CYP17 and/or CYP19 inhibition is determined in accordance with the assays described in the appended Examples.

Accordingly, in some particularly preferred embodiments, the compounds of the present invention selectively inhibit CYP11B1 and do not substantially inhibit CYP17 (not more than 30, 25, 20, 15, 10 or 5%) and/or CYP19 (not more than 30, 25, 20, 15, 10 or 5%) and can be further characterized by having a selectivity factor (sf, i.e., $IC_{50}$ (CYP11B2)/$IC_{50}$ (CYP11B1)) greater than about 5, 10, 15, 20, 25, 30, 35, 40, 45, 46, 47, 48, 49 or 50.

In one embodiment, the present invention provides a compound of formula (1):

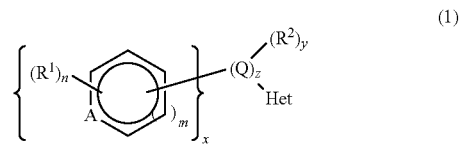

wherein,

Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^1$ or $R^2$ can be independently H, $C_1$-$C_{12}$ alkyl, haloalkyl, $C_1$-$C_5$ alkoxy, hydroxy, $C_6$-$C_{13}$ aryl, napthyl, benzo[b]thiophen, thiophen, amino, amido, $C(O)R^4$, $OC(O)R^4$, ester, ether, $SO_2R^4$, furanyl, het, halogen, trityl, CN, $NO_2$ or OAc; either of which is unsubstituted or can be independently substituted further with $R^3$ (wherein where multiple substitution with $R^3$ is possible, the substituents can be independently selected from $R^3$), $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, trityl, CN, $NO_2$ or OAc, $R^4$ is H, OH, $C_1$-$C_5$ alkoxy, alkyl or aryl, A is one or more heteroatoms independently selected from N, O, S or Se. Wherein A is N, preferably heterocycles are pyridine, pyrimidine or pyridazine; which can be further annelated by 5- or 6-membered rings.

m is selected from 0-3 carbons, preferably 1, n is 0-6,

Q is C, O, S, CH=CH, N, CO, $CO_2$, CONH, $SO_2$, $SO_2NH$,

X is 1-3,

Y is 0-2,

Z is 1-2; if z>1, multi-Q can be any linker described above, or a pharmaceutically acceptable derivative.

Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), As used herein, "heteroaryl" refers to a monocyclic or multicyclic aromatic ring system, in certain embodiments, of about 5 to about 15 members, more preferably 5 to about 12 members, more preferably still 5 to about 10 members, even more preferably 5 members, where one or more, in one embodiment 1 to 3, of the atoms in the ring system is a heteroatom, that is, an element other than carbon, including but not limited to, nitrogen, oxygen or sulfur; more preferably the heteroatom is nitrogen or sulfur, most preferably nitrogen. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, thiazolyl, isoxazolyl, triazolyl, quinolinyl, isoquinolinyl, benzo[b]imidazole or 2-benzo[b]thiophene. Furthermore, heteroaryl can be further annelated by 5- or 6-membered rings, which can also be substituted with $R^3$ (wherein where multiple substitution with $R^3$ is possible, the substituents can be independently selected from $R^3$).

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "heteroaralkyl" refers to an alkyl group in which one of the hydrogen atoms of the alkyl is replaced by a heteroaryl group.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "alkyl," "alkenyl" and "alkynyl" carbon chains, if not specified, contain from 1 to 20 carbons, or 1 or 2 to 16 carbons, or 1 or 2 to 12 carbons, especially those having from 1 to 5 or 1 to 3 carbons, and are straight or branched. Alkyl carbon chains can also be cyclic. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, adamantyl, cyclo-propyl, cyclo-pentyl, cyclo-hexyl, trityl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond. As used herein, "cycloalkyl", "cycloalkenyl" or "cycloalkynyl" can be used interchangeably in place of "alkyl" in the compounds of the present invention.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein "$C_1$-$C_5$ alkoxy" may be straight or branched, preferably OMe, OEt or O$^i$Pr, most preferably OMe.

As used herein, "aryl" refers to aromatic monocyclic or multicyclic groups containing from 6 to 19 carbon atoms, more preferably 6 to 13 carbon atoms. Aryl groups include, but are not limited to groups such as unsubstituted or substituted fluorenyl, unsubstituted or substituted phenyl and unsubstituted or substituted naphthyl. Naphthyl as used herein can be 1-naphthalene or 2-napthalene. Preferably aryl is 1-naphthalene or phenyl, most preferably 1-naphthalene. Aryl can also be further annelated by 5- or 6-membered rings, which can also be substituted with $R^3$ (wherein where multiple substitution with $R^3$ is possible, the substituents can be independently selected from $R^3$).

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "pseudohalides" or "pseudohalo" groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide. Accordingly, pseudohalides can also be used interchangeably in place of halogen in the compounds of the present invention.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.

As used herein, "carboxy" refers to a divalent radical, —C(O)O—.

As used herein, "amino" can be either unsubstituted or mono/di-substituted with alkyl and/or aryl. In certain embodiments, aryl or alkyl can be further substituted with $R^3$. Wherein multiple substitution is possible, $R^3$ can be independently selected from $R^3$ as defined herein. "Amino" is preferably —NH$_2$, —NHMe or —NMe$_2$.

As used herein "amido" refers to the divalent group —C(O)NH— which can be either unsubstituted or mono/di-substituted with alkyl and/or aryl. In certain embodiments, aryl or alkyl can be further substituted with $R^3$. Wherein multiple substitution is possible, $R^3$ can be independently selected from $R^3$ as defined herein.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein.

Where the number of any given substituent is not specified (e.g., haloalkyl), there may be one or more substituents present. For example, "haloalkyl" may include one or more of the same or different halogens.

As used herein, the abbreviations such as those for compounds, are, unless indicated otherwise, in accord with their common usage, recognized abbreviations, the IUPAC or IUPAC-IUB (Commission on Biochemical Nomenclature).

Some synthetic routes for preparing the compounds of the present invention are given below along with some possible testing methods. The following examples are intended to illustrate the invention and are not to be construed as being limitations thereon.

If not mentioned otherwise, all evaporations are performed under reduced pressure, preferably between about 15 mm Hg and 100 mm Hg (=20-133 mbar). The structure of final products, intermediates and starting materials was confirmed by standard analytical methods, e.g., microanalysis and spectroscopic characteristics, e.g., MS, IR, NMR. Abbreviations used are those conventional in the art.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound.

It is to be understood that the compounds provided herein may contain chiral centers. Such chiral centers may be of either the (R) or (S) configuration, or may be a mixture thereof.

Thus, the compounds provided herein may be enantiomerically pure, or be stereoisomeric or diastereomeric mixtures.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR$^8$) where R$^8$ is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R$^8$) where R$^8$ is hydrogen, alkyl, alkenyl, alkynyl, aryl, heteroaryl, aralkyl, heteroaralkyl, cycloalkyl or heterocyclyl.

Pharmaceutically acceptable solvates and hydrates are complexes of a compound with one or more solvent or water molecules, or 1 to about 100, or 1 to about 10, or one to about 2, 3 or 4, solvent or water molecules.

In certain embodiments, provided that in said compound of formula (1), when Het is imidazolyl, Q is C, z is 1, $R^2$ is H, y is 2, m is 1, A is N and n is 1—if $R^1$ is $C_6$-$C_{13}$ aryl it cannot be phenyl (non-substituted), 2-methoxy substituted phenyl or a 3-amino substituted phenyl, 4-fluorine substituted phenyl, 3,4-methoxy substituted phenyl, 3-methoxy substituted phenyl, 3,4-fluorine substituted phenyl, 4-substituted methoxy phenyl.

In a further embodiment, the compound of formula (1) has Q=C, z=1, $R^2$=H, y=2, x=1, m=1, A=N and n=1-3, more preferably 2, most preferably 1.

In another embodiment, the present invention provides a compound of formula (2):

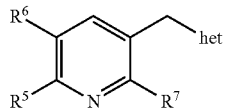

(2)

wherein, $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, CN, $NO_2$ or OAc, $R^4$ is H, OH, $C_1$-$C_5$ alkoxy, alkyl or aryl, $R^5$ is H, $C_1$-$C_{12}$ alkyl, haloalkyl, cycloalkyl, alkenyl, cycloalkylene, alkynyl, $C_6$-$C_{13}$ aryl, naphthyl, $C_1$-$C_5$ alkoxy, hydroxy, halogen, furanyl, benzo[b]thiophen, thiophen, CN, $NO_2$, OAc, amino, amido, $C(O)R^4$, $OC(O)R^4$, trityl or Het; which may be unsubstituted or substituted further with $R^3$ (wherein where multiple substitution with $R^3$ is possible, the substituents can be independently selected from $R^3$), Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^6$ is H, $C_1$-$C_{12}$ alkyl, haloalkyl, cycloalkyl, $C_1$-$C_5$ alkoxy, hydroxy, halogen, alkenyl, cycloalkylene, alkynyl, $C_6$-$C_{13}$ aryl, naphthyl, furanyl, thiophen, benzo[b]thiophen, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), $R^7$ is H, Halogen, $C_1$-$C_{12}$ alkyl, haloalkyl, cycloalkyl, $C_2$-$C_{12}$ alkenyl, cycloalkylene, alkynyl, $C_6$-$C_{13}$ aryl, $C_1$-$C_5$ alkoxy, hydroxy, thiophen, het, furanyl, benzo[b]thiophen, naphthyl, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), or a pharmaceutically acceptable derivative.

In a preferred embodiment, said compound of formula (2) selectively inhibits CYP11B1 ($IC_{50}$ of less than 105 or 100) and does not substantially inhibit CYP17 (not more than 30, 25, 20, or 10 or 5%) and/or CYP19 (not more than 30, 25, 20, 15 or 10 or 5%).

In certain embodiments, provided that in said compound of formula (2), when $R^5$ is $C_6$-$C_{13}$ aryl it cannot be phenyl (non-substituted), 2-methoxy substituted phenyl or a 3-amino substituted phenyl, 4-fluorine substituted phenyl, 3,4-methoxy substituted phenyl, 3-methoxy substituted phenyl, 3,4-fluorine substituted phenyl, 4-substituted methoxy phenyl.

In other embodiments, provided that in said compound of formula (2), when $R^7$ is H and that one or both of $R^5$ or $R^6$ are independently either H, aryl or heteroaryl; wherein aryl or heteroaryl may be unsubstituted or substituted further with $R^3$ (wherein where multiple substitution with $R^3$ is possible, the substituents can be independently selected from $R^3$). If only one of $R^5$ or $R^6$ is independently either H, aryl or heteroaryl, the other $R^5$ or $R^6$ can be as defined herein.

In a preferred embodiment, the present invention provides an imidazol-1-ylmethyl-pyridine compound of formula (3):

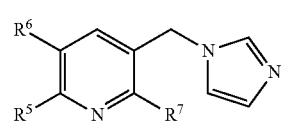

(3)

wherein, $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, CN, $NO_2$ or OAc, $R^4$ is H, OH, $C_1$-$C_5$ alkoxy, alkyl or aryl, $R^5$ is H, $C_1$-$C_{12}$ alkyl, haloalkyl, cycloalkyl, alkenyl, cycloalkylene, alkynyl, $C_6$-$C_{13}$ aryl, naphthyl, $C_1$-$C_5$ alkoxy, hydroxy, halogen, furanyl, benzo[b]thiophen, thiophen, CN, $NO_2$, OAc, amino, amido, $C(O)R^4$, $OC(O)R^4$, trityl or Het; which may be unsubstituted or substituted further with $R^3$ (wherein where multiple substitution with $R^3$ is possible, the substituents can be independently selected from $R^3$), Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^6$ is H, $C_1$-$C_{12}$ alkyl, haloalkyl, cycloalkyl, $C_1$-$C_5$ alkoxy, hydroxy, halogen, alkenyl, cycloalkylene, alkynyl, $C_6$-$C_{13}$ aryl, naphthyl, furanyl, thiophen, benzo[b]thiophen, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), $R^7$ is H, Halogen, $C_1$-$C_{12}$ alkyl, haloalkyl, cycloalkyl, $C_2$-$C_{12}$ alkenyl, cycloalkylene, alkynyl, $C_6$-$C_{13}$ aryl, $C_1$-$C_5$ alkoxy, hydroxy, thiophen, het, furanyl, benzo[b]thiophen, naphthyl, CN, $NO_2$, OAc, amino, amido, $C(O)R^4$, $OC(O)R^4$, trityl or het; which may be unsubstituted or substituted further with R³ (wherein where multiple substitution with R³ is possible, the substituents can be independently selected from R³),
or a pharmaceutically acceptable derivative.

In some embodiments, said compound of formula (3) is for use in the treatment of a condition characterized by abnormal activity or abnormal expression/level of steroid-11β-hydroxylase (CYP11B1).

In certain embodiments, provided that in said compound of formula (3), when R⁵ is $C_6$-$C_{13}$ aryl it cannot be phenyl (non-substituted), 2-methoxy substituted phenyl or a 3-amino substituted phenyl, 4-fluorine substituted phenyl, 3,4-methoxy substituted phenyl, 3-methoxy substituted phenyl, 3,4-fluorine substituted phenyl, 4-substituted methoxy phenyl.

In one embodiment, the selective CYP11B1 inhibitor is characterized by having a selectivity factor ($IC_{50}$ (CYP11B2)/$IC_{50}$ (CYP11B1)) greater than about 5. In another embodiment, the selective CYP11B1 inhibitor is characterized by having a selectivity factor ($IC_{50}$ (CYP11B2)/$IC_{50}$ (CYP11B1)) greater than about 10. In a yet further embodiment, the selective CYP11B1 inhibitor is characterized by having a selectivity factor ($IC_{50}$ (CYP11B2)/$IC_{50}$ (CYP11B1)) greater than about 20. In some embodiments, the selective CYP11B1 inhibitor is characterized by having a selectivity factor ($IC_{50}$ (CYP11B2)/$IC_{50}$ (CYP11B1)) greater than about 30. In further embodiments, the selective CYP11B1 inhibitor is characterized by having a selectivity factor ($IC_{50}$ (CYP11B2)/$IC_{50}$ (CYP11B1)) greater than about 40. In another embodiment, the selective CYP11B1 inhibitor is characterized by having a selectivity factor ($IC_{50}$ (CYP11B2)/$IC_{50}$ (CYP11B1)) greater than about 45, 46, 47 or 48. In other embodiments, the selective CYP11B1 inhibitor is characterized by having a selectivity factor ($IC_{50}$ (CYP11B2)/$IC_{50}$ (CYP11B1)) of about 49 or 50.

In one embodiment, the selective CYP11B1 inhibitor is a compound selected from

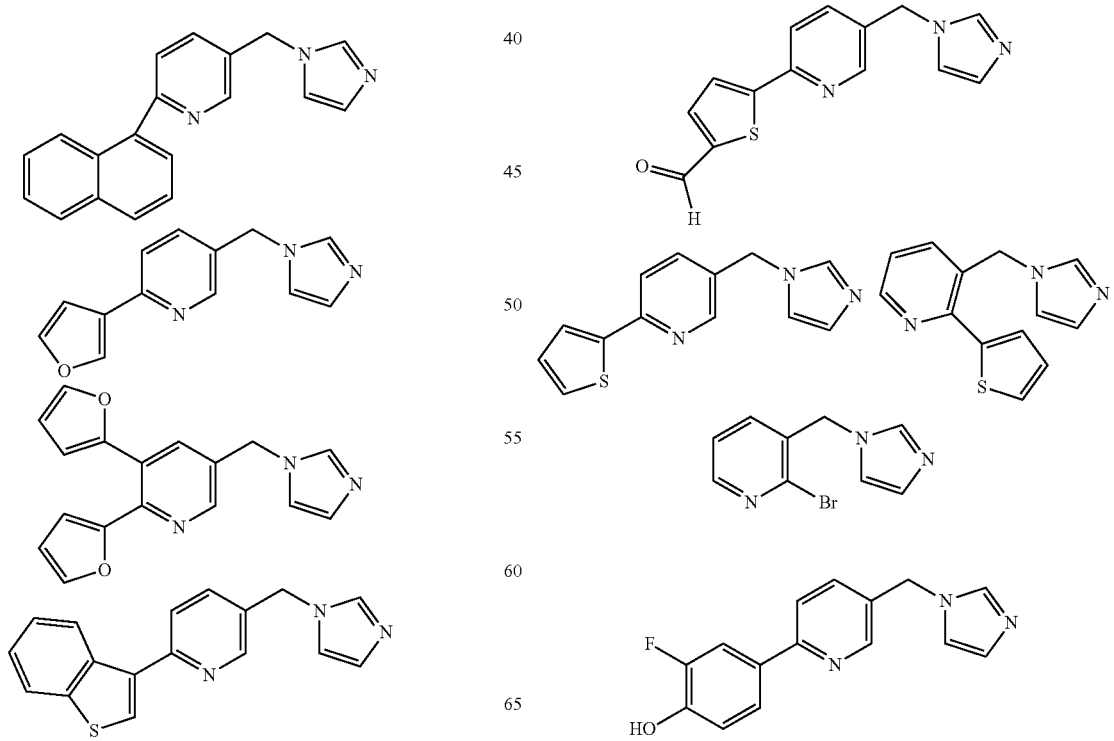

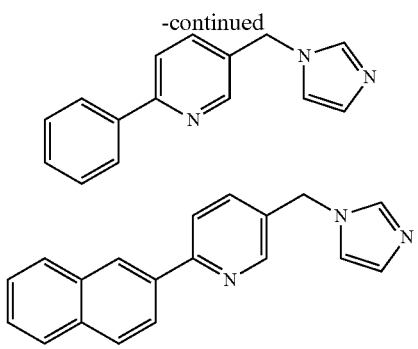

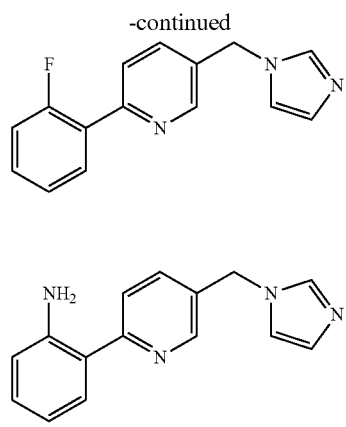

In one embodiment, the selective CYP11B1 inhibitor is a compound selected from 5-Imidazol-1-ylmethyl-2-naphthalen-1-yl-pyridine, 2-Furan-3-yl-5-imidazol-1-ylmethyl-pyridine, 2,3-Di-furan-2-yl-5-imidazol-1-ylmethyl-pyridine, 2-Benzo[b]thiophen-3-yl-5-imidazol-1-ylmethyl-pyridine, 2-(2-Fluoro-phenyl)-5-imidazol-1-ylmethyl-pyridine, 5-Imidazol-1-ylmethyl-2-thiophen-3-yl-pyridine, 3-(5-(midazol-1-ylmethyl-pyridin-2-yl)-phenylamine, 2-(5-(midazol-1-ylmethyl-pyridin-2-yl)-phenylamine, 2-Furan-2-yl-5-imidazol-1-ylmethyl-pyridine, 5-Imidazol-1-ylmethyl-2-(2-methoxy-phenyl)-pyridine, 5-(5-Imidazol-1-ylmethyl-pyridin-2-yl)-thiophene-2-carbaldehyde, 5-Imidazol-1-ylmethyl-2-thiophen-2-yl-pyridine, 3-Imidazol-1-ylmethyl-2-thiophen-2-yl-pyridine, 2-Bromo-3-imidazol-1-ylmethyl-pyridine, 2-Fluoro-4-(5-imidazol-1-ylmethyl-pyridin-2-yl)-phenol, 5-Imidazol-1-ylmethyl-2-phenyl-pyridine or 5-Imidazol-1-ylmethyl-2-naphthalen-2-yl-pyridine for use in the treatment of Cushing's syndrome or metabolic disease or metabolic syndrome.

In a most preferred embodiment for the selective CYP11B1 inhibitor of the current invention, the compound is selected from:

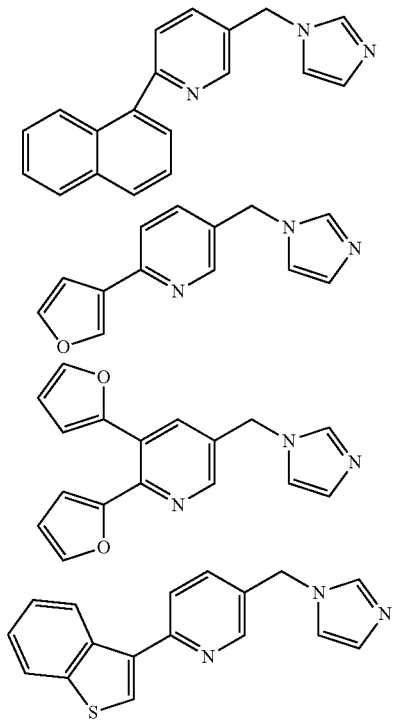

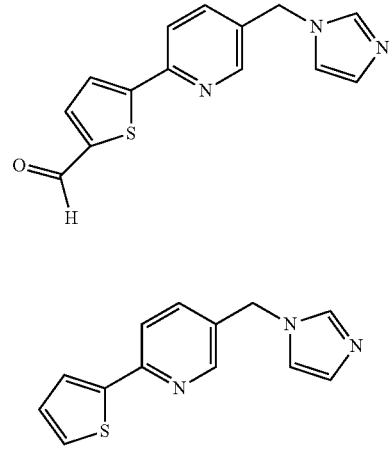

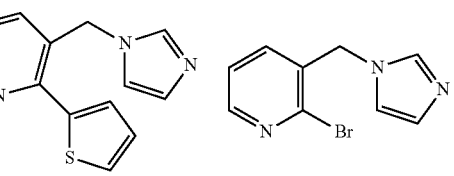

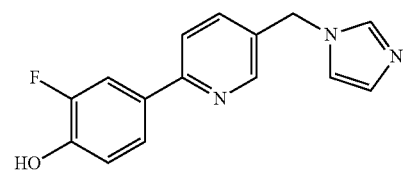

In another embodiment for the selective CYP11B1 inhibitor of the current invention, the compound is 5-Imidazol-1-ylmethyl-2-naphthalen-1-yl-pyridine, 2-Furan-3-yl-5-imidazol-1-ylmethyl-pyridine, 2,3-Di-furan-2-yl-5-imidazol-1-ylmethyl-pyridine, 2-Benzo[b]thiophen-3-yl-5-imidazol-1-ylmethyl-pyridine, 2-(2-Fluoro-phenyl)-5-imidazol-1-ylmethyl-pyridine, 2-(5-Imidazol-1-ylmethyl-pyridin-2-yl)-phenylamine, 5-(5-Imidazol-1-ylmethyl-pyridin-2-yl)-thiophene-2-carbaldehyde, 5-Imidazol-1-ylmethyl-2-thiophen-2-yl-pyridine, 3-Imidazol-1-ylmethyl-2-thiophen-2-yl-pyridine, 2-Bromo-3-imidazol-1-ylmethyl-pyridine or 2-Fluoro-4-(5-imidazol-1-ylmethyl-pyridin-2-yl)-phenol.

In some embodiments a preferred compound of the current invention is:

the compound 5-Imidazol-1-ylmethyl-2-naphthalen-1-yl-pyridine

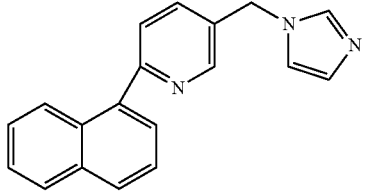

or the compound 2-Furan-3-yl-5-imidazol-1-ylmethyl-pyridine

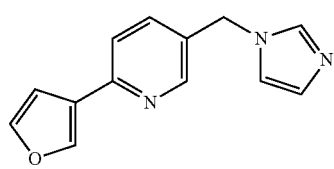

or the compound 2,3-Di-furan-2-yl-5-imidazol-1-ylmethyl-pyridine

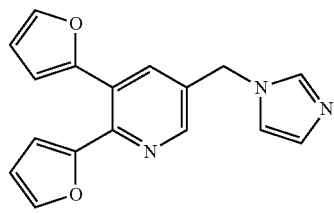

or the compound 2-Benzo[b]thiophen-3-yl-5-imidazol-1-ylmethyl-pyridine

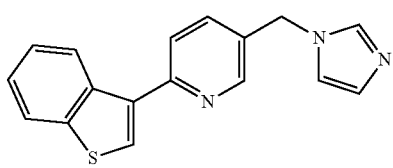

or the compound 2-(2-Fluoro-phenyl)-5-imidazol-1-ylmethyl-pyridine

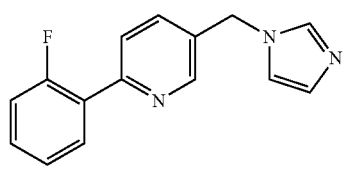

or the compound 2-(5-Imidazol-1-ylmethyl-pyridin-2-yl)-phenylamine

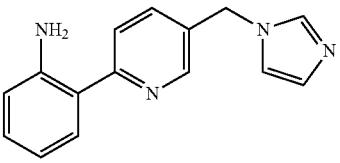

or the compound 5-(5-Imidazol-1-ylmethyl-pyridin-2-yl)-thiophene-2-carbaldehyde

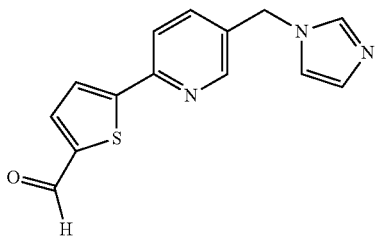

or the compound 5-Imidazol-1-ylmethyl-2-thiophen-2-yl-pyridine

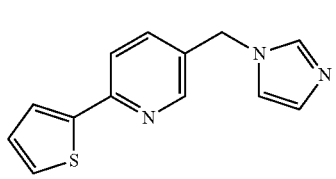

or the compound 3-Imidazol-1-ylmethyl-2-thiophen-2-yl-pyridine

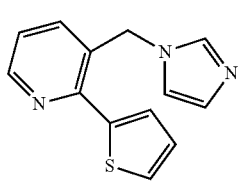

or the compound 2-Bromo-3-imidazol-1-ylmethyl-pyridine

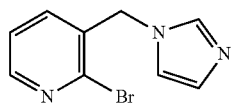

or the compound 2-Fluoro-4-(5-imidazol-1-ylmethyl-pyridin-2-yl)-phenol

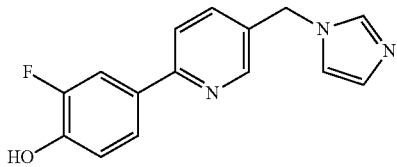

In yet another embodiment, the present invention provides an imidazol-1-ylmethyl-pyridine compound of formula (3):

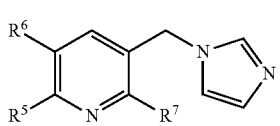

(3)

wherein, $R^3$ is $C_1$-$C_{12}$ alkyl, haloalkyl, $C_1$-$C_5$ alkoxy, hydroxy, $C_6$-$C_{13}$ aryl, halogen, amino, amido, ester, ether, $C(O)R^4$, $OC(O)R^4$, $SO_2R^4$, $SO_2NHR^4$, CN, $NO_2$ or OAc, $R^4$ is H, OH, alkyl or aryl, $R^5$ is H, $C_1$-$C_{12}$ alkyl, haloalkyl, cycloalkyl, alkenyl, cycloalkylene, alkynyl, $C_6$-$C_{13}$ aryl, naphthyl, $C_1$-$C_5$ alkoxy, hydroxy, halogen, furanyl, benzo[b]thiophen, thiophen, CN, $NO_2$, OAc, amino, amido, $C(O)R^4$, $OC(O)R^4$, trityl or Het; which may be unsubstituted or substituted further with $R^3$ (wherein where multiple substitution with $R^3$ is possible, the substituents can be independently selected from $R^3$), Het is heteroaryl, heteroarylium, heterocyclyl, heteroaralkyl, heteroarylene, heterocyclylene; preferably het is imidazolyl, pyridyl, pyrimidyl, triazolyl, oxazolyl, isoxazolyl, thiazolyl, isothiazolyl, benzotriazolyl, benzoimidazolyl, quinolinyl, isoquinolinyl, quinazolinyl, benzooxazolyl, benzothiazolyl, benzo[d]isoxazolyl, benzo[d]isothiazolyl, 4,5,6,7-tetrahydro-1H-benzo[d]imidazolyl, 5,6,7,8-tetrahydroisoquinolinyl;

more preferably het is 1-imidazolyl, 5-imidazolyl, 3-pyridinyl, 4-pyridinyl, 5-pyrimidinyl, 3-(6-methoxypyridinyl), 4-isoquinolinyl, 8-quinazolinyl, or benzo[b]imidazolyl, 4-oxazolyl, 4-isoxazolyl, 4-thiazolyl, 4-isothiazolyl, 4-benzooxazolyl, 4-benzothiazolyl, 4-benzo[d]isoxazolyl, 4-benzo[d]isothiazolyl, 4,5,6,7-tetrahydro-1H-benzo[d]imidazolyl, 5,6,7,8-tetrahydroisoquinolinyl, Het can be unsubstituted or is substituted further with $R^3$. Het can also be further annelated by 5- or 6-membered rings, which can also be substituted with $R^3$ (wherein where multiple substitution with $R^3$ is possible, the substituents can be independently selected from $R^3$), $R^6$ is H, $C_1$-$C_{12}$ alkyl, haloalkyl, cycloalkyl, $C_1$-$C_5$ alkoxy, hydroxy, halogen, alkenyl, cycloalkylene, alkynyl, $C_6$-$C_{13}$ aryl, naphthyl, furanyl, thiophen, benzo[b]thiophen, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), $R^7$ is H, Halogen, $C_1$-$C_{12}$ alkyl, haloalkyl, cycloalkyl, $C_2$-$C_{12}$ alkenyl, cycloalkylene, alkynyl, $C_6$-$C_{13}$ aryl, $C_1$-$C_5$ alkoxy, hydroxy, thiophen, het, furanyl, benzo[b]thiophen, naphthyl, CN, $NO_2$, OAc, amino, amido, $C(O)R^4$, $OC(O)R^4$, trityl or het; which may be unsubstituted or substituted further with $R^3$ (wherein where multiple substitution with $R^3$ is possible, the substituents can be independently selected from $R^3$), or a pharmaceutically acceptable derivative, for use in the treatment of a condition characterized by abnormal activity or abnormal expression/level of steroid-11β-hydroxylase (CYP11B1).

In some aspects, the compounds of the present invention are for use as a medicament, preferably for use in the treatment of a condition characterized by abnormal activity or abnormal expression/level of steroid-11β-hydroxylase (CYP11B1).

As used herein, the term "abnormal" refers to an activity or feature which differs from a normal activity or feature. As used herein, the term "abnormal activity" refers to an activity which differs from the activity of the wild-type or native gene or protein, or which differs from the activity of the gene or protein in a healthy subject. The abnormal activity can be stronger or weaker than the normal activity. In one embodiment, the "abnormal activity" includes the abnormal (over-) production of mRNA transcribed from a CYP11B1 gene. In another embodiment, the "abnormal activity" includes the abnormal (over-) production of a CYP11B1 polypeptide from its gene. In another embodiment, the abnormal activity refers to a level of a CYP11B1 mRNA or CYP11B1 polypeptide that is different from a normal level of said mRNA or polypeptide by about 15%, about 25%, about 35%, about 50%, about 65%, about 85%, about 100% or greater. Preferably, the abnormal level of the mRNA or polypeptide is higher or lower than the normal level of said mRNA or polypeptide. Yet in another embodiment, the abnormal activity refers to functional activity of a protein that is different from a normal activity of the wild-type protein. Preferably, the abnormal activity can be stronger than the normal activity. For example, the abnormal activity is due to the mutations in the corresponding gene, and the mutations can be in the coding region of the gene or non-coding regions such as transcriptional promoter regions. The mutations can be substitutions, deletions, insertions.

In other aspects, the compounds of the present invention are for use in treating cortisol dependent disorder. In further aspects, the disorder is selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after stroke and the cortisol-induced mineralocorticoid excess. The treatment of Cushing's syndrome by applying the compounds of the present invention is preferred. It certain preferred embodiments, the compounds of the present invention when applied for the treatment of Cushing's syndrome can be applied in combination with ketoconazole, etomidate, metyrapone, sodium-valproate, bromocriptine, octreotide, o,p'DDD, aminogluthethimide, metyrapone, retinoic acid and/or cyproheptadine.

In other aspects, the compounds of the present invention are for use in treating weight loss.

The compounds of the present invention may also be used in a method of treating a disorder characterized by an abnormal activity or abnormal expression/level of CYP11B1 in a subject, wherein the method comprises administering to the subject a therapeutically effective amount of the compound of the present invention.

As used herein, the term "a disorder" or "a disease" refers to any derangement or abnormality of function; a morbid physical or mental state. See Dorland's Illustrated Medical Dictionary, (W.B. Saunders Co. 27th ed. 1988).

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that (selectively) inhibits or reduces activity of CYP11B1. As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

In another aspect, a compound of the present invention can be present in a pharmaceutical composition comprising a therapeutically effective amount of a compound and one or more pharmaceutically acceptable carriers.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art; see, for example, Remington's Pharmaceutical Sciences, 18th Ed. Mack Printing Company, 1990, pp. 1289-1329. Except insofar as any conventional carrier is incompatible with the active ingredient, its use in the therapeutic or pharmaceutical compositions is contemplated.

In a further aspect, the pharmaceutical composition comprising an additional pharmacologically active compound.

The results obtained for some of the preferred compounds of the present invention are demonstrated below in Tables 1-3. Of note, the compounds in these Tables are compounds of the present invention, apart from MTP: metyrapone; ETO: etomidate; KTZ: ketoconazole. Likewise, also the compounds described in the appended Examples are compounds of the present invention.

TABLE 1

Inhibition of CYP11B2 and CYP11B1 by compounds 2-22

| No. | $R^5$ | $R^6$ | $R^7$ | CYP11B1 | CYP11B2 | sf[c] |
|-----|-------|-------|-------|---------|---------|-------|
| 2   |       |       |       | 663     | >1000   |       |
| 3   |       |       |       | 816     | >1000   |       |
| 4   |       |       | CN    | 971     | >1000   |       |
| 1[a]| Br    |       |       | 500     | >1000   |       |
| 5   |       |       | Br    | 61      | 911     | 15    |
| 6   | Cl    |       | Br    | 168     | 576     | 3.4   |
| 7   | F     |       |       | 72      | 1736    | 24    |
| 8   |       | F     |       | 320     | >1000   |       |
| 9   |       |       | F     | 213     | 2153    | 10    |
| 10  |       | F     | F     | 329     | 1665    | 5     |
| 11  |       | F     | OH    | 17      | 237     | 14    |
| 12  | MeO   |       |       | 167     | 4391    | 26    |
| 13  |       | MeO   |       | 782     | >1000   |       |
| 14  |       | MeO   | MeO   | >1000   | >1000   |       |
| 15  | $NH_2$|       |       | 101     | 2114    | 21    |
| 16  |       | $NH_2$|       | 110     | 3407    | 31    |
| 17  |       |       | $NH_2$| 106     | 528     | 5     |
| 18  |       | $NH_2$| Me    | 542     | >1000   |       |
| 19  |       |       | CN    | 409     | >1000   |       |
| 20  |       |       | CN    | 782     | >1000   |       |
| 21  |       |       | CHO   | 246     | >1000   |       |
| 22  |       |       | di-Ph—N | 611   | n.i.[d] |       |
| 1   |       |       |       | 152     | 2768    | 18    |
| MTP[e] |    |       |       | 15      | 72      | 4.8   |
| ETO[e] |    |       |       | 0.5     | 0.1     | 0.2   |
| KTZ[e] |    |       |       | 127     | 67      | 0.5   |

[a] Mean value of at least three experiments. The deviations were within <±25 %.

[b] Hamster fibroblasts expressing human CYP11B1 or CYP11B2; substrate 11-deoxycorticosterone, 100 nM

[c] sf: selectivity factor: $IC_{50}$ (CYP11B2)/$IC_{50}$ (CYP11B1)

[d] n.i.: no inhibition at an inhibitor concentration of 500 nM

[e] MTP: metyrapone; ETO: etomidate; KTZ: ketoconazole

TABLE 2

Inhibition of CYP11B2 and CYP11B1 by compounds 23-42

| | | | | | |
|---|---|---|---|---|---|
| | | Structure | | $IC_{50}$ value (nM)[a,b] | |
| No. | $R^5$ | $R^6$ | CYP11B1 | CYP11B2 | sf[c] |
| 23 | 1-naphthalene | | 42 | 2075 | 49 |
| 24 | 2-naphthalene | | 246 | 782 | 3.2 |
| 25 | Ph | Ph | 362 | 851 | 2.4 |
| 26 | 3-pyridine | | 502 | 3955 | 8 |
| 27 | 4-pyridine | | 139 | 487 | 3.5 |
| 28 | 5-pyrimidine | | 971 | n.i.[d] | |
| 29 | 3-(6-methoxypyridine) | | >1000 | >1000 | |
| 30 | 4-isoquinoline | | 95 | 914 | 10 |
| 31 | 2-thiophene | | 75 | 1243 | 17 |
| 32 | 3-thiophene | | 126 | 3265 | 26 |
| 33 | 2-(5-chlorothiophene) | | 362 | 929 | 2.6 |
| 34 | 2-(5-formylthiophene) | | 62 | 968 | 16 |
| 35 | Cl | 2-thiophene | 73 | 416 | 6 |
| 36 | 2-thiophene | | 16 | 251 | 16 |
| 37 | 2-benzo[b]thiophene | | 269 | 281 | 1.0 |
| 38 | 3-benzo[b]thiophene | | 40 | 1157 | 29 |
| 39 | 2-furan | | 167 | 5159 | 31 |
| 40 | 3-furan | | 76 | 2832 | 37 |
| 41 | 2-benzo[b]furan | | 500 | >1000 | |
| 42 | 2-furan | 2-furan | 29 | 830 | 29 |
| 1 | Ph | | 152 | 2768 | 18 |
| MTP[e] | | | 15 | 72 | 4.8 |
| ETO[e] | | | 0.5 | 0.1 | 0.2 |
| KTZ[e] | | | 127 | 67 | 0.5 |

[a] Mean value of at least three experiments. The deviations were within <±25 %.
[b] Hamster fibroblasts expressing human CYP11B1 or CYP11B2; substrate 11-deoxycorticosterone, 100 nM
[c] sf: selectivity factor: $IC_{50}$ (CYP11B2)/$IC_{50}$ (CYP11B1)
[d] n.i.: no inhibition at an inhibitor concentration of 500 nM
[e] MTP: metyrapone; ETO: etomidate; KTZ: ketoconazole

TABLE 3

Inhibition of CYP19 and CYP17 of selected compounds

| | inhibition (%) | |
|---|---|---|
| Comp. | CYP 17[a,b] | CYP 19[a,c] |
| 5 | 3 | 2 |
| 7 | 3 | 0 |
| 8 | 1 | n.d. |
| 9 | 5 | n.d. |
| 10 | 0 | n.d. |
| 11 | 2.6 | 0 |
| 12 | 5 | 4 |
| 13 | 0 | n.d. |
| 14 | 2 | n.d. |
| 15 | 6 | 0 |
| 16 | 3 | 2 |
| 17 | 4 | 1 |
| 18 | 3 | 0 |
| 21 | 0 | n.d.[d] |
| 22 | 2 | 1 |
| 23 | 8 | 5 |
| 25 | 3 | 0 |
| 31 | 8 | 3 |
| 32 | 3 | 0 |
| 34 | 5 | 0 |
| 35 | 5 | 30 |
| 36 | 0 | 19 |
| 38 | 4 | 0 |
| 39 | 1 | 0 |
| 40 | 8 | 0 |
| 42 | 6.7 | 2.2 |

[a] Mean value of at least three experiments. The deviations were within <±25%.
[b] E. coli expressing human CYP17; substrate progesterone, 25 μM; inhibitor concentration 2.0 μM
[c] Human placental CYP19; substrate androstenedione, 500 nM; inhibitor concentration 500 nM
[d] n.d. = not determined

ABBREVIATIONS

CYP Cytochrome P450

CYP11B1 Steroid-11β-Hydroxylase

CYP11B2 Aldosterone synthase

CYP17 17α-Hydroxylase-17,20-lyase

CYP19 Aromatase

HbA1c Glycosylated hemoglobin

HSD Hydroxysteroid dehydrogenase $IC_{50}$ Concentration required for 50% inhibition SAR Structure activity relationship Sf Selectivity factor $S_N$ Nucleophilic substitution Also, the following compounds are also compounds of the present invention. They illustrate the present invention and are specific embodiments encompassed at least by formula (1) and (4), shown below. Accordingly, the following compounds can thus be applied in the pharmaceutical compositions, methods of treatment and/or medical uses described herein. Accordingly, all embodiments described herein in the context of formula (1), (2) or (3), pharmaceutical compositions, methods of treatment and/or medical uses are applicable for the following compounds, mutatis mutandis.

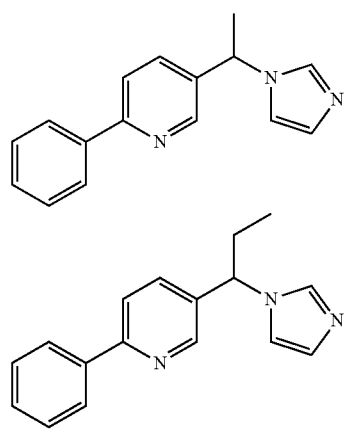

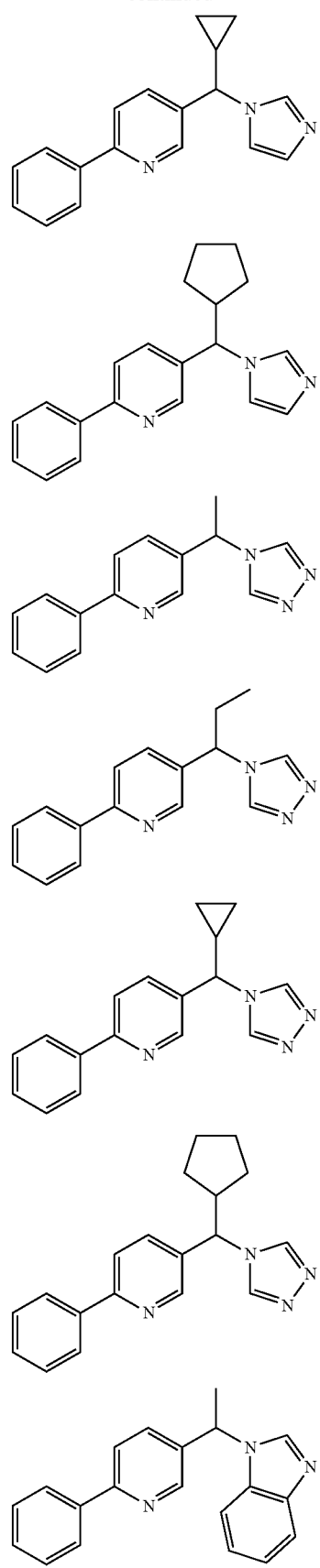
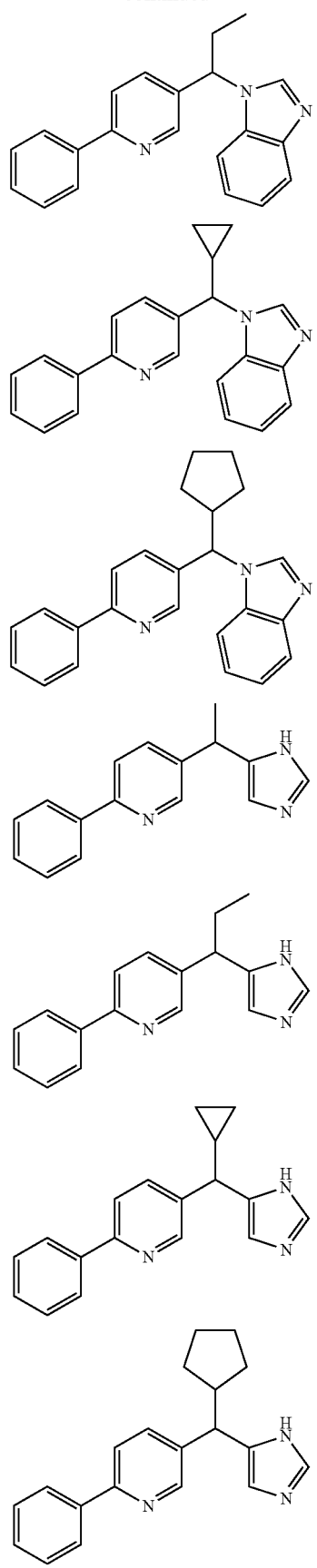

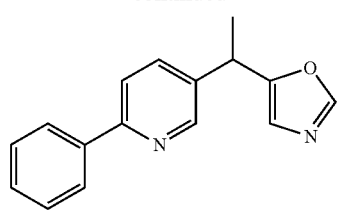
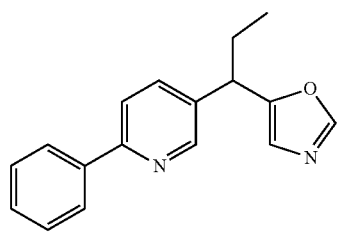
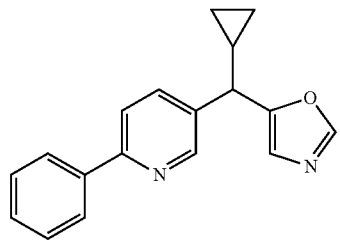
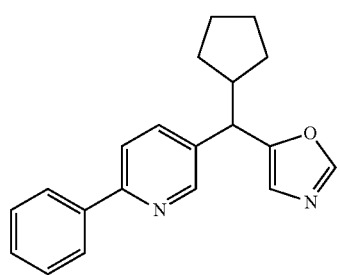
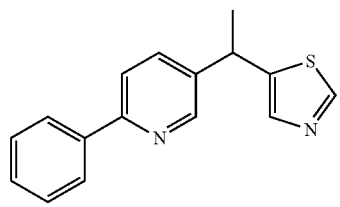
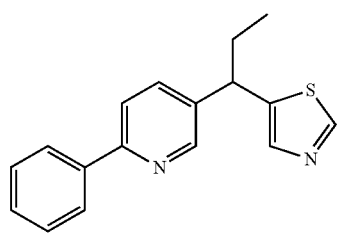
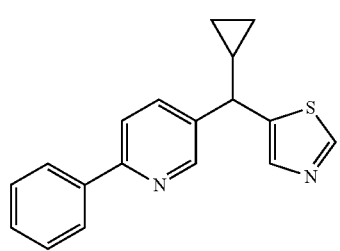
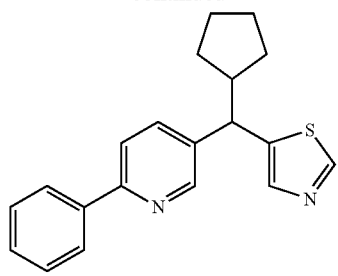
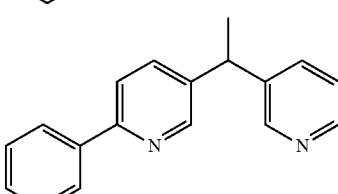
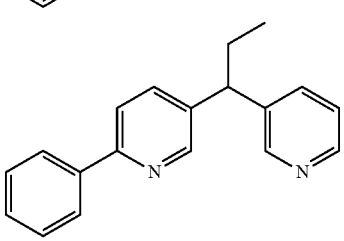
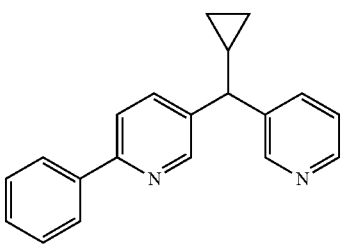
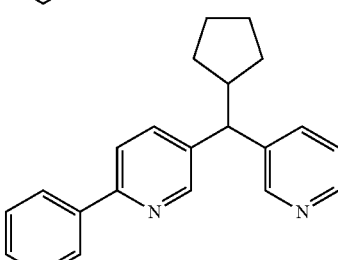
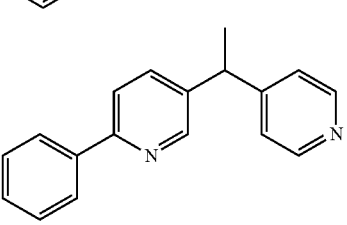
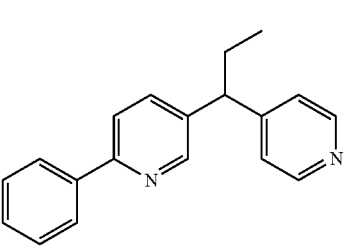

-continued
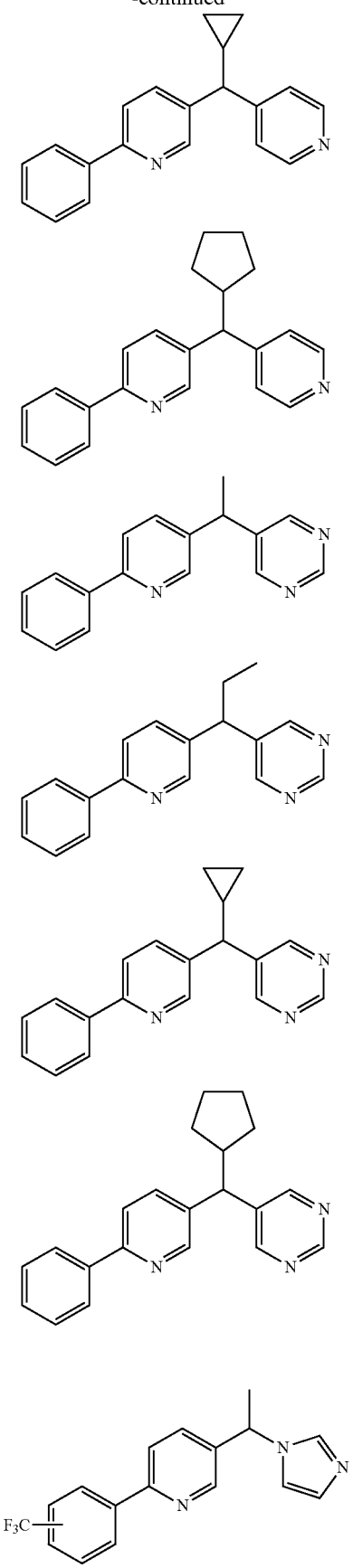
-continued
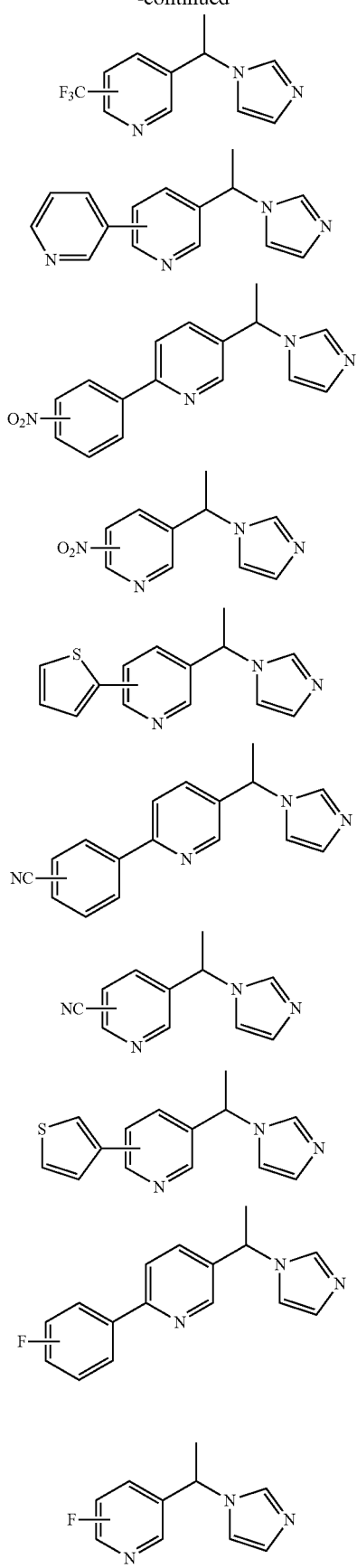

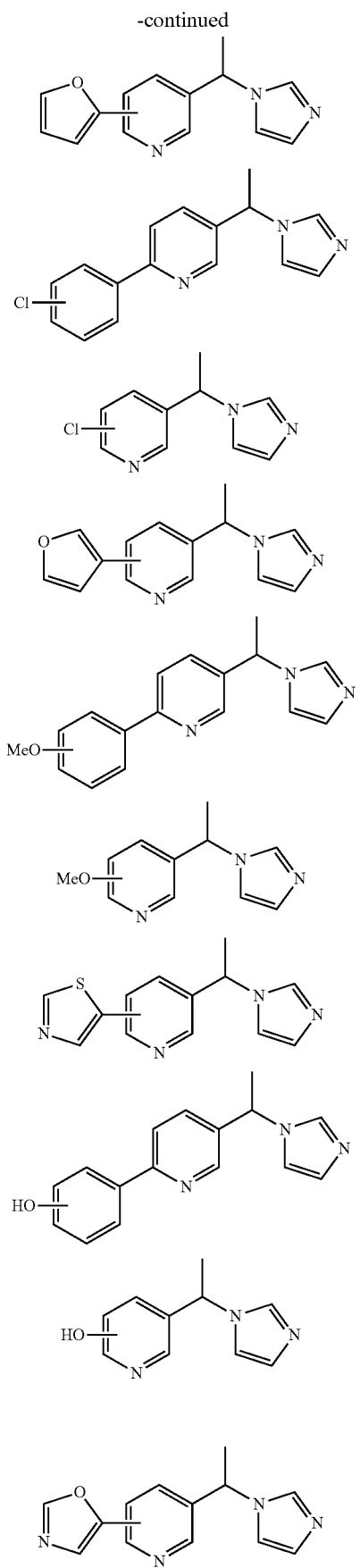
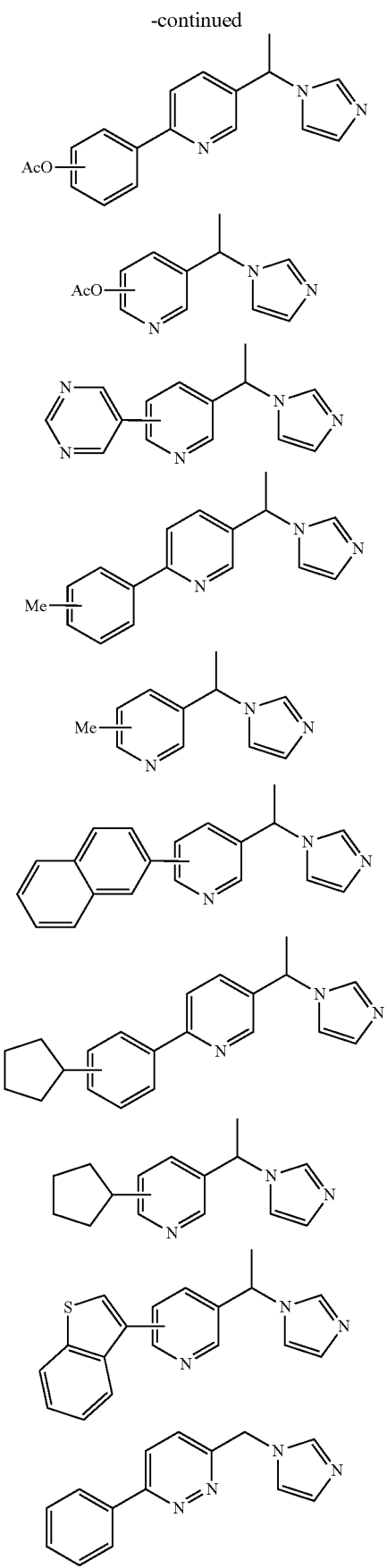

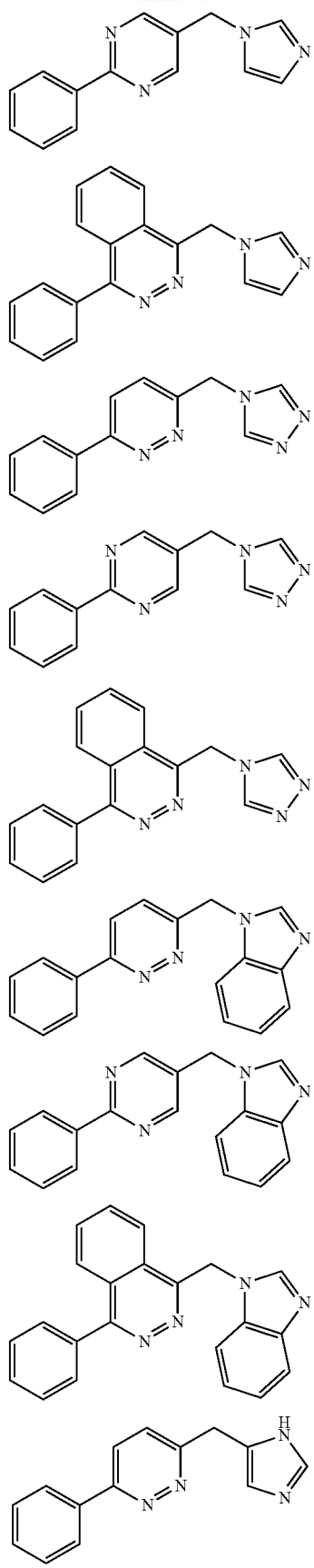
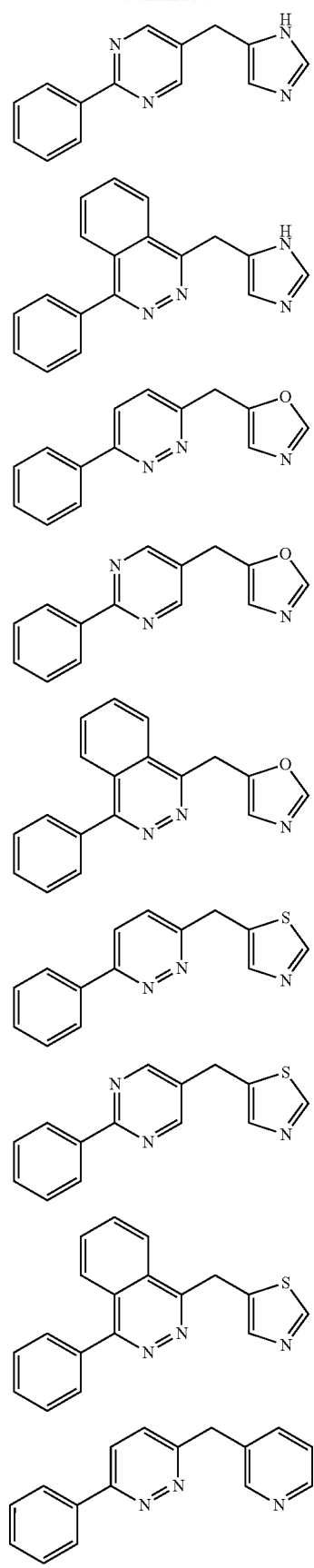

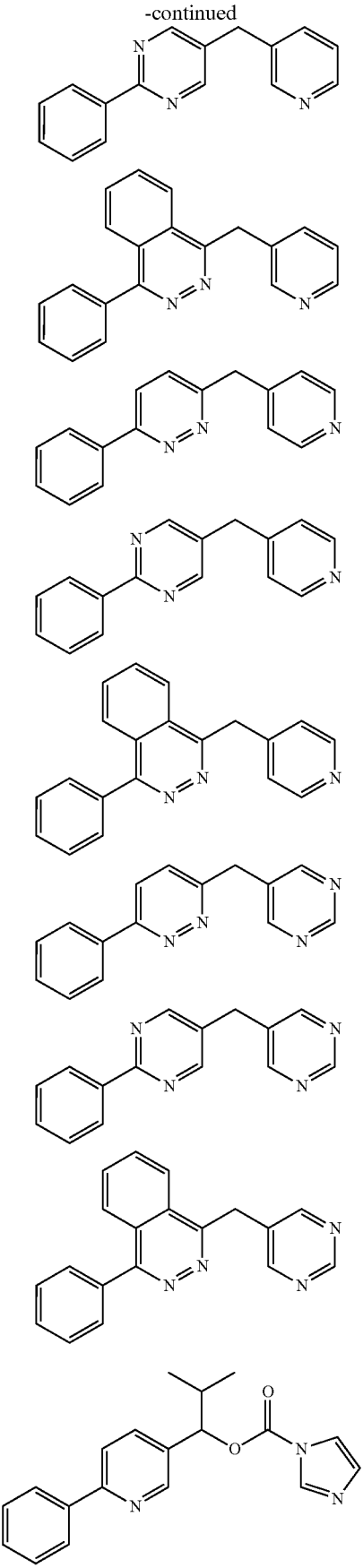
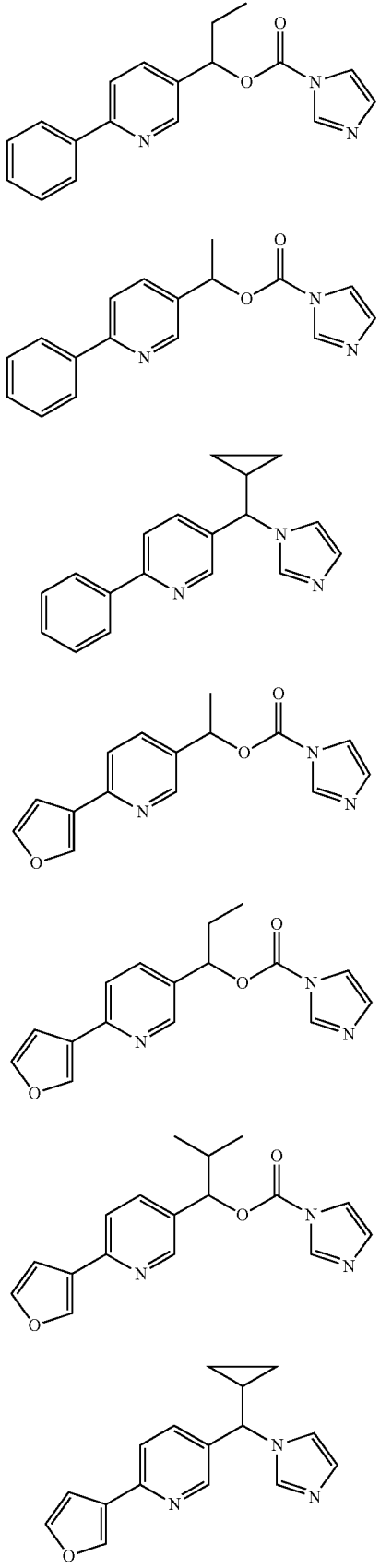

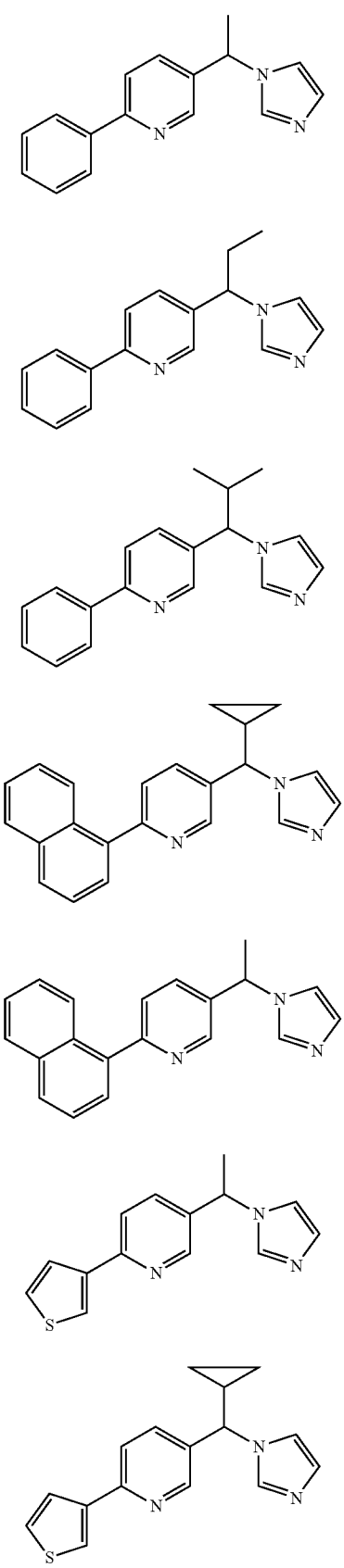
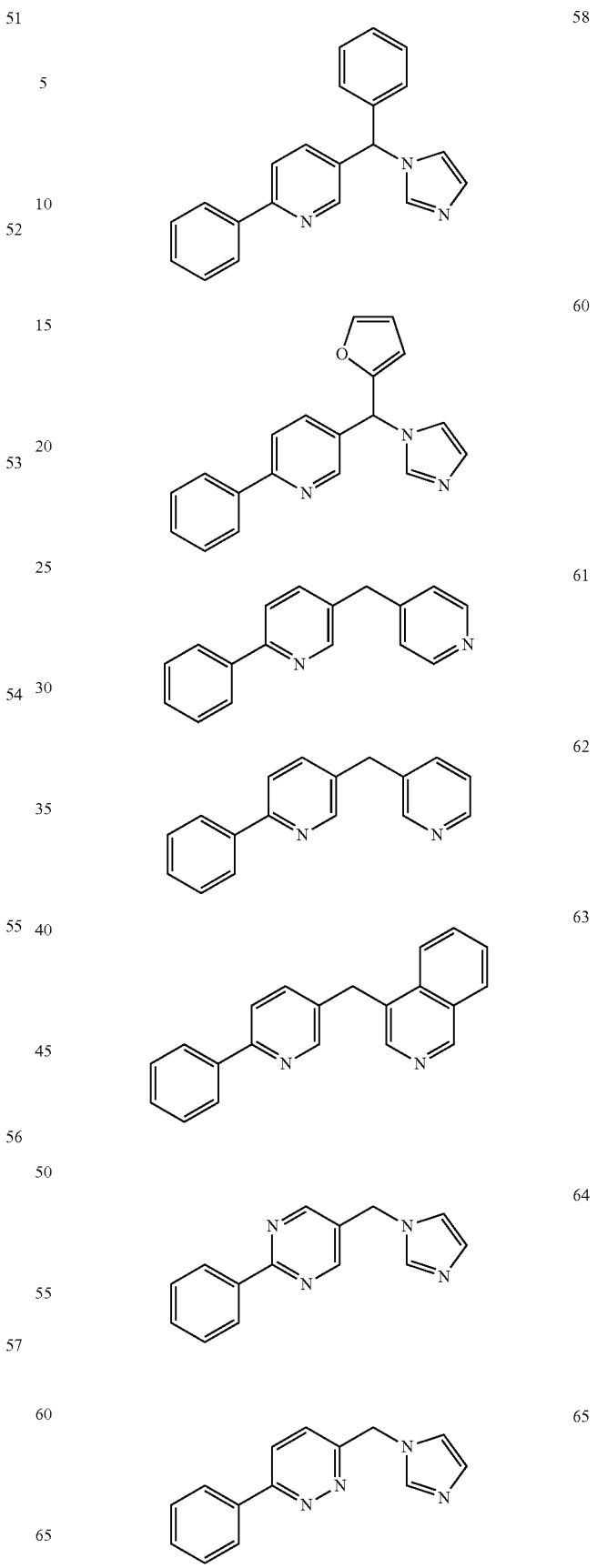

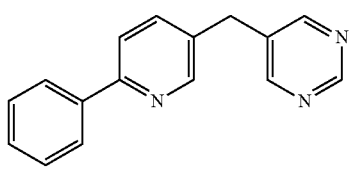

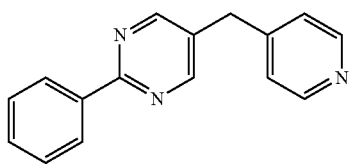

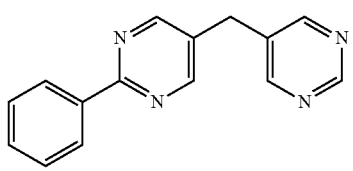

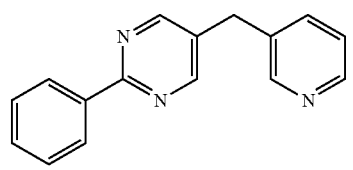

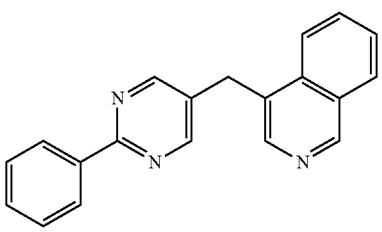

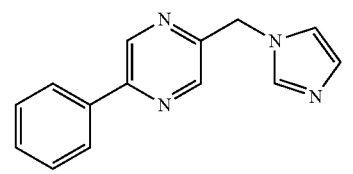

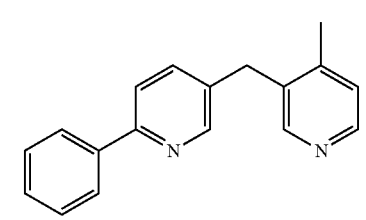

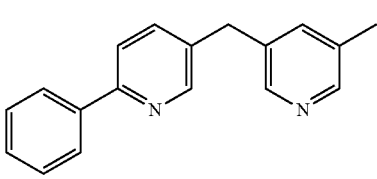

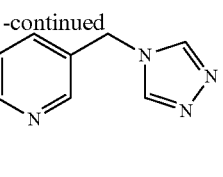

The invention also relates to the following compounds as generalized by the following formula (4):

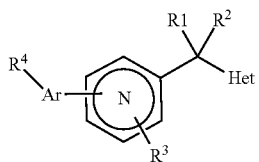

Het: imidazolyl, pyridyl, pyrimidyl, triazolyl, oxazolyl, thiazolyl, benzotriazolyl, benzoimidazolyl, quinolinyl, isoquinolinyl; (only β and γ position to methylene bridge, not α position)
which could be substituted by further $R^3$ group if possible;
N Het: aromatic ring with one to four N atoms;
especially pyridine, pyrimidine, pyridazine
which could be further annelated by 5- or 6-membered rings;
Ar: Benzene, naphthalene, heterocycles;
which could be further annelated by 5- or 6-membered rings;
$R^1$, $R^2$: could independently be H, Me, Et, c-Pr, c-pent and so on
$R^3$, $R^4$: could independently be $CF_3$, $NO_2$, CN, halogen, OMe, OH, OAc, alkyl, c-alkyl, alkyloxyl, and so on Thus, the compounds covered by formula (4) are also compounds of the present invention. Accordingly, the compounds of formula (4) can thus be applied in the pharmaceutical compositions, methods of treatment and/or medical uses described herein. Accordingly, all embodiments described herein in the context of formula (1), (2) or (3), pharmaceutical compositions, methods of treatment and/or medical uses are applicable for the compounds covered by formula (4), mutatis mutandis.

FIGURES

FIG. 1: Role of CYP11B1 and CYP11B2 in cortisol and aldosterone biosynthesis

EXAMPLES

A better understanding of the present invention and of its advantages is given from the following examples, which are offered for illustrative purposes only and which are not intended to limit the scope of the present invention in any way.

Cellular Assays for Testing CYP11B1 and CYP11B2 Inhibition

V79MZh11B1 and V79MZh11B2 cell lines were cultivated in Dulbecco's modified Eagle medium supplemented with 5% of fetal calf serum, penicillin (100 U/ml), streptomycin (100 μg/ml), glutamine (2 mM) and sodium pyruvate (1 mM) at 37° C. in 5% $CO_2$ in air.

V79MZ cells expressing human CYP11B1 and human CYP11B2 genes, respectively, were grown on 24-well cell culture plates (8×10$^5$ cells per well) with 1.9 cm$^2$ culture area per well in 1 ml DMEM culture medium until confluence. Before testing, the DMEM culture medium was removed and 450 µl of fresh DMEM, containing the inhibitor in at least three different concentrations for determining the IC$_{50}$ value, was added to each well. Every value was determined at least three times. After a pre-incubation step of 60 min at 37° C., the reaction was started by the addition of 50 µl of DMEM containing the substrate 11-deoxycorticosterone (containing 0.15 µCi of [1,2-$^3$H] 11-deoxycorticosterone, dissolved in ethanol, final concentration 100 nM).

The V79MZh11B1 cells were incubated for 25 min, the V79MZh11B2 cells were incubated for 50 min. Controls were treated in the same way without inhibitors. The maximum DMSO concentration in each well was 1%.

Enzyme reactions were stopped by extracting the supernatant with 500 µl ethyl acetate. Samples were centrifuged (10000×g, 2 min), and the solvent was pipetted into fresh cups. The solvent was evaporated and the steroids were redissolved in 40 µl of methanol and analyzed by HPLC using radioflow detection (Ehmer et al. *J. Steroid Biochem. Mol. Biol.* 2002, 81, 173-179 and Denner et al. *Endocr. Res.* 1995, 21, 443-448).

The above experiment was conducted at least three times and a mean value for the IC$_{50}$ calculated.

17A-Hydroxylase/C17-20-Lyase Assay

Enzyme Preparation of CYP17

Recombinant *E. coli* pJL17/OR coexpressing human CYP17 and rat NADPH-P450-reductase were grown and stored as described by Ehmer et al. (*J. Steroid Biochem. Mol. Biol.*, 2000, 75, 57-63)

For isolation of membrane fractions, 5 ml of bacterial suspension with an OD$_{578}$ of 50 were washed using phosphate buffer (0.05 M, pH 7.4, 1 mM MgCl$_2$, 0.1 mM EDTA and 0.1 mM dithiothreitol). Bacteria were harvested by centrifugation (2000×g) and the pellet was resuspended in 10 ml ice-cold TES buffer (0.1 M tris-acetate, pH 7.8, 0.5 mM EDTA, 0.5 M sucrose). Lysozyme was added with 10 ml of ice-cold water resulting in a concentration of 0.2 mg/ml followed by incubation for 30 min on ice with continuous shaking. Spheroplasts were harvested by centrifugation (12000×g, 10 min), and resuspended in 4 ml of ice-cold phosphate buffer (the same as described above plus 0.5 mM phenylmethylsulfonylfluoride (PMSF)).

After that spheroplasts were sonicated on ice (pulse 20 s on, 30 s off, five times), using a sonicator Sonopuls HD60 (Bandelin, Berlin, Germany) at maximum power. Unbroken cells and debris were pelleted at 3000×g for 7 min, and the supernatant was centrifuged at 50000×g for 20 min at 4° C. The membrane pellet was resuspended in 2 ml of phosphate buffer (the same as described above) with 20% glycerol using an ultra-turrax T25 (IKA-Labortechnik, Staufen, Germany). Protein concentration was determined by the method of Lowry. Aliquots of this preparation, which generally had a content of about 5 mg protein per ml, were stored at −70° C. until used.

CYP17 Inhibition Assay

The assay was performed as follows: a solution of 6.25 nmol progesterone (in 5 µl methanol) in 140 µl phosphate buffer (0.05 M, pH 7.4, 1 mM MgCl$_2$, 0.1 mM EDTA and 0.1 mM dithiothreitol), 50 µl NADPH generating system (in phosphate buffer with 10 mM NADP, 100 mM glucose-6-phosphate and 2.5 units of glucose-6-phosphate-dehydrogenase) and inhibitor (in 5 µl DMSO) was pre-incubated at 37° C. for 5 min. Control cups were supplemented with 5 µl DMSO without inhibitor. The reaction was started by adding 50 µl of a 1:5 diluted membrane suspension in phosphate buffer (0.8-1.0 mg protein per ml). The maximum DMSO concentration in each sample was 2%. After mixing, incubation was performed for 30 min at 37° C. Subsequently the reaction was stopped with 50 µl 1 N HCl.

Extraction of the steroids was performed by addition of 1.0 ml ethyl acetate and vigorous shaking for 1 min. After a centrifugation step (5 min, 2500×g) the organic phase (0.9 ml) was transferred into a fresh cup containing 0.25 ml of incubation buffer and 50 µl 1 N HCl and mixed again. After centrifugation, 0.8 ml ethyl acetate solution was evaporated to dryness in a fresh cup. After that the steroids were redissolved in solvent for HPLC analysis (Hutschenreuter et. al. *J. Enz. Inhib. Med. Chem.* 2004, 19, 17-32).

The above experiment was conducted at least three times and a mean value for the CYP17 inhibition calculated.

CYP 19 (Aromatase) Assay

Preparation of Aromatase

The enzyme was obtained from the microsomal fraction of freshly delivered human term placental tissue according to the procedure of Thompson and Siiteri (Thompson, E. A.; Siiteri, P. K. *J. Biol. Chem.* 1974, 249, 5364).

The isolated microsomes were suspended in a minimum volume of phosphate buffer (0.05 M, pH 7.4, 20% glycerol). Additionally, DTT (dithiothreitol, 10 mM) and EDTA (1 mM) were added to protect the enzyme from degradation. The enzyme preparation was stored at −70° C.

Inhibition of Aromatase

The assay was performed monitoring enzyme activity by measuring the $^3$H$_2$O formed from [1β-$^3$H]androstenedione during aromatization (Hartmann et al. *J. Med. Chem.* 1986, 29, 1362-1369). Each incubation tube contained 15 nM [1β-$^3$H]androstenedione (0.08 µCi), 485 nM unlabeled androstenedione, 2 mM NADP, 20 mM glucose-6-phosphate, 0.4 units of glucose-6-phosphate-dehydrogenase and inhibitor (in at least three different concentrations for determining the IC$_{50}$ value) in phosphate buffer (0.05 M, pH 7.4). The test compounds were dissolved in DMSO and diluted with buffer. The final DMSO concentration in the control and inhibitor incubation was 2%. Each tube was pre-incubated for 5 min at 30° C. in a water bath. Microsomal protein was added to start the reaction (0.1 mg). The total volume for each incubation was 0.25 ml. The reaction was terminated by the addition of 200 µl of a cold 1 mM HgCl$_2$ solution. After addition of 200 µl of an aqueous dextran-coated charcoal (DCC) suspension (2%), the vials were shaken for 20 min and centrifuged at 1500×g for 5 min to separate the charcoal-absorbed steroids. The supernatant was assayed for $^3$H$_2$O by counting in a scintillation mixture using a β-counter. The calculation of the IC$_{50}$ values was performed by plotting the percent inhibition vs. the concentration of inhibitor on a semi-log plot. From this the molar concentration causing 50% inhibition was calculated.

The above experiment was conducted at least three times and a mean value for the CYP19 inhibition calculated.

Chemistry

1H NMR and 13C spectra were recorded on a Bruker DRX-500 instrument. Chemical shifts are given in parts per million (ppm) and spectra are obtained as DMSO-d6 or CDCl3 solutions (reported in ppm), using chloroform as the reference standard (7.26 ppm) or DMSO-d6 (2.50 ppm). The following abbreviations are used to denote signal multiplicities: s=singlet, d=doublet, t=triplet, m=multiplet, and br=broadened. All coupling constants (J) are given in hertz (Hz). Mass spectra (LC/MS) were measured on a TSQ Quantum (Thermo Electron Corporation) instrument with a RP18 100-3 column (Macherey Nagel) and with water/acetonitrile mixtures as eluents. The purity of all compounds was ≥95%. Reagents were used as obtained from commercial suppliers without further purification. Yields refer to purified products and are not optimized. Solvents were distilled before use. Dry solvents were obtained by distillation from appropriate drying reagents and stored over molecular sieves. Flash chromatography was performed on silica gel 40 (35/40-63/70 µM) with petroleum ether/ethyl acetate mixtures as eluents, and the reaction progress was determined by thin-layer chromatography analyses on Alugram SIL G/UV$_{254}$ (Macherey Nagel). Visualization was accomplished with UV light and $KMnO_4$ solution.

Method A: Wohl Ziegler Bromination

Methylpyridine was dissolved in 40 mL of dry carbon tetrachloride. To this solution was added N-bromsuccinimide (NBS) (1.1 eq) and benzoyl peroxide (5 mol %) and the mixture was refluxed over night. After cooling, the succinimide was removed by filtration and the filtrate was concentrated under vacuum. The crude product was further purified by flash column chromatography on silica gel using a mixture of petroleum ether/ethyl acetate (95:5) as eluent.

Method B: $S_N$-Reaction

The α-brominated compounds, imidazole (2 eq), a catalytic amount of 18-crown-6 and anhydrous $K_2CO_3$ (1.5 eq) in dry acetonitrile were heated under reflux overnight. After cooling, water (50 mL) was added, and the aqueous layer was extracted with ethyl acetate (3×30 mL). The combined organic layers were washed with brine (25 mL), dried over $Na_2SO_4$ and evaporated in vacuo. The crude product was purified by column chromatography on silica-gel, using 5% methanol in ethyl acetate.

Method C: Suzuki-Coupling.

The corresponding benzene derivative and the boronic acid were dissolved in toluene (20 mL) and aq. $Na_2CO_3$ (2.0 M, 5.0 mL). The mixture was deoxygenated under reduced pressure and flushed with $N_2$. After having repeated this cycle three times, Pd(PPh$_3$)$_4$ (5 mol %) was added, and the resulting suspension was heated under reflux for 8 h. After cooling, the phases were separated and the water phase was extracted two times with ethyl acetate. The combined organic extracts were dried over $Na_2SO_4$, and concentrated under reduced pressure. The crude material was purified by flash chromatography on silica-gel, using 5% methanol in ethyl acetate.

Method D: Grignard Reaction.

To a solution of the Grignard reagent (2 eq) in dry diethyl ether the corresponding carbonyl compound (1 eq) was added dropwise. The reaction mixture was heated to reflux for 2 hours. Afterwards ice was added followed by the addition of HCl (1 M) till resulted precipitate disappeared. The phases were separated and water phase was extracted twice with diethyl ether. The combined organic layers were washed with saturated sodium hydrogen carbonate solution and brine. After drying over $MgSO_4$ and concentration under vacuum the crude product was purified by flash chromatography on silica-gel.

Method E: CDI Reaction.

To a solution of the corresponding alcohol (1 eq) in NMP or acetonitrile, CDI (5 eq) was added. Then the solution was heated to reflux for 16 hours. After cooling down to room temperature the reaction mixture was diluted with EtOAc and washed with water and brine. After drying over $MgSO_4$ and concentration under vacuum the crude product was purified by flash chromatography on silica-gel.

2-Bromo-5-(bromomethyl)pyridine (1b)

Synthesized from 2-bromo-5-methylpyridine (3.00 g, 17.40 mmol), NBS (3.41 g, 19.20 mmol) and DBPO (230 mg, 0.80 mmol) in carbon tetrachloride according to Method A. Yield: 2.56 g (59%); lachrymatory yellow needles; $^1$H NMR (CDCl$_3$, 500 MHz): $\delta_H$(ppm)=4.14 (s, 2H), 7.47 (d, J=8.2 Hz, 1H), 7.59 (d, J=8.2 Hz, 1H), 8.38 (s, 1H); MS (ESI): m/z=252.37 [M+H]$^+$.

5-Imidazol-1-ylmethyl-2-bromopyridine (1a)

Synthesized using 1b (1.32 g, 5.26 mmol), imidazole (0.75 g, 11.00 mmol), $K_2CO_3$ (1.13 g, 8.16 mmol) and 18-crown-6 according to Method B. Yellow solid. Yield: 0.75 g, 60%. $^1$H NMR (CDCl$_3$, 500 MHz): $\delta_H$ (ppm)=5.12 (s, 2H), 6.88 (t, J=1.2 Hz, 1H), 7.13 (s, 1H), 7.28 (d, J=2.5 Hz, 1H), 7.48 (d, J=8.5 Hz, 1H), 7.56 (s, 1H), 8.28 (d, J=2.5 Hz, 1H); MS (ESI): m/z=239.08 [M+H]$^+$.

5-Imidazol-1-ylmethyl-2-phenyl-pyridine (1)

Synthesized using compound 1a (0.20 g, 0.84 mmol) and phenylboronic acid (0.20 g, 1.68 mmol) according to Method B. Yellow solid. Yield: 0.10 g, 57%. $^1$H NMR (CDCl$_3$, 500 MHz): $\delta_H$ (ppm)=5.19 (s, 2H), 6.94 (t, J=1.3 Hz, 1H), 7.13 (s, 1H), 7.48-7.50 (m, 4H), 7.60 (s, 1H), 7.72 (d, J=8.2 Hz, 1H), 7.97-7.99 (m, 1H); $^{13}$C NMR (CDCl$_3$, 125 MHz): $\delta_C$ (ppm)=48.1, 119.0, 120.6, 126.9, 128.8, 130.0, 130.4, 135.7, 137.3, 138.6, 148.6, 157.7; MS (ESI): m/z=236.0 [M+H]$^+$.

4-Imidazol-1-ylmethyl-pyridine (2)

Synthesized from 4-(bromomethyl)pyridine hydrobromide (500 mg, 1.97 mmol), imidazole (538 mg, 7.90 mmol) and $K_2CO_3$ (1.36 g, 9.85 mmol) in DMF according to Method B. Yield: 212 mg, 1.35 mmol, 68%. $^1$H NMR (CDCl$_3$, 500 MHz): $\delta_H$(ppm): 5.16 (s, 2H), 6.91 (s, 1H), 7.01 (d, J=6.3 Hz, 2H), 7.14 (s, 1H), 7.69 (s, 1H), 8.57 (d, J=6.3 Hz, 2H); $^{13}$C NMR (CDCl$_3$, 125 MHz): $\delta_C$ (ppm)=49.4, 119.3, 121.4, 130.3, 147.6, 145.2, 150.4; MS (ESI): m/z=160.08 [M+H]$^+$.

3-Imidazol-1-ylmethyl-pyridine (3)

Synthesized from 3-(Bromomethyl)pyridine hydrobromide (500 mg, 1.97 mmol), imidazole (538 mg, 7.90 mmol) and $K_2CO_3$ (1.36 g, 9.85 mmol) in DMF according to Method B. Yield: 246 mg, 1.55 mmol, 78%. $^1$H NMR (CDCl$_3$, 500 MHz): $\delta_H$(ppm): 5.15 (s, 2H), 6.90 (d, J=0.9 Hz, 1H), 7.11 (d, J=0.9 Hz, 1H), 7.29 (dd, J=7.9, 4.7 Hz, 1H), 7.40-7.43 (m, 1H), 7.56 (bs, 1H), 8.52-8.53 (m, 1H), 8.59 (d, J=4.7 Hz, 1H); $^{13}$C NMR (CDCl$_3$, 125 MHz): $\delta_C$ (ppm)=48.3, 119.0, 123.8, 130.3, 131.8, 134.8, 137.3, 148.7, 149.9; MS (ESI): m/z=160.07 [M+H]$^+$.

3-Bromomethyl-pyridine-2-carbonitrile (4a)

Synthesized from 3-methylpicolinonitrile (1.00 g, 8.47 mmol), NBS (1.66 g, 9.31 mmol) and DBPO (103 mg, 0.42 mmol) in CCl$_4$ according to Method A. Yield: 616 mg, 3.12 mmol, 37%. $^1$H NMR (CDCl$_3$, 500 MHz): $\delta_H$ (ppm): 4.63 (s, 2H), 7.54 (dd, J=7.9, 4.9 Hz, 1H), 7.92 (dd, J=7.9, 1.5 Hz, 1H), 8.64 (dd, J=4.9, 1.5 Hz, 1H); $^{13}$C NMR (CDCl$_3$, 125 MHz): $\delta_C$ (ppm)=26.8, 115.2, 127.1, 133.2, 138.1, 138.3, 150.5; MS (ESI): m/z=199.79 [M+H]$^+$.

3-Imidazol-1-ylmethyl-pyridine-2-carbonitrile (4)

Synthesized from 4a (600 mg, 3.04 mmol), imidazole (829 mg, 12.1 mmol) and K$_2$CO$_3$ (2.07 g, 15.0 mmol) in DMF according to Method A. Yield: 476 mg, 2.58 mmol, 85%. $^1$H NMR (CDCl$_3$, 500 MHz): $\delta_H$ (ppm): 5.41 (s, 2H), 6.97 (t, J=1.3 Hz, 1H), 7.15 (t, J=1.3 Hz, 1H), 7.36-7.38 (m, 1H), 7.51 (dd, J=8.2, 4.7 Hz, 1H), 7.63 (s, 1H), 8.68 (dd, J=4.7, 1.6 Hz, 1H); $^{13}$C NMR (CDCl$_3$, 125 MHz): $\delta_C$ (ppm)=47.1, 115.3, 119.1, 127.4, 130.9, 132.5, 135.6, 137.0, 137.5, 150.7; MS (ESI): m/z=185.08 [M+H]$^+$.

2-Bromo-3-bromomethyl-pyridine (5a)

Synthesized from 2-bromo-3-methylpyridine (5.00 g, 29.1 mmol), NBS (5.69 g, 32.0 mmol) and DBPO (352 mg, 1.46 mmol) in CCl$_4$ according to Method A. Yield: 2.87 g, 11.4 mmol, 39%. This compound was directly used in the next step without further purification.

2-Bromo-3-imidazol-1-ylmethyl-pyridine (5)

Synthesized from 5a (891 mg, 2.78 mmol), imidazole (658 mg, 5.56 mmol) and K$_2$CO$_3$ (1.92 g, 13.9 mmol) according to Method B. Yield: 375 mg, 1.41 mmol, 51%. $^1$H NMR (CDCl$_3$, 500 MHz): $\delta_H$ (ppm): 5.23 (s, 2H), 6.96 (t, J=1.3 Hz, 1H), 7.07 (d, J=7.6 Hz, 1H) 7.15 (t, J=1.3 Hz, 1H), 7.24 (dd, J=7.6, 4.7 Hz, 1H), 7.66 (brs, 1H), 8.32 (dd, J=4.7, 1.9 Hz, 1H); $^{13}$C NMR (CDCl$_3$, 125 MHz): $\delta_C$ (ppm)=49.7, 119.3, 123.4, 130.0, 133.4, 136.6, 137.6, 142.0, 149.7; MS (ESI): m/z=239.10 [M+H]$^+$.

3-Bromo-5-bromomethyl-2-chloro-pyridine (6a)

Synthesized from 3-bromo-2-chloro-5-methylpyridine (4.00 g, 19.3 mmol), NBS (3.79 g, 21.3 mmol) and DBPO (233 mg, 0.97 mmol) in CCl$_4$ according to Method A. Yield: 2.38 g, 8.34 mmol, 43%. This compound was directly used in the next step without further purification.

3-Bromo-2-chloro-5-imidazol-1-ylmethyl-pyridine (6)

Synthesized from 6a (2.38 g, 8.34 mmol), imidazole (1.14 g, 16.7 mmol) and K$_2$CO$_3$ (5.76 g, 41.7 mmol) according to Method B. Yield: 1.88 g, 6.90 mmol, 83%. $^1$H NMR (CDCl$_3$, 500 MHz): $\delta_H$ (ppm): 5.14 (s, 2H), 6.89 (bs, 1H), 7.13 (d, J=4.0 Hz, 1H), 7.61-7.63 (m, 1H), 7.70 (brs, 1H), 8.20 (brs, 1H); $^{13}$C NMR (CDCl$_3$, 125 MHz): $\delta_C$ (ppm)=46.8, 118.9, 120.8, 130.5, 132.2, 137.2, 140.8, 146.3, 150.9; MS (ESI): m/z=272.05 [M+H]$^+$.

2-(2-Fluoro-phenyl)-5-imidazol-1-ylmethyl-pyridine (7)

Synthesized using 2-fluorophenylboronic acid (176 mg, 1.26 mmol) and 1a (150 mg, 0.63 mmol) according to Method C. Yellow solid. Yield: 112 mg, 0.44 mmol, 70%. $^1$H NMR (500 MHz, CDCl$_3$): $\delta_H$ (ppm): 5.18 (s, 2H), 6.93 (t, J=1.3 Hz, 1H), 7.12 (bs, 1H), 7.15 (ddd, J=11.7, 8.2, 1.3 Hz, 1H), 7.26 (dt, J=7.9, 1.3 Hz, 1H), 7.36-7.40 (m, 1H), 7.48 (dd, J=8.2, 2.5 Hz, 1H), 7.59 (s, 1H), 7.78 (ddd, J=8.2, 2.2, 0.9 Hz, 1H), 7.97 (dt, J=7.9, 1.9 Hz, 1H), 8.60 (dd, J=2.5, 0.6 Hz, 1H); $^{13}$C NMR (CDCl$_3$, 125 MHz): $\delta_C$ (ppm)=48.1, 116.2 (d, J=23.0 Hz), 119.0, 124.5 (d, J=9.1 Hz), 124.6, 126.6, 126.7, 130.0 (d, J=9.1 Hz), 130.7 (d, J=9.1 Hz), 130.9 (d, J=2.7 Hz), 135.3, 137.3, 148.5, 153.6 (d, J=2.7 Hz), 160.4 (d, J=250.2 Hz); MS (ESI): m/z=254.18 [M+H]$^+$.

2-(3-Fluoro-phenyl)-5-imidazol-1-ylmethyl-pyridine (8)

Synthesized using 3-fluorophenylboronic acid (230 mg, 1.68 mmol) and 1a (200 mg, 0.84 mmol) according to Method C. Yellow solid. Yield: 135 mg, 0.53 mmol, 64%. $^1$H NMR (CDCl$_3$, 500 MHz): $\delta_H$ (ppm): 5.19 (s, 2H), 6.93 (s, 1H), 7.11 (ddd, J=8.2, 2.5, 0.9 Hz, 1H), 7.13 (dd, J=2.5, 0.9 Hz, 1H), 7.43 (ddd, J=8.2, 7.9, 6.0 Hz, 1H), 7.50 (dd, J=8.2, 2.5 Hz, 1H), 7.59 (brs, 1H), 7.69-7.76 (m, 3H), 8.58 (dd, J=2.2, 0.6 Hz, 1H); $^{13}$C NMR (CDCl$_3$, 125 MHz): $\delta_C$ (ppm)=48.0, 113.9 (d, J=23.0 Hz), 116.1 (d, J=21.1 Hz), 119.0, 120.6, 122.4 (d, J=2.9 Hz), 130.3 (d, J=7.6 Hz), 130.4, 130.7, 135.8, 137.3, 140.8 (d, J=7.6 Hz), 148.6, 156.3 (d, J=2.9 Hz), 163.5 (d, J=245.7 Hz); MS (ESI): m/z=254.13 [M+H]$^+$.

2-(4-Fluoro-phenyl)-5-imidazol-1-ylmethyl-pyridine (9)

Synthesized using 4-fluorophenylboronic acid (230 mg, 1.68 mmol) and 1a (200 mg, 0.84 mmol) according to Method C. Yellow solid. Yield: 160 mg, 0.63 mmol, 75%. $^1$H NMR (CDCl$_3$, 500 MHz): $\delta_H$ (ppm)=5.18 (s, 2H), 6.92 (s, 1H), 7.12 (brs, 1H), 7.15 (t, J=8.8 Hz, 2H), 7.48 (dd, J=8.2, 2.2 Hz, 1H), 7.60 (s, 1H), 7.67 (d, J=8.2 Hz, 1H), 7.97 (dd, J=8.8, 5.4 Hz, 2H), 8.57 (d, J=1.9 Hz, 1H); $^{13}$C NMR (CDCl$_3$, 125 MHz): $\delta_C$ (ppm)=48.1, 115.7 (d, J=22.1 Hz), 119.0, 120.2, 128.7 (d, J=8.6 Hz), 130.0, 130.4, 134.7 (d, J=3.9 Hz), 135.8, 137.3, 148.6, 156.6, 163.7 (d, J=249.5 Hz); MS (ESI): m/z=254.18 [M+H]$^+$.

2-(3,4-Difluoro-phenyl)-5-imidazol-1-ylmethyl-pyridine (10)

Synthesized using 3,4-difluorophenylboronic acid (270 mg, 1.68 mmol) and 1a (200 mg, 0.84 mmol) according to Method C. Yellow solid. Yield: 210 mg, 0.77 mmol, 92%. $^1$H NMR (CDCl$_3$, 500 MHz): $\delta_H$ (ppm)=5.18 (s, 2H), 6.92 (t, J=1.3 Hz, 1H), 7.13 (t, J=1.3 Hz, 1H), 7.25 (ddd, J=9.8, 8.5, 8.2 Hz, 1H), 7.49 (dd, J=8.2, 2.5 Hz, 1H), 7.59 (s, 1H), 7.66 (dd, J=8.3, 0.6 Hz, 1H), 7.69-7.73 (m, 1H), 7.86 (ddd, J=11.4, 7.6, 2.2 Hz, 1H), 8.56 (dd, J=2.3, 0.6 Hz, 1H); $^{13}$C NMR (CDCl$_3$, 125 MHz): $\delta_C$ (ppm)=48.0, 116.0 (d, J=18.2 Hz), 117.6 (d, J=17.3 Hz), 119.0, 120.2, 122.8 (dd, J=3.8, 6.7 Hz), 130.4, 130.6, 135.6 (dd, J=3.8, 5.8 Hz), 135.9, 137.3, 148.6, 150.8 (dd, J=20.2, 255.3 Hz), 151.3 (dd, J=15.4, 254.3 Hz), 155.3; MS (ESI): m/z=272.10 [M+H]$^+$.

2-Fluoro-4-(5-imidazol-1-ylmethyl-pyridin-2-yl)-phenol (11)

Synthesized using 3-fluoro-4-hydroxyphenylboronic acid (196 mg, 2.00 mmol) and 1a (150 mg, 0.63 mmol) according to Method C. Yellow solid. Yield: 40 mg, 0.15 mmol, 24%. $^1$H NMR (500 MHz, DMSO-d$_6$): $\delta_H$ (ppm): 5.25 (s, 2H), 6.92 (brs, 1H), 7.03 (t, J=8.8 Hz, 1H), 7.25 (t, J=1.2 Hz, 1H), 7.69 (dd, J=8.2, 2.2 Hz, 1H), 7.74 (ddd, J=8.5, 2.2, 0.6 Hz, 1H), 7.80 (brs, 1H), 7.83 (dd, J=13.0, 2.2 Hz, 1H), 7.87 (dd, J=8.2, 0.6 Hz, 1H), 8.57 (dd, J=2.2, 0.6 Hz, 1H), 10.2 (s, 1H); MS (ESI): m/z=270.12 [M+H]⁺.

5-Imidazol-1-ylmethyl-2-(2-methoxy-phenyl)pyridine (12)

Synthesized using 2-methoxyphenylboronic acid (190 mg, 1.68 mmol) and 1a (200 mg, 0.84 mmol) according to Method C. Yellow solid. Yield: 210 mg, 0.79 mmol, 94%. ¹H NMR (CDCl₃, 500 MHz): $\delta_H$ (ppm)=3.85 (s, 3H), 5.17 (s, 2H), 6.95 (brs, 1H), 7.00 (dd, J=8.5, 0.6 Hz, 1H), 7.08 (dt, J=7.6, 1.1 Hz, 1H), 7.12 (s, 1H), 7.38 (ddd, J=8.5, 7.6, 1.9 Hz, 1H), 7.44 (dd, J=8.5, 2.2 Hz, 1H), 7.60 (s, 1H), 7.77 (dd, J=7.6, 1.9 Hz, 1H), 7.83 (d, J=8.2 Hz, 1H), 8.60 (d, J=1.6 Hz, 1H); ¹³C NMR (CDCl₃, 125 MHz): $\delta_C$ (ppm)=48.2, 55.6, 111.4, 119.1, 121.1, 125.2, 128.3, 129.5, 130.2, 130.3, 131.1, 134.6, 137.3, 148.2, 156.4, 157.0; MS (ESI): m/z=266.28 [M+H]⁺.

5-Imidazol-1-ylmethyl-2-(4-methoxy-phenyl)pyridine (13)

Synthesized using 4-methoxyphenylboronic acid (380 mg, 3.35 mmol) and 1a (400 mg, 1.68 mmol) according to Method C. Yellow solid. Yield: 400 mg, 1.51 mmol, 90%. ¹H NMR (CDCl₃, 500 MHz): $\delta_H$ (ppm)=3.86 (s, 3H), 5.16 (s, 2H), 6.92 (t, J=1.3 Hz, 1H), 6.99 (d, J=9.1 Hz, 2H), 7.11 (s, 1H), 7.46 (dd, J=8.2, 2.5 Hz, 1H), 7.59 (s, 1H), 7.66 (d, J=8.2 Hz, 1H), 7.94 (d, J=9.1 Hz, 2H), 8.54 (d, J=2.5 Hz, 1H); ¹³C NMR (CDCl₃, 125 MHz): $\delta_C$ (ppm)=48.1, 55.4, 114.2, 119.0, 119.8, 128.2, 129.2, 130.3, 131.2, 135.7, 137.3, 148.5, 157.4, 160.8; MS (ESI): m/z=266.22 [M+H]⁺.

2-(3,4-Dimethoxy-phenyl)-5-imidazol-1-ylmethyl-pyridine (14)

Synthesized using 3,4-dimethoxyphenylboronic acid (610 mg, 3.36 mmol) and 1a (400 mg, 1.68 mmol) according to Method C. Yellow solid. Yield: 470 mg, 1.58 mmol, 94%. ¹H NMR (CDCl₃, 500 MHz): $\delta_H$ (ppm)=3.93 (s, 3H), 3.98 (s, 3H), 5.16 (s, 2H), 6.92 (br, s, 1H), 6.94 (d, J=8.5 Hz, 1H), 7.11 (bs, 1H), 7.46 (dd, J=8.5, 2.2 Hz, 1H), 7.47 (dd, J=8.5, 2.2 Hz, 1H), 7.58 (bs, 1H), 7.65 (d, J=2.2 Hz, 1H), 7.67 (d, J=8.5 Hz, 1H), 8.54 (d, J=2.2 Hz, 1H); ¹³C NMR (CDCl₃, 125 MHz): $\delta_C$ (ppm)=48.1, 56.0, 56.0, 113.3, 110.0, 111.1, 119.0, 119.5, 120.0, 129.4, 130.3, 131.4, 135.7, 148.4, 149.4, 150.3, 157.3; MS (ESI): m/z=296.17 [M+H]⁺.

2-(5-Imidazol-1-ylmethyl-pyridin-2-yl)-phenylamine (15)

Synthesized using 2-aminophenylboronic acid (173 g, 1.26 mmol) and 1a (150 mg, 0.63 mmol) according to Method C. Yellow solid. Yield: 120 mg, 0.48 mmol, 76%. ¹H NMR (500 MHz, CDCl₃): $\delta_H$ (ppm): 5.17 (s, 2H), 6.74-6.79 (m, 2H), 6.93 (t, J=1.3 Hz, 1H), 7.13 (bs, 1H), 7.16-7.19 (m, 1H), 7.49-7.53 (m, 2H), 7.62 (s, 1H), 7.66 (d, J=8.2 Hz, 1H). 8.48 (d, J=1.8 Hz, 1H); ¹³C NMR (CDCl₃, 125 MHz): $\delta_C$ (ppm)=48.2, 117.3, 117.6, 119.1, 121.1, 122.2, 128.7, 129.3, 130.2, 130.3, 135.8, 137.3, 146.6, 146.7, 159.7; MS (ESI): m/z=250.71 [M+H]⁺.

3-(5-Imidazol-1-ylmethyl-pyridin-2-yl)-phenylamine (16)

Synthesized using 3-aminophenylboronic acid 230 mg, 1.68 mmol) and 1a (200 mg, 0.84 mmol) according to Method C. Orange solid. Yield: 144 mg, 0.56 mmol, 67%. ¹H NMR (CDCl₃, 500 MHz): $\delta_H$ (ppm)=5.11 (s, 2H), 6.72 (ddd, J=7.6, 2.4, 0.9 Hz, 1H), 6.89 (brs, 1H), 7.08 (bs, 1H), 7.21 (t, J=7.7 Hz, 1H), 7.28 (dt, J=7.8, 1.3 Hz, 1H), 7.33 (t, J=2.2 Hz, 1H), 7.41 (dd, J=8.2, 2.2 Hz, 1H), 7.55 (brs, 1H), 7.62 (d, J=8.2 Hz, 1H), 8.50 (d, J=2.2 Hz, 1H); ¹³C NMR (CDCl₃, 125 MHz): $\delta_C$ (ppm)=48.0, 113.3, 116.0, 117.0, 119.0, 120.5, 129.6, 129.9, 130.1, 135.6, 137.2, 139.5, 146.9, 148.3, 157.6; MS (ESI): m/z=251.13 [M+H]⁺.

4-(5-Imidazol-1-ylmethyl-pyridin-2-yl)-phenylamine (17)

Synthesized using 4-aminophenylboronic acid (173 mg, 1.26 mmol) and 1a (150 mg, 0.63 mmol) according to Method C. White solid. Yield: 35 mg, 0.14 mmol, 22%. ¹H NMR (500 MHz, CDCl₃): $\delta_H$ (ppm): 5.14 (s, 2H), 6.76 (d, J=8.5 Hz, 2H), 6.92 (s, 1H), 6.93 (brs, 1H), 7.12 (s, 1H), 7.43 (dd, J=8.5, 2.5 Hz, 1H), 7.60 (brs, 1H), 7.62 (d, J=8.5 Hz, 1H), 7.82 (d, J=8.5 Hz, 2H), 8.52 (d, J=1.5 Hz, 1H); MS (ESI): m/z=250.74 [M+H]⁺.

5-(5-Imidazol-1-ylmethyl-pyridin-2-yl)-2-methyl-phenylamine (18)

Synthesized using 3-amino-4-methylphenylboronic acid (190 mg, 1.26 mmol) and 1a (150 mg, 0.63 mmol) according to Method C. Yellow solid. Yield: 139 mg, 0.52 mmol, 84%. ¹H NMR (500 MHz, CDCl₃): $\delta_H$ (ppm): 2.22 (s, 3H), 5.16 (s, 2H), 6.92 (t, J=0.9 Hz, 1H), 7.12 (t, J=0.9 Hz, 1H), 7.13 (d, J=7.9 Hz, 1H), 7.26 (dd, J=7.9, 1.9 Hz, 1H), 7.37 (d, J=1.9 Hz, 1H), 7.45 (dd, J=8.2, 2.2 Hz, 1H), 7.59 (s, 1H), 7.67 (dd, J=8.2, 0.6 Hz, 1H), 8.55 (dd, J=2.2, 0.6 Hz, 1H); ¹³C NMR (CDCl₃, 125 MHz): $\delta_C$ (ppm)=17.2, 48.2, 113.2, 117.1, 119.0, 120.4, 123.9, 129.6, 130.2, 130.9, 135.6, 137.3, 137.4, 145.1, 148.4, 157.8; MS (ESI): m/z=264.25 [M+H]⁺.

3-(5-Imidazol-1-ylmethyl-pyridin-2-yl)-benzonitrile (19)

Synthesized using 3-cyanophenylboronic acid (185 mg, 1.26 mmol) and 1a (150 mg, 0.63 mmol) according to Method C. Yellow solid. Yield: 135 mg, 0.52 mmol, 82%. ¹H NMR (CDCl₃, 500 MHz): $\delta_H$ (ppm): 5.21 (s, 2H), 6.94 (s, 1H), 7.13 (s, 1H), 7.54 (dd, J=8.2, 2.4 Hz, 1H), 7.55-7.60 (m, 2H), 7.70 (d, J=7.9 Hz, 1H), 7.73 (d, J=8.2 Hz, 1H), 8.21 (d, J=7.9 Hz, 1H), 8.31 (s, 1H), 8.61 (d, J=1.5 Hz, 1H); ¹³C NMR (CDCl₃, 125 MHz): $\delta_C$ (ppm)=48.0, 113.1, 118.6, 119.0, 120.6, 129.7, 130.4, 130.6, 131.0, 131.3, 132.5, 136.0, 137.3, 139.6, 148.77, 148.81, 155.1; MS (ESI): m/z=261.41 [M+H]⁺.

4-(5-Imidazol-1-ylmethyl-pyridin-2-yl)-benzonitrile (20)

Synthesized using 4-cyanophenylboronic acid (185 mg, 1.26 mmol) and 1a (150 mg, 0.63 mmol) according to Method C. Yellow solid. Yield: 110 mg, 0.42 mmol, 67%. ¹H NMR (CDCl₃, 500 MHz): $\delta_H$ (ppm): 5.22 (s, 2H), 6.93 (s, 1H), 7.14 (s, 1H), 7.54 (dd, J=8.2, 2.3 Hz, 1H), 7.60 (s, 1H), 7.75-7.78 (m, 3H), 8.11 (d, J=8.2 Hz, 2H), 8.62 (s, 1H); ¹³C NMR (CDCl₃, 125 MHz): $\delta_C$ (ppm)=48.0, 112.9, 118.6, 119.0, 121.0, 127.4, 130.5, 131.5, 132.6, 136.0, 137.3, 142.6, 148.8, 150.4; MS (ESI): m/z=261.03 [M+H]⁺.

4-(5-Imidazol-1-ylmethyl-pyridin-2-yl)-benzaldehyde (21)

Synthesized using 4-formylphenylboronic acid (252 mg, 1.68 mmol) and 1a (200 mg, 0.84 mmol) according to Method C. Brown solid. Yield: 150 mg, 0.57 mmol, 68%. $^1$H NMR (CDCl$_3$, 500 MHz): $\delta_H$ (ppm): 5.21 (s, 2H), 6.94 (t, J=1.3 Hz, 1H), 7.14 (t, J=0.9 Hz, 1H), 7.53 (dd, J=8.2, 2.0 Hz, 1H), 7.60 (brs, 1H), 7.79 (dd, J=8.2, 0.6 Hz, 1H), 7.98 (d, J=8.4 Hz, 2H), 8.16 (d, J=8.4 Hz, 2H), 8.63 (d, J=2.0 Hz, 1H), 10.08 (s, 1H); $^{13}$C NMR (CDCl$_3$, 125 MHz): $\delta_C$ (ppm)=48.0, 119.0, 121.2, 127.5, 130.2, 130.5, 131.3, 135.9, 136.7, 137.3, 144.0, 148.8, 156.1, 191.8; MS (ESI): m/z=264.16 [M+H]$^+$.

[4-(5-Imidazol-1-ylmethyl-pyridin-2-yl)-phenyl]-diphenyl-amine (22)

Synthesized using 4-(diphenylamino)phenylboronic acid (364 mg, 1.26 mmol) and 1a (150 mg, 0.63 mmol) according to Method C. Yellow solid. Yield: 140 mg, 0.34 mmol, 55%. $^1$H NMR (500 MHz, CDCl$_3$): $\delta_H$ (ppm): 5.16, (s, 2H), 6.93 (t, J=1.3 Hz, 1H), 7.06 (tt, J=7.3, 1.3 Hz, 2H), 7.12-7.15 (m, 7H), 7.25-7.29 (m, 4H), 7.45 (dd, J=8.2, 2.2 Hz, 1H), 7.58 (br, s, 1H), 7.65 (dd, J=8.2, 0.6 Hz, 1H), 7.83-7.86 (m, 2H), 8.54 (dd, J=2.5, 0.6 Hz, 1H); $^{13}$C NMR (CDCl$_3$, 125 MHz): $\delta_C$ (ppm)=48.2, 119.0, 119.8, 122.8, 123.4, 124.9, 127.7, 129.2, 129.3, 130.2, 132.0, 135.7, 137.3, 147.3, 148.5, 149.1, 157.3; MS (ESI): m/z=402.94 [M+H]$^+$.

5-Imidazol-1-ylmethyl-2-naphthalen-1-yl-pyridine (23)

Synthesized using 1-naphthylboronic acid (217 mg, 1.26 mmol) and 1a (150 mg, 0.63 mmol) according to Method C. Yellow solid. Yield: 130 mg, 0.46 mmol, 72%. $^1$H NMR (500 MHz, CDCl$_3$): $\delta_H$ (ppm): 5.25 (s, 2H), 7.00 (t, J=1.3 Hz, 1H), 7.16 (t, J=1.3 Hz, 1H), 7.46-7.52 (m, 2H), 7.54-7.60 (m, 4H), 7.65 (br, s, 1H), 7.90-7.93 (m, 2H), 8.03-8.05 (m, 1H), 8.70 (dd, J=2.5, 0.9 Hz, 1H); $^{13}$C NMR (CDCl$_3$, 125 MHz): $\delta_C$ (ppm)=48.19, 119.1, 125.2, 125.2, 125.3, 126.0, 126.6, 127.6, 128.4, 129.2, 130.1, 130.3, 131.0, 135.3, 137.3, 137.6, 148.3, 159.5; MS (ESI): m/z=286.05 [M+H]$^+$.

5-Imidazol-1-ylmethyl-2-naphthalen-2-yl-pyridine (24)

Synthesized using 2-naphthylboronic acid (217 g, 1.26 mmol) and 1a (150 mg, 0.63 mmol) according to Method C. Yellow solid. Yield: 118 mg, 0.41 mmol, 66%. $^1$H NMR (CDCl$_3$, 500 MHz): $\delta_H$ (ppm): 5.23 (s, 2H), 6.97 (s, 1H), 7.17 (s, 1H), 7.50-7.53 (m, 2H), 7.57 (dd, J=8.2, 2.4 Hz, 1H), 7.85-7.88 (m, 3H), 7.95 (d, J=8.8 Hz, 2H), 8.11 (dd, J=8.5, J=1.8 Hz, 1H), 8.47 (d, J=0.9 Hz, 1H), 8.65 (d, J=1.8 Hz, 1H); $^{13}$C NMR (CDCl$_3$, 125 MHz): $\delta_C$ (ppm)=48.4, 119.2, 120.9, 124.3, 126.4, 126.5, 126.8, 127.7, 128.6, 128.7, 129.3, 129.8, 133.4, 133.8, 135.7, 136.0, 137.2, 148.7; MS (ESI): m/z=285.92 [M+H]$^+$.

5-Imidazol-1-ylmethyl-2,3-diphenyl-pyridine (25)

Synthesized using phenylboronic acid (134 mg, 1.10 mmol) and 6 (150 mg, 0.55 mmol) according to Method C. Yellow solid. Yield: 79 mg, 0.25 mmol, 46%. $^1$H NMR (500 MHz, CDCl$_3$): $\delta_H$ (ppm): 5.27 (s, 2H), 7.00 (brs, 1H), 7.11-7.13 (m, 2H), 7.16 (brs, 1H), 7.21-7.28 (m, 6H), 7.32-7.34 (m, 2H), 7.49 (d, J=2.1 Hz, 1H), 8.60 (d, J=2.1 Hz, 1H); $^{13}$C NMR (CDCl$_3$, 125 MHz): $\delta_C$ (ppm)=48.3, 119.2, 127.6, 128.0, 128.1, 128.4, 129.2, 129.4, 129.8, 136.4, 137.1, 137.5, 139.0, 139.3, 147.1, 147.1, 157.6; MS (ESI): m/z=312.10 [M+H]$^+$.

5-Imidazol-1-ylmethyl-[2,3']bipyridinyl (26)

Synthesized using 3-pyridylboronic acid (206 mg, 1.68 mmol) and 1a (200 mg, 0.84 mmol) according to Method C. Yellow solid. Yield: 144 mg, 0.61 mmol, 73%. $^1$H NMR (CDCl$_3$, 500 MHz): $\delta_H$ (ppm): 5.20 (s, 2H), 6.93 (t, J=1.5 Hz, 1H), 7.13 (t, J=0.9 Hz, 1H), 7.40 (ddd, J=7.9, 4.7, 0.9 Hz, 1H), 7.52 (dd, J=8.2, 2.2 Hz, 1H), 7.60 (s, 1H), 7.75 (d, J=8.2 Hz), 8.29-8.32 (m, 1H), 8.61 (m, 1H), 8.66 (dd, J=4.7, 1.5 Hz, 1H); $^{13}$C NMR (CDCl$_3$, 125 MHz): $\delta_C$ (ppm)=48.0, 119.0, 120.6, 123.6, 130.5, 131.0, 134.0, 134.3, 135.9, 137.3, 148.2, 148.9, 150.3, 155.0. MS (ESI): m/z=237.03 [M+H]$^+$.

5-Imidazol-1-ylmethyl-[2,4']bipyridinyl (27)

Synthesized using 4-pyridylboronic acid (123 mg, 1.00 mmol) and 1a (95 mg, 0.4 mmol) according to Method C. Yellow solid. Yield: 73 mg, 77%. $^1$H NMR (500 MHz, CDCl$_3$): $\delta_H$ (ppm): 5.22 (s, 2H), 6.94 (t, J=1.3 Hz, 1H), 7.14 (brs, 1H), 7.54 (dd, J=2.5, 8.2 Hz, 1H), 7.60 (s, 1H), 7.80 (d, J=8.2 Hz, 1H), 7.88 (dd, J=1.6, 4.1 Hz, 2H), 8.64 (dd, J=0.6, 2.5 Hz, 1H), 8.73 (dd, J=1.6, 4.4 Hz, 2H); $^{13}$C NMR (CDCl$_3$, 125 MHz): $\delta_C$ (ppm)=48.3, 119.3, 121.2, 130.8, 132.3, 136.2, 137.6, 149.1, 150.8, 155.1; MS (ESI): m/z=237.02 [M+H]$^+$.

5-(5-Imidazol-1-ylmethyl-pyridin-2-yl)-pyrimidine (28)

Synthesized using pyrimid-5-ylboronic acid (155 mg, 1.26 mmol) and 1a (150 mg, 0.63 mmol) according to Method C. Yellow solid. Yield: 121 mg, 0.51 mmol, 81%. $^1$H NMR (500 MHz, CDCl$_3$): $\delta_H$ (ppm): 5.23 (s, 2H), 6.93 (t, J=1.3 Hz, 1H), 7.12 (t, J=1.3 Hz, 1H), 7.57 (dd, J=8.2, 2.5 Hz, 1H), 7.67 (s, 1H), 7.74 (dd, J=8.2, 0.9 Hz, 1H), 8.62 (m, 1H), 9.23 (s, 1H), 9.29 (s, 2H); $^{13}$C NMR (CDCl$_3$, 125 MHz): $\delta_C$ (ppm)=48.0, 119.0, 120.5, 130.1, 131.6, 131.8, 136.1, 137.3, 149.2, 152.1, 155.0, 158.8; MS (ESI): m/z=238.10 [M+H]$^+$.

5-Imidazol-1-ylmethyl-6'-methoxy-[2,3']bipyridinyl (29)

Synthesized using 2-methoxy-5-pyrid-5-ylboronic acid (193 mg, 1.26 mmol) and 1a (150 mg, 0.63 mmol) according to Method C. Yellow solid. Yield: 136 mg, 0.51 mmol, 81%. $^1$H NMR (CDCl$_3$, 500 MHz): $\delta_H$ (ppm): 3.97 (s, 3H), 5.16 (s, 2H), 6.81 (d, J=8.5 Hz, 1H), 6.92 (brs, 1H), 7.11 (s, 1H), 7.46 (dd, J=8.2, 2.4 Hz, 1H), 7.62-7.64 (m, 2H), 8.20 (dd, J=8.5, 2.4 Hz, 1H), 8.53 (d, J=1.8 Hz, 1H), 8.72 (d, J=2.1 Hz, 1H); $^{13}$C NMR (CDCl$_3$, 125 MHz): $\delta_C$ (ppm)=48.1, 53.64, 110.9, 119.0, 119.7, 127.7, 129.8, 130.0, 135.8, 137.2, 137.3, 145.6, 148.7, 155.2, 164.8; MS (ESI): m/z=266.66 [M+H]$^+$.

4-(5-Imidazol-1-ylmethyl-pyridin-2-yl)-isoquinoline (30)

Synthesized using 4-isoquinolinylboronic acid (218 mg, 1.26 mmol) and 1a (150 mg, 0.63 mmol) according to Method C. Yellow solid. Yield: 97 mg, 0.34 mmol, 54%. $^1$H NMR (CDCl$_3$, 500 MHz): $\delta_H$ (ppm): 5.26 (s, 2H), 7.00 (t, J=1.3 Hz, 1H), 7.16 (brs, 1H), 7.58-7.66 (m, 4H), 7.70-7.73 (m, 1H), 8.04 (d, J=8.2 Hz, 1H), 8.17 (dd, J=8.5, 0.6 Hz, 1H), 8.62 (s, 1H), 8.71 (d, J=1.6 Hz, 1H), 9.30 (s, 1H); $^{13}$C NMR (CDCl$_3$, 125 MHz): $\delta_C$ (ppm)=48.1, 119.1, 124.5, 125.0, 127.4, 128.0, 128.5, 130.0, 130.4, 130.8, 131.1, 133.6, 135.7, 137.4, 143.5, 148.5, 153.4, 156.6; MS (ESI): m/z=287.10 [M+H]$^+$.

5-Imidazol-1-ylmethyl-2-thiophen-2-yl-pyridine (31)

Synthesized using 2-thiophenylboronic acid (118 g, 0.92 mmol) and 1a (110 mg, 0.46 mmol) according to Method C. Yellow solid. Yield: 101 mg, 0.42 mmol, 91%. $^1$H NMR (CDCl$_3$, 500 MHz): δ$_H$ (ppm): 5.13 (s, 2H), 6.90 (s, 1H), 7.11 (t, J=4.4 Hz, 2H), 7.41-7.43 (m, 2H), 7.57-7.59 (m, 2H), 7.63 (d, J=8.2 Hz, 1H), 8.45 (d, J=1.9 Hz, 1H); $^{13}$C NMR (CDCl$_3$, 125 MHz): δ$_C$ (ppm)=48.1, 118.9, 119.0, 125.1, 128.13, 128.14, 129.8, 130.3, 135.7, 137.3, 144.0, 148.4, 152.9; MS (ESI): m/z=242.10 [M+H]$^+$.

5-Imidazol-1-ylmethyl-2-thiophen-3-yl-pyridine (32)

Synthesized using 3-thiophenylboronic acid (206 mg, 1.68 mmol) and 1a (200 mg, 0.84 mmol) according to Method C. Brown solid. Yield: 144 mg, 0.61 mmol, 73%. $^1$H NMR (CDCl$_3$, 500 MHz): δ$_H$ (ppm): 5.15 (s, 2H), 6.91 (t, J=1.3 Hz, 1H), 7.12 (s, 1H), 7.40 (dd, J=5.0, 3.2 Hz, 1H), 7.45 (dd, J=8.2, 2.2 Hz, 1H), 7.58 (s, 1H), 7.60 (dd, J=8.2, 0.6 Hz, 1H), 7.64 (dd, J=5.0, 1.3 Hz, 1H), 7.91 (dd, J=3.2, 1.3 Hz, 1H), 8.51 (dd, J=2.2, 0.6 Hz, 1H); $^{13}$C NMR (CDCl$_3$, 125 MHz): δ$_C$ (ppm)=48.1, 119.0, 120.3, 124.4, 126.1, 126.5, 129.6, 130.3, 135.7, 137.3, 141.4, 148.6, 153.8; MS (ESI): m/z=242.03 [M+H]$^+$.

2-(5-Chloro-thiophen-2-yl)-5-imidazol-1-ylmethyl-pyridine (33)

Synthesized using 5-chloro-2-thiophenylboronic acid (205 mg, 1.26 mmol) and 1a (150 mg, 0.63 mmol) according to Method C. Yellow solid. Yield: 83 mg, 0.30 mmol, 47%. $^1$H NMR (CDCl$_3$, 500 MHz): δ$_H$ (ppm): 5.17 (s, 2H), 6.91-6.92 (m, 2H), 7.13 (s, 1H), 7.33 (d, J=4.0 Hz, 1H), 7.46 (dd, J=8.2, 2.1 Hz, 1H), 7.55 (d, J=8.2 Hz, 1H), 7.80 (s, 1H), 8.42 (d, J=1.5 Hz, 1H); $^{13}$C NMR (CDCl$_3$, 125 MHz): δ$_C$ (ppm)=48.3, 118.16, 119.1, 124.2, 127.3, 129.5, 129.8, 133.1, 135.9, 137.2, 142.5, 148.5, 152.1; MS (ESI): m/z=275.98 [M+H]$^+$.

5-(5-Imidazol-1-ylmethyl-pyridin-2-yl)-thiophene-2-carbaldehyde (34)

Synthesized using 5-formyl-2-thiophenylboronic acid (197 mg, 1.26 mmol) and 1a (150 mg, 0.63 mmol) according to Method C. Yellow solid. Yield: 78 mg, 0.28 mmol, 46%. $^1$H NMR (500 MHz, CDCl$_3$): δ$_H$ (ppm): 5.18 (s, 2H), 6.92 (t, J=1.3 Hz, 1H), 7.13 (t, J=1.3 Hz, 1H), 7.47 (dd, J=8.2, 2.2 Hz, 1H), 7.56 (brs, 1H), 7.66 (d, J=4.1 Hz, 1H), 7.71 (dd, J=8.2, 0.6 Hz, 1H), 7.76 (d, J=4.1 Hz, 1H), 8.52 (dd, J=2.2, 0.6 Hz, 1H), 9.93 (s, 1H); $^{13}$C NMR (CDCl$_3$, 125 MHz): δ$_C$ (ppm)=48.0, 119.0, 119.8, 125.5, 130.5, 131.7, 135.8, 136.7, 137.3, 144.6, 148.7, 151.4, 152.8, 183.0; MS (ESI): m/z=270.22 [M+H]$^+$.

5-Imidazol-1-ylmethyl-2,3-diphenyl-pyridine (35)

Synthesized using 2-thiophenylboronic acid (139 mg, 1.10 mmol) and 6 (150 mg, 0.55 mmol) according to Method C. Yellow solid. Yield: 102 mg, 0.37 mmol, 67%. $^1$H NMR (500 MHz, CDCl$_3$): δ$_H$ (ppm): 5.26 (s, 2H), 6.96 (t, J=1.3 Hz, 1H), 7.13 (dd, J=5.0, 3.5 Hz 1H), 7.17 (t, J=1.3 Hz, 1H), 7.42 (dd, J=3.5, 1.3 Hz, 1H), 7.46 (dd, J=5.0, 1.3 Hz, 1H), 7.64 (d, J=2.5 Hz, 1H), 8.00 (s, 1H), 8.24 (d, J=2.5 Hz, 1H); $^{13}$C NMR (CDCl$_3$, 125 MHz): δ$_C$ (ppm)=47.7, 119.1, 127.6, 127.8, 128.9, 129.0, 130.7, 136.9, 137.2, 138.2, 141.0, 146.6, 149.2; MS (ESI): m/z=276.55 [M+H]$^+$.

3-Imidazol-1-ylmethyl-2-thiophen-2-yl-pyridine (36)

Synthesized using 2-thiophenylboronic acid (161 mg, 1.26 mmol) and 5 (150 mg, 0.63 mmol) according to Method C. Yellow solid. Yield: 111 mg, 0.46 mmol, 73%. $^1$H NMR (500 MHz, CDCl$_3$): δ$_H$ (ppm): 5.39 (s, 2H), 6.88 (t, J=1.3 Hz, 1H), 7.13-7.15 (m, 2H), 7.17 (dd, J=7.9, 1.9 Hz, 1H), 7.20 (dd, J=7.9, 4.4 Hz, 1H), 7.23 (dd, J=3.8, 1.3 Hz, 1H), 7.50 (dd, J=5.0, 1.3 Hz, 1H), 7.51 (brs, 1H). 8.60 (dd, J=4.4, 1.9 Hz, 1H); $^{13}$C NMR (CDCl$_3$, 125 MHz): δ$_C$ (ppm)=48.4, 119.3, 122.5, 127.2, 127.8, 128.5, 128.6, 130.3, 136.1, 137.5, 142.7, 149.0, 150.8; MS (ESI): m/z=241.79 [M+H]$^+$.

2-Benzo[b]thiophen-2-yl-5-imidazol-1-ylmethyl-pyridine (37)

Synthesized using benzo[b]thiophen-2-ylboronic acid (149 mg, 0.84 mmol) and 1a (100 mg, 0.42 mmol) according to Method C. Yellow solid. Yield: 46 mg, 0.16 mmol, 38%. $^1$H NMR (CDCl$_3$, 500 MHz): δ$_H$ (ppm): 5.17 (s, 2H), 6.93 (t, J=1.3 Hz, 1H), 7.35-7.38 (m, 2H), 7.46 (dd, J=8.2, 2.2 Hz, 1H), 7.60 (brs, 1H), 7.79 (d, J=8.2 Hz, 1H), 7.80-7.83 (m 1H), 7.84 (d, J=0.6 Hz, 1H), 7.86-7.88 (m, 1H), 8.52 (d, J=1.9 Hz, 1H); $^{13}$C NMR (CDCl$_3$, 125 MHz): δ$_C$ (ppm)=48.1, 119.0, 119.7, 121.7, 122.6, 124.2, 123.6, 125.3, 130.4, 130.6, 135.6, 137.3, 140.3, 140.8, 143.8, 148.5, 152.8; MS (ESI): m/z=292.04 [M+H]$^+$.

2-Benzo[b]thiophen-3-yl-5-imidazol-1-ylmethyl-pyridine (38)

Synthesized using benzo[b]thiophen-3-ylboronic acid (224 mg, 1.26 mmol) and 1a (150 mg, 0.63 mmol) according to Method C. Yellow solid. Yield: 100 mg, 0.34 mmol, 54%. $^1$H NMR (500 MHz, CDCl$_3$): δ$_H$ (ppm): 5.27 (s, 2H), 6.99 (t, J=1.3 Hz, 1H), 7.18 (brs, 1H), 7.39-7.42 (m, 1H), 7.43-7.47 (m, 1H), 7.59 (dd, J=8.2, 2.5 Hz, 1H), 7.70 (dd, J=8.2, 0.9 Hz, 1H), 7.82 (s, 1H), 7.90-7.92 (m, 1H), 8.01 (s, 1H), 8.46-8.48 (m, 1H), 8.66-8.67 (m, 1H); $^{13}$C NMR (CDCl$_3$, 125 MHz): δ$_C$ (ppm)=45.5, 119.3, 122.6, 122.8, 124.1, 124.7, 124.8, 127.1, 128.7, 129.4, 135.7, 135.9, 137.0, 137.1, 140.9, 148.6, 155.0; MS (ESI): m/z=292.05 [M+H]$^+$.

2-Furan-2-yl-5-imidazol-1-ylmethyl-pyridine (39)

Synthesized using 2-furanylboronic acid (141 mg, 1.26 mmol) and 1a (150 mg, 0.63 mmol) according to Method C. Yellow solid. Yield: 127 mg, 0.56 mmol, 89%. $^1$H NMR (CDCl$_3$, 500 MHz): δ$_H$ (ppm): 5.12 (s, 2H), 6.52 (dd, J=3.4, 1.5 Hz, 1H), 6.89 (t, J=1.2 Hz, 1H), 7.05 (dd, J=3.4, 0.6 Hz, 1H). 7.09 (brs, 1H), 7.43 (dd, J=8.2, 2.1 Hz, 1H), 7.52 (dd, J=1.5, 0.6 Hz, 1H), 7.56 (s, 1H), 7.65 (d, J=8.2 Hz, 1H), 8.46 (d, J=1.8 Hz, 1H); $^{13}$C NMR (CDCl$_3$, 125 MHz): δ$_C$ (ppm)=48.1, 109.2, 112.1, 118.6, 118.9, 129.7, 130.2, 135.6, 137.2, 143.6, 148.4, 149.5, 152.9; MS (ESI): m/z=225.93 [M+H]$^+$.

2-Furan-3-yl-5-imidazol-1-ylmethyl-pyridine (40)

Synthesized using 3-furanylboronic acid (188 mg, 1.68 mmol) and 1a (200 mg, 0.84 mmol) according to Method C. Brown solid. Yield: 144 mg, 0.61 mmol, 73%. $^1$H NMR (CDCl$_3$, 500 MHz): OH (ppm): 5.13 (s, 2H), 6.87 (dd, J=1.9, 0.9 Hz, 1H), 6.90 (t, J=1.3 Hz, 1H), 7.10 (s, 1H), 7.41 (dd, J=8.2, 2.2 Hz, 1H), 7.43 (dd, J=8.2, 1.3 Hz, 1H), 7.49 (t, J=1.6 Hz, 1H), 7.56 (brs, 1H), 8.02 (dd, J=0.7 Hz, J=1.4 Hz, 1H); $^{13}$C NMR (CDCl$_3$, 125 MHz): 00 (ppm)=48.1, 108.5, 118.9, 120.1, 126.5, 129.5, 130.3, 135.6, 137.3, 141.5, 144.0, 148.6, 152.1; MS (ESI): m/z=226.15 [M+H]$^+$.

2-Benzo[b]furan-2-yl-5-imidazol-1-ylmethyl-pyridine (41)

Synthesized using benzo[b]furan-2-ylboronic acid (204 mg, 1.26 mmol) and 1a (150 mg, 0.63 mmol) according to Method C. Yellow solid. Yield: 71 mg, 0.26 mmol, 41%. $^1$H NMR (CDCl$_3$, 500 MHz): $\delta_H$ (ppm): 5.18 (s, 2H), 6.93 (s, 1H), 7.13 (s, 1H), 7.25-7.28 (m, 2H), 7.35 (dt, J=8.2, 1.2 Hz, 1H), 7.44 (d, J=0.9 Hz, 1H), 7.51 (dd, J=8.2, 2.1 Hz, 1H), 7.56 (dd, J=8.2, 0.9 Hz, 1H), 7.60 (s, 1H), 7.65 (d, J=7.3 Hz, 1H), 7.88 (d, J=8.2 Hz, 1H), 8.56 (d, J=2.1 Hz, 1H); $^{13}$C NMR (CDCl$_3$, 125 MHz): $\delta_C$ (ppm)=48.1, 105.5, 111.5, 119.0, 119.8, 121.8, 123.3, 125.5, 128.6, 130.4, 130.8, 135.7, 137.3, 148.7, 149.4, 154.3, 155.4; MS (ESI): m/z=276.03 [M+H]$^+$.

2,3-Di-furan-2-yl-5-imidazol-1-ylmethyl-pyridine (42)

Synthesized using 2-furanylboronic acid (123 mg, 1.10 mmol) and 6 (150 mg, 0.55 mmol) according to Method C. Yellow solid. Yield: 108 mg, 0.37 mmol, 67%. $^1$H NMR (500 MHz, CDCl$_3$): $\delta_H$ (ppm): 5.19 (s, 2H), 6.26 (dd, J=3.5, 0.6 Hz, 1H), 6.41 (dd, J=3.5, 0.9 Hz, 1H), 6.41-6.48 (m, 2H), 6.93 (t, J=1.3 Hz, 1H), 7.12 (bs, 1H), 7.49-7.50 (m, 2H), 7.60 (bs, 1H), 7.61 (d, J=2.2 Hz, 1H), 8.50 (d, J=2.2 Hz, 1H); $^{13}$C NMR (CDCl$_3$, 125 MHz): $\delta_C$ (ppm)=47.9, 110.0, 111.6, 111.7, 111.7, 119.0, 124.8, 130.0, 130.4, 136.0, 137.3, 142.8, 143.3, 146.8, 147.4, 149.9, 151.7; MS (ESI): m/z=292.09 [M+H]$^+$.

6-Bromonicotinaldehyde (43c)

To a suspension of 2,5-dibromopyridine (2.00 g, 8.44 mmol) in dry diethyl ether (25 mL) was added n-BuLi (3.55 mL, 8.87 mmol, 2.5 M solution in hexane) at −80° C. under a nitrogen atmosphere. After stirring for 1 h at −80° C. dry DMF (0.68 mg, 9.28 mmol) was added. After stirring for an additional hour at −80° C. the reaction mixture was allowed to warm to 0° C. and HCl (18.0 mL, 1 M) was added. After stirring for 15 minutes the phases were separated and aqueous layer was extracted twice with diethyl ether. The combined organic layers were washed with water (50 mL), brine (50 mL) and dried over MgSO$_4$. The organic phase was concentrated under reduced pressure and the crude product was purified by flash chromatography on silica-gel using a mixture of hexane/ethyl acetate (8:1) as eluent. White solid. Yield: 1.03 g, 66%. $^1$H NMR (CDCl$_3$, 500 MHz): $\delta_H$ (ppm)=7.67-7.71 ppm (m, 1H), 8.02 (dd, J=8.2, 2.5 Hz, 1H), 8.84 (dd, J=2.5, 0.6 Hz, 1H), 10.10 (s, 1H); $^{13}$C NMR (CDCl$_3$, 125 MHz): $\delta_C$ (ppm)=129.0, 130.6, 137.5, 148.3, 152.5, 189.4; MS (ESI): m/z=187.19 [M+H]$^+$.

6-Phenylnicotinaldehyde (43b)

Synthesized using compound 43c (1.20 g, 6.44 mmol) and phenylboronic acid (1.18 g, 9.65 mmol) according to Method C. Crude product was purified by flash chromatography on silica-gel using a mixture of hexane/ethyl acetate (10:1) as eluent. Light yellow solid. Yield: 1.10 g, 94%. $^1$H NMR (CDCl$_3$, 500 MHz): $\delta_H$ (ppm)=7.44-7.52 ppm (m, 3H), 7.87 (d, J=8.2 Hz, 1H), 8.04-8.08 (m, 2H), 8.20 (dd, J=8.2, 2.2 Hz, 1H), 9.10 (dd, J=2.2, 0.6 Hz, 1H), 10.11 (s, 1H); $^{13}$C NMR (CDCl$_3$, 125 MHz): $\delta_C$ (ppm)=120.5, 127.5, 129.0, 129.8, 130.4, 136.5, 138.0, 152.4, 162.2, 190.4; MS (ESI): m/z=184.31 [M+H]$^+$.

2-Methyl-1-(6-phenylpyridin-3-yl)propan-1-ol (43a)

Synthesized using compound 43b (283 mg, 1.55 mmol) and isopropylmagnesium chloride (1.55 mL, 3.10 mmol, 2 M in THF) according to Method D. Crude product was purified by flash chromatography on silica-gel using a mixture of hexane/ethyl acetate (4:1) as eluent. Orange solid. Yield: 138 mg, 40%. $^1$H NMR (CDCl$_3$, 500 MHz): $\delta_H$ (ppm)=0.82-0.93 (m, 3H), 1.02 (d, J=6.6 Hz, 3H), 1.95-2.08 (m, 1H), 4.46 (d, J=6.6 Hz, 1H), 7.39-7.44 (m, 1H), 7.45-7.50 (m, 2H), 7.68-7.75 (m, 2H), 7.96-8.01 (m, 2H), 8.57 (d, J=1.9 Hz, H); MS (ESI): m/z=228.26 [M+H]$^+$.

2-Methyl-1-(6-phenylpyridin-3-yl)propyl 1H-imidazole-1-carboxylate (43)

Synthesized using compound 43a (81 mg, 0.36 mmol), CDI (289 mg, 1.78 mmol) and acetonitrile (5 mL) according to Method E. Crude product was purified by flash chromatography on silica-gel using a mixture of hexane/ethyl acetate (4:1) as eluent. White solid. Yield: 90.0 mg, 90%. $^1$H NMR (CDCl$_3$, 500 MHz): $\delta_H$ (ppm)=0.95 (d, J=6.9 Hz, 3H), 1.14 (d, J=6.6 Hz, 3H), 2.37 (m, 1H), 5.70 (d, J=8.2 Hz, 1H), 7.09 (dd, J=1.6, 0.6 Hz, 1H), 7.40-7.51 (m, 4H), 7.72-7.79 (m, 2H), 7.98-8.03 (m, 2H), 8.19 (t, J=0.9 Hz, 1H), 8.71 (dd, J=2.2, 0.6 Hz, 1H); $^{13}$C NMR (CDCl$_3$, 125 MHz): $\delta_C$ (ppm)=18.7, 18.8, 33.6, 83.7, 117.2, 120.4, 127.1, 129.0, 129.5, 131.1, 131.8, 135.6, 137.2, 138.8, 148.7, 158.0; MS (ESI): m/z=322.32 [M+H]$^+$.

1-(6-phenylpyridin-3-yl)propan-1-ol (44a)

Synthesized using compound 43b (313 mg, 1.71 mmol) and ethylmagnesium bromide (3.42 mL, 3.42 mmol, 1 M in THF) according to Method D. Crude product was purified by flash chromatography on silica-gel using a mixture of hexane/ethyl acetate (3:1) as eluent. Light yellow solid. Yield: 298 mg, 82%. $^1$H NMR (CDCl$_3$, 500 MHz): $\delta_H$ (ppm)=0.90-0.95 (m, 3H) 1.71-1.88 (m, 2H) 4.62 (t, J=6.62 Hz, 1H) 7.38-7.43 (m, 1H) 7.43-7.49 (m, 2H) 7.64-7.67 (m, 1H) 7.69-7.73 (m, 1H) 7.92-7.96 (m, 2H) 8.54 (d, J=2.21 Hz, 1H); $^{13}$C NMR (CDCl$_3$, 125 MHz): $\delta_C$ (ppm)=9.9, 31.7, 73.2, 120.3, 126.8, 128.7, 128.8, 134.5, 138.3, 139.0, 147.7, 156.5; MS (ESI): m/z=214.28 [M+H]$^+$.

1-(6-phenylpyridin-3-yl)propyl 1H-imidazole-1-carboxylate (44)

Synthesized using compound 44a (150 mg, 0.70 mmol), CDI (570 mg, 3.52 mmol) and acetonitrile (9 mL) according to Method E. Crude product was purified by flash chromatography on silica-gel using a mixture of hexane/ethyl acetate (3:1) as eluent. White solid. Yield: 116 mg, 54%. $^1$H NMR (CDCl$_3$, 500 MHz): $\delta_H$ (ppm)=1.04 (t, J=7.4 Hz, 3H), 2.01-2.15 (m, 1H), 2.22 (dt, J=14.3, 7.2 Hz, 1H), 5.92 (t, J=7.1 Hz, 1H), 7.09 (dd, J=1.6, 0.6 Hz, 1H), 7.41-7.51 (m, 4H), 7.75-7.80 (m, 2H), 7.98-8.03 (m, 2H), 8.17-8.19 (m, 1H), 8.74-8.77 (m, 1H); $^{13}$C NMR (CDCl$_3$, 125 MHz): $\delta_C$ (ppm)=9.8, 28.7, 79.8, 117.0, 120.3, 126.9, 128.8, 129.3, 130.8, 132.3, 135.0, 137.0, 138.6, 148.0, 148.3, 158.0; MS (ESI): m/z=308.30 [M+H]$^+$.

1-(6-phenylpyridin-3-yl)ethanol (45a)

Synthesized using compound 43b (210 mg, 1.15 mmol) and methylmagnesium bromide (2.29 mL, 2.29 mmol, 1 M in THF) according to Method D. Crude product was purified by flash chromatography on silica-gel using a mixture of hexane/ethyl acetate (2:1) as eluent. Light yellow solid. Yield: 201 mg, 88%. $^1$H NMR (CDCl$_3$, 500 MHz): $\delta_H$ (ppm)=1.51 (d, J=6.6 Hz, 3H), 3.05 (br, s, 1H), 4.92 (q, J=6.6 Hz, 1H), 7.38-7.50 (m, 3H), 7.65 (d, J=7.9 Hz, 1H), 7.74 (dd, J=8.2, 2.2 Hz, 1H), 7.91-7.97 (m, 2H), 8.58 (d, J=2.2 Hz, 1H); $^{13}$C NMR (CDCl₃, 125 MHz): $\delta_C$ (ppm)=25.0, 67.8, 120.4, 126.9, 128.7, 128.9, 134.0, 139.0, 139.5, 147.2, 156.6; MS (ESI): m/z=200.32 [M+H]⁺.

1-(6-phenylpyridin-3-yl)ethyl 1H-imidazole-1-carboxylate (45)

Synthesized using compound 45a (170 mg, 0.85 mmol), CDI (692 mg, 4.27 mmol) and acetonitrile (10 mL) according to Method E. Crude product was purified by flash chromatography on silica-gel using a mixture of hexane/ethyl acetate (2:1) as eluent. White solid. Yield: 107 mg, 43%. ¹H NMR (CDCl₃, 500 MHz): $\delta_H$ (ppm)=1.82 (d, J=6.9 Hz, 3H), 6.16 (q, J=6.6 Hz, 1H), 7.08 (dd, J=1.7, 0.8 Hz, 1H), 7.41-7.53 (m, 4H), 7.76-7.85 (m, 2H), 7.98-8.03 (m, 2H), 8.17 (d, J=1.3 Hz, 1H), 8.78 (d, J=1.9 Hz, 1H); ¹³C NMR (CDCl₃, 125 MHz): $\delta_C$ (ppm)=21.5, 74.9, 117.1, 120.4, 126.9, 128.8, 129.3, 130.8, 133.3, 134.7, 137.0, 138.6, 147.9, 148.0, 158.0; MS (ESI): m/z=294.28 [M+H]⁺.

Cyclopropyl(6-phenylpyridin-3-yl)methanol (46a)

Synthesized using compound 43b (227 mg, 1.24 mmol) and cyclopropylmagnesium bromide (4.96 mL, 2.48 mmol, 0.5 M in THF) according to Method D. Crude product was purified by flash chromatography on silica-gel using a mixture of hexane/ethyl acetate (3:1) as eluent. Light yellow solid. Yield: 234 mg, 84%. ¹H NMR (CDCl₃, 500 MHz): $\delta_H$ (ppm)=0.35-0.44 (m, 1H), 0.49 (dq, J=9.4, 4.7 Hz, 1H), 0.55-0.68 (m, 2H), 1.21 (qt, J=8.1, 5.0 Hz, 1H), 3.00 (br, s, 1H), 4.05 (d, J=8.2 Hz, 1H), 7.38-7.44 (m, 1H), 7.44-7.50 (m, 2H), 7.66-7.70 (m, 1H), 7.80-7.85 (m, 1H), 7.94-8.00 (m, 2H), 8.64-8.69 (m, 1H); ¹³C NMR (CDCl₃, 125 MHz): $\delta_C$ (ppm)=-2.8, 3.6, 19.0, 75.9, 120.3, 126.8, 128.7, 128.8, 134.5, 137.7, 139.1, 147.6, 156.5; MS (ESI): m/z=226.28 [M+H]⁺.

5-(Cyclopropyl(1H-imidazol-1-yl)methyl)-2-phenylpyridine (46)

Synthesized using compound 46a (200 mg, 0.89 mmol), CDI (720 mg, 4.44 mmol) and acetonitrile (12 mL) according to Method E. Crude product was purified by flash chromatography on silica-gel using a mixture of hexane/ethyl acetate (1:3) as eluent. White solid. Yield: 45 mg, 18%. ¹H NMR (CDCl₃, 500 MHz): $\delta_H$ (ppm)=0.50-0.61 (m, 2H), 0.81-0.95 (m, 2H), 1.58 (m, 1H), 4.49 (d, J=9.5 Hz, 1H), 6.98 (t, J=1.3 Hz, 1H), 7.13 (t, J=0.9 Hz, 1H), 7.40-7.51 (m, 4H), 7.72 (dd, J=9.9, 1.4 Hz, 2H), 7.97-8.02 (m, 2H), 8.63 (d, J=2.2 Hz, 1H); ¹³C NMR (CDCl₃, 125 MHz): $\delta_C$ (ppm)=4.9, 5.2, 16.2, 63.8, 118.2, 120.4, 126.8, 128.8, 129.2, 129.7, 134.0, 134.9, 136.4, 138.5, 148.0, 157.4; MS (ESI): m/z=276.28 [M+H]⁺.

6-(Furan-3-yl)nicotinaldehyde (47b)

Synthesized using compound 43c (976 mg, 5.25 mmol) and 3-furanboronic acid (881 mg, 7.87 mmol) according to Method C. Crude product was purified by flash chromatography on silica-gel using a mixture of hexane/ethyl acetate (10:1) as eluent. White solid. Yield: 770 mg, 85%. ¹H NMR (CDCl₃, 500 MHz): $\delta_H$ (ppm)=6.94 (dd, J=1.9, 0.9 Hz, 1H), 7.51-7.55 (m, 1H), 7.58 (dd, J=8.2, 0.6 Hz, 1H), 8.11-8.17 (m, 2H), 9.00 (dd, J=2.2, 0.9 Hz, 1H), 10.06 (s, 1H); ¹³C NMR (CDCl₃, 125 MHz): $\delta_C$ (ppm)=108.5, 120.0, 126.5, 129.6, 136.3, 143.2, 144.4, 152.6, 156.8, 190.1; MS (ESI): m/z=174.26 [M+H]⁺.

1-(6-(Furan-3-yl)pyridin-3-yl)ethanol (47a)

Synthesized using compound 47a (200 mg, 1.16 mmol) and methylmagnesium bromide (2.31 mL, 2.31 mmol, 1 M in THF) according to Method D. Crude product was purified by flash chromatography on silica-gel using a mixture of hexane/ethyl acetate (2:1) as eluent. Orange oil. Yield: 141 mg, 65%. ¹H NMR (CDCl₃, 500 MHz): $\delta_H$ (ppm)=1.50 (d, J=6.6 Hz, 3H), 4.91 (q, J=6.3 Hz, 1H), 6.87 (dd, J=1.9, 0.6 Hz, 1H), 7.41 (d, J=8.2 Hz, 1H), 7.48 (t, J=1.7 Hz, 1H), 7.70 (dd, J=8.2, 2.2 Hz, 1H), 7.97-8.04 (m, 1H), 8.46 (d, J=2.2 Hz, 1H); ¹³C NMR (CDCl₃, 125 MHz): $\delta_C$ (ppm)=25.0, 67.8, 108.6, 119.9, 126.7, 133.9, 139.1, 141.1, 143.8, 147.2, 150.9; MS (ESI): m/z=190.29 [M+H]⁺.

1-(6-(Furan-3-yl)pyridine-3-yl)ethyl 1H-imidazole-1-carboxylate (47)

Synthesized using compound 47a (110 mg, 0.58 mmol), CDI (471 mg, 2.91 mmol) and acetonitrile (7 mL) according to Method E. Crude product was purified by flash chromatography on silica-gel using a mixture of hexane/ethyl acetate (3:2) as eluent. White solid. Yield: 40 mg, 24%. ¹H NMR (CDCl₃, 500 MHz): $\delta_H$ (ppm)=1.78 (d, J=6.6 Hz, 3H), 6.11 (q, J=6.7 Hz, 1H), 6.89 (dd, J=1.9, 0.9 Hz, 1H), 7.07 (dd, J=1.6, 0.6 Hz, 1H), 7.40-7.44 (m, 1H), 7.46-7.52 (m, 2H), 7.74 (dd, J=8.4, 2.7 Hz, 1H), 8.04 (dd, J=1.4, 0.8 Hz, 1H), 8.12-8.18 (m, 1H), 8.67 (d, J=2.2 Hz, 1H); ¹³C NMR (CDCl₃, 125 MHz): $\delta_C$ (ppm)=21.4, 74.9, 108.5, 117.0, 119.9, 126.5, 130.8, 132.8, 134.6, 137.0, 141.6, 144.0, 147.9, 148.0, 152.4; MS (ESI): m/z=284.25 [M+H]⁺.

1-(6-(Furan-3-yl)pyridine-3yl)propan-1-ol (48a)

Synthesized using compound 47b (194 mg, 1.12 mmol) and ethylmagnesium bromide (2.24 mL, 2.24 mmol, 1 M in THF) according to Method D. Crude product was purified by flash chromatography on silica-gel using a mixture of hexane/ethyl acetate (3:1) as eluent. Product was used directly in the next step without further characterization. White solid. Yield: 73 mg, 32%. MS (ESI): m/z=204.30 [M+H]⁺.

1-(6-(Furan-3-yl)pyridin-3-yl)ethyl 1H-imidazole-1-carboxylate (48)

Synthesized using compound 48a (73.0 mg, 0.36 mmol), CDI (291 mg, 1.80 mmol) and acetonitrile (4 mL) according to Method E. Crude product was purified by flash chromatography on silica-gel using a mixture of hexane/ethyl acetate (1:1) as eluent. Green oil. Yield: 62 mg, 67%. ¹H NMR (CDCl₃, 500 MHz): $\delta_H$ (ppm)=1.00 (t, J=7.4 Hz, 3H), 1.96-2.08 (m, 1H), 2.12-2.24 (m, 1H), 5.85 (t, J=7.1 Hz, 1H), 6.88 (dd, J=1.9, 0.6 Hz, 1H), 7.04-7.09 (m, 1H), 7.42 (t, J=1.4 Hz, 1H), 7.45-7.51 (m, 2H), 7.69 (dd, J=8.2, 2.2 Hz, 1H), 8.01-8.06 (m, 1H), 8.15 (s, 1H), 8.63 (d, J=2.2 Hz, 1H); ¹³C NMR (CDCl₃, 125 MHz): $\delta_C$ (ppm)=9.7, 28.6, 79.8, 108.5, 117.0, 119.8, 126.5, 130.7, 131.8, 134.9, 136.9, 141.5, 144.0, 148.0, 148.3, 152.3; MS (ESI): m/z=298.27 [M+H]⁺.

1-(6-(Furan-3-yl)pyridin-3-yl)-2-methylpropan-1-ol (49a)

Synthesized using compound 47b (160 mg, 0.92 mmol) and isopropylmagnesium chloride (0.92 mL, 1.85 mmol, 2 M in THF) according to Method D. Crude product was purified by flash chromatography on silica-gel using a mixture of hexane/ethyl acetate (3:1) as eluent. Yellow solid. Yield: 53 mg, 27%. MS (ESI): m/z=218.30 [M+H]⁺.

1-(6-(Furan-3-yl)pyridin-3-yl)-2-methylpropyl 1H-imidazole-1-carboxylate (49)

Synthesized using compound 49a (73.0 mg, 0.36 mmol), CDI (291 mg, 1.80 mmol) and acetonitrile (4 mL) according to Method E. Crude product was purified by flash chromatography on silica-gel using a mixture of hexane/ethyl acetate (1:1) as eluent. Green oil. Yield: 62 mg, 67%. $^1$H NMR (CDCl$_3$, 500 MHz): $\delta_H$ (ppm)=0.92 (d, J=6.9 Hz, 3H), 1.11 (d, J=6.3 Hz, 3H), 2.25-2.44 (m, 1H), 5.63 (d, J=7.9 Hz, 1H), 6.88 (s, 1H), 7.08 (s, 1H), 7.41-7.58 (m, 3H), 7.66 (dd, J=7.9, 1.9 Hz, 1H), 8.03 (s, 1H), 8.16 (s, 1H), 8.60 (s, 1H); $^{13}$C NMR (CDCl$_3$, 125 MHz): $\delta_C$ (ppm)=18.6, 18.8, 33.5, 83.8, 108.7, 117.2, 120.0, 126.8, 131.1, 131.4, 135.4, 137.2, 141.7, 144.2, 148.2, 148.8, 152.5; MS (ESI): m/z=312.32 [M+H]$^+$.

Cyclopropyl(6-(furan-3-yl)pyridin-3-yl)methanol (50a)

Synthesized using compound 47b (168 mg, 0.97 mmol) and cyclopropylmagnesium bromide (3.88 mL, 1.94 mmol, 0.5 M in THF) according to Method D. Crude product was purified by flash chromatography on silica-gel using a mixture of hexane/ethyl acetate (3:1) as eluent. Yellow oil. Yield: 140 mg, 67%. $^1$H NMR (CDCl$_3$, 500 MHz): $\delta_H$ (ppm)=0.35-0.44 (m, 1H), 0.49 (td, J=9.6, 5.0 Hz, 1H), 0.55-0.70 (m, 2H), 1.16-1.25 (m, 1H), 2.71 (br, s, 1H), 4.04 (d, J=8.2 Hz, 1H), 6.89 (dd, J=1.9, 0.6 Hz, 1H), 7.44 (dd, J=8.0, 0.8 Hz, 1H), 7.48-7.50 (m, 1H), 7.75-7.79 (m, 1H), 8.02 (dd, J=1.4, 0.8 Hz, 1H), 8.56 (dd, J=2.2, 0.6 Hz, 1H); $^{13}$C NMR (CDCl$_3$, 125 MHz): $\delta_C$ (ppm)=2.8, 3.6, 19.1, 76.0, 108.6, 119.8, 126.8, 134.4, 137.3, 141.1, 143.8, 147.6, 150.9; MS (ESI): m/z=216.27 [M+H]$^+$.

5-(Cyclopropyl(1H-imidazol-1-yl)methyl)-2-(furan-3-yl)pyridine (50)

Synthesized using compound 50a (67.0 mg, 0.31 mmol), CDI (253 mg, 1.56 mmol) and NMP (5 mL) according to Method E. Crude product was purified by flash chromatography on silica-gel using a mixture of ethyl acetate/methanol (9:1) as eluent. Brown oil. Yield: 20 mg, 24%. $^1$H NMR (CDCl$_3$, 500 MHz): $\delta_H$ (ppm)=0.47-0.57 (m, 2H), 0.81-0.90 (m, 2H), 1.65-1.72 (m, 1H), 4.45 (d, J=9.1 Hz, 1H), 6.88 (dd, J=1.9, 0.9 Hz, 1H), 6.95 (t, J=1.3 Hz, 1H), 7.11 (t, J=1.1 Hz, 1H), 7.39-7.45 (m, 2H), 7.49 (t, J=1.7 Hz, 1H), 7.71 (s, 1H), 8.02 (dd, J=1.6, 0.9 Hz, 1H), 8.53 (dd, J=1.4, 0.8 Hz, 1H); $^{13}$C NMR (CDCl$_3$, 125 MHz): $\delta_C$ (ppm)=4.8, 5.2, 16.2, 63.8, 108.5, 118.1, 120.0, 126.5, 129.7, 133.6, 134.7, 136.4, 141.4, 144.0, 148.0, 151.9; MS (ESI): m/z=266.27 [M+H]$^+$.

5-(1-(1H-imidazol-1-yl)ethyl)-2-phenylpyridine (51)

Synthesized using compound 45a (164 mg, 0.82 mmol), CDI (667 mg, 4.12 mmol) and NMP (8 mL) according to Method E. Crude product was purified by flash chromatography on silica-gel using a mixture of ethyl acetate/methanol (9:1) as eluent. Brown oil. Yield: 20 mg, 10%. $^1$H NMR (CDCl$_3$, 500 MHz): $\delta_H$ (ppm)=1.93 (d, J=7.3 Hz, 3H), 5.45 (q, J=6.9 Hz, 1H), 6.97 (t, J=1.4 Hz, 1H), 7.11-7.15 (m, 1H), 7.40-7.51 (m, 4H), 7.64 (s, 1H), 7.71 (dd, J=8.2, 0.6 Hz, 1H), 7.95-8.00 (m, 2H), 8.58 (dd, J=1.6, 0.6 Hz, 1H); $^{13}$C NMR (CDCl$_3$, 125 MHz): $\delta_C$ (ppm)=21.8, 54.2, 117.7, 120.5, 126.9, 128.8, 129.3, 129.9, 134.3, 135.3, 135.9, 138.5, 147.5, 157.4. MS (ESI): m/z=250.26 [M+H]$^+$.

5-(1-(1H-imidazol-1-yl)propyl)-2-phenylpyridine (52)

Synthesized using compound 44a (275 mg, 1.29 mmol), CDI (1.05 g, 6.45 mmol) and NMP (10 mL) according to Method E. Crude product was purified by flash chromatography on silica-gel using a mixture of ethyl acetate/methanol (9:1) as eluent. Beige solid. Yield: 114 mg, 34%. $^1$H NMR (CDCl$_3$, 500 MHz): $\delta_H$ (ppm)=0.76 (t, J=7.3 Hz, 3H), 1.98-2.13 (m, 2H), 4.87 (t, J=7.7 Hz, 1H), 6.75 (t, J=1.1 Hz, 1H), 6.89 (s, 1H), 7.16-7.33 (m, 4H), 7.41 (s, 1H), 7.47 (d, J=8.2 Hz, 1H), 7.71-7.79 (m, 2H), 8.37 (d, J=2.2 Hz, 1H); $^{13}$C NMR (CDCl$_3$, 125 MHz): $\delta_C$ (ppm)=10.9, 28.4, 60.8, 117.4, 120.4, 126.8, 128.8, 129.2, 130.0, 134.1, 134.7, 136.3, 138.5, 148.0, 157.4; MS (ESI): m/z=264.37 [M+H]$^+$.

5-(1-(1H-imidazol-1-yl)-2-methylpropyl)-2-phenylpyridine (53)

Synthesized using compound 43a (231 mg, 1.02 mmol), CDI (825 mg, 5.09 mmol) and NMP (10 mL) according to Method E. Crude product was purified by flash chromatography on silica-gel using a mixture of ethyl acetate/methanol (9:1) as eluent. Beige solid. Yield: 71 mg, 25%. $^1$H NMR (CDCl$_3$, 500 MHz): $\delta_H$ (ppm)=0.93-1.02 (m, 6H), 2.59-2.66 (m, 1H), 4.72 (d, J=10.4 Hz, 1H), 7.02-7.07 (m, 1H), 7.09 (s, 1H), 7.40-7.51 (m, 3H), 7.62-7.70 (m, 2H), 7.70-7.76 (m, 1H), 7.95-8.02 (m, 2H), 8.67 (d, J=2.2 Hz, 1H); $^{13}$C NMR (CDCl$_3$, 125 MHz): $\delta_C$ (ppm)=19.9, 20.2, 32.4, 66.6, 117.2, 120.5, 126.8, 128.8, 129.3, 130.0, 133.2, 135.3, 136.4, 138.5, 148.8, 157.4; MS (ESI): m/z=278.41 [M+H]$^+$.

6-(naphthalen-1-yl)nicotinaldehyde (54b)

Synthesized using compound 43c (720 mg, 3.87 mmol) and 1-naphthaleneboronic acid (1.00 g, 5.81 mmol) according to Method C. Crude product was purified by flash chromatography on silica-gel using a mixture of hexane/ethyl acetate (8:1) as eluent. Orange solid. Yield: 733 mg, 81%. $^1$H NMR (CDCl$_3$, 500 MHz): $\delta_H$ (ppm)=7.50-7.62 (m, 3H), 7.65-7.69 (m, 1H), 7.77-7.81 (m, 1H), 7.92-8.00 (m, 2H), 8.10-8.14 (m, 1H), 8.31 (dd, J=7.9, 2.2 Hz, 1H), 9.25 (dd, J=2.2, 0.9 Hz, 1H), 10.22 (s, 1H); $^{13}$C NMR (CDCl$_3$, 125 MHz): $\delta_C$ (ppm)=125.1, 125.2, 125.4, 126.2, 127.0, 128.0, 128.5, 129.7, 130.0, 130.7, 134.0, 136.1, 137.2, 152.1, 164.6, 190.5; MS (ESI): m/z=234.29 [M+H]$^+$.

Cyclopropyl(6-(naphthalen-1-yl)pyridin-3-yl)methanol (54a)

Synthesized using compound 54b (253 mg, 1.09 mmol) and cyclopropylmagnesium bromide (4.34 mL, 2.17 mmol, 0.5 M in THF) according to Method D. Crude product was purified by flash chromatography on silica-gel using a mixture of hexane/ethyl acetate (3:1) as eluent. Light yellow solid. Yield: 239 mg, 80%. $^1$H NMR (CDCl$_3$, 500 MHz): $\delta_H$ (ppm)=0.39-0.54 (m, 2H), 0.60-0.72 (m, 2H), 1.22-1.29 (m, 1H), 4.04-4.14 (m, 1H), 7.42-7.60 (m, 5H), 7.86-7.92 (m, 3H), 8.04-8.08 (m, 1H), 8.77 (d, J=2.2 Hz, 1H); $^{13}$C NMR (CDCl$_3$, 125 MHz): $\delta_C$ (ppm)=3.3, 3.9, 14.4, 60.6, 125.0, 125.5, 125.9, 126.1, 126.7, 127.7, 128.6, 129.1, 134.2, 137.8, 138.5, 147.8, 158.5, 171.4; MS (ESI): m/z=276.34 [M+H]$^+$.

5-(Cyclopropyl(1H-imidazol-1-yl)methyl)-2-(naphthalen-1-yl)pyridine (54)

Synthesized using compound 54a (210 mg, 0.76 mmol), CDI (619 mg, 3.82 mmol) and NMP (8 mL) according to Method E. Crude product was purified by flash chromatography on silica-gel using a mixture of ethyl acetate/methanol (9:1) as eluent. After flash chromatography the obtained solid was recrystallized in ethyl acetate/hexane (1:1). White solid. Yield: 38 mg, 15%. $^1$H NMR (CDCl$_3$, 500 MHz):

δ$_H$ (ppm)=0.54-0.66 (m, 2H), 0.86-0.98 (m, 2H), 1.61-1.68 (m, 1H), 4.54 (d, J=9.5 Hz, 1H), 7.06 (s, 1H), 7.17 (s, 1H), 7.46-7.64 (m, 6H), 7.78 (s, 1H), 7.89-7.97 (m, 2H), 8.06-8.12 (m, 1H), 8.75 (dd, J=1.3, 0.6 Hz, 1H); $^{13}$C NMR (CDCl$_3$, 125 MHz): δ$_C$ (ppm)=5.1, 5.2, 16.4, 64.0, 118.2, 125.0, 125.2, 125.4, 125.9, 126.6, 127.6, 128.4, 129.2, 129.8, 131.0, 133.9, 134.1, 134.5, 136.4, 137.7, 147.8, 159.3; (ESI): m/z=325.96 [M+H]$^+$.

1-(6-(naphthalen-1-yl)pyridin-3-yl)ethanol (55a)

Synthesized using compound 54b (231 mg, 0.99 mmol) and methylmagnesium bromide (1.98 mL, 1.98 mmol, 1 M in THF) according to Method D. Crude product was purified by flash chromatography on silica-gel using a mixture of hexane/ethyl acetate (2:1) as eluent. White solid. Yield: 172 mg, 70%. $^1$H NMR (CDCl$_3$, 500 MHz): δ$_H$ (ppm)=1.59 (d, J=6.1 Hz, 3H), 5.00 (m, 1H), 7.44-7.62 (m, 5H), 7.80-7.86 (m, 1H), 7.90-7.96 (m, 2H), 8.07 (d, J=7.9 Hz, 1H), 8.74 (s, 1H); (ESI): m/z=250.29 [M+H]$^+$.

5-(1-(1H-imidazol-1-yl)ethyl)-2-(naphthalen-1-yl)pyridine (55)

Synthesized using compound 55a (147 mg, 0.59 mmol), CDI (478 mg, 2.95 mmol) and NMP (6 mL) according to Method E. Crude product was purified by flash chromatography on silica-gel using ethyl acetate as eluent. Beige solid. Yield: 59 mg, 33%. $^1$H NMR (CDCl$_3$, 500 MHz): δ$_H$ (ppm)=1.97 (d, J=7.3 Hz, 3H), 5.50 (q, J=6.9 Hz, 1H), 7.02-7.06 (m, 1H), 7.16 (s, 1H), 7.45-7.63 (m, 6H), 7.69 (s, 1H), 7.92 (td, J=4.9, 2.5 Hz, 2H), 8.06 (dd, J=8.2, 0.9 Hz, 1H), 8.68 (d, J=2.2 Hz, 1H); $^{13}$C NMR (CDCl$_3$, 125 MHz): δ$_C$ (ppm)=22.1, 54.5, 117.9, 125.3, 125.5, 125.6, 126.2, 126.8, 127.8, 128.6, 129.4, 130.2, 131.2, 134.1, 134.1, 135.6, 136.2, 137.9, 147.6, 159.4; (ESI): m/z=300.03 [M+H]$^+$.

6-(Thiophen-3-yl)nicotinaldehyde (56b)

Synthesized using compound 43c (840 mg, 4.52 mmol) and thiophen-3-ylboronic acid (867 g, 6.77 mmol) according to Method C. Crude product was purified by flash chromatography on silica-gel using a mixture of hexane/ethyl acetate (8:2) as eluent. Orange solid. Yield: 556 mg, 65%. $^1$H NMR (CDCl$_3$, 500 MHz): δ$_H$ (ppm)=7.45 (dd, J=5.0, 2.8 Hz, 1H), 7.72-7.80 (m, 2H), 8.11 (dd, J=2.8, 1.3 Hz, 1H), 8.19 (dd, J=8.2, 2.2 Hz, 1H), 9.06 (dd, J=2.2, 0.9 Hz, 1H), 10.11 (s, 1H); $^{13}$C NMR (CDCl$_3$, 125 MHz): δ$_C$ (ppm)=120.3, 126.3, 126.4, 126.9, 129.6, 136.5, 141.1, 152.6, 158.0, 190.2; (ESI): m/z=190.27 [M+H]$^+$.

1-(6-(Thiophen-3-yl)pyridin-3-yl)ethanol (56a)

Synthesized using compound 56b (260 mg, 1.37 mmol) and methylmagnesium bromide (2.74 mL, 2.74 mmol, 1 M in THF) according to Method D. Crude product was purified by flash chromatography on silica-gel using a mixture of hexane/ethyl acetate (1:1) as eluent. Yellow solid. Yield: 240 mg, 85%. $^1$H NMR (CDCl$_3$, 500 MHz): δ$_H$ (ppm)=1.50 (d, J=6.6 Hz, 3H), 4.90 (q, J=6.3 Hz, 1H), 7.38 (dd, J=5.0, 2.8 Hz, 1H), 7.55 (d, J=8.2 Hz, 1H), 7.61 (dd, J=5.0, 1.3 Hz, 1H), 7.70 (dd, J=8.2, 2.2 Hz, 1H), 7.85 (dd, J=2.8, 1.3 Hz, 1H), 8.48 (d, J=2.2 Hz, 1H); $^{13}$C NMR (CDCl$_3$, 125 MHz): δ$_C$ (ppm)=25.2, 68.0, 120.4, 123.6, 126.4, 126.5, 134.3, 139.5, 142.0, 147.4, 152.9; (ESI): m/z=206.29 [M+H]$^+$.

Cyclopropyl(6-(thiophen-3-yl)pyridin-3-yl)methanol (57a)

Synthesized using compound 56b (270 mg, 1.43 mmol) and cyclopropylmagnesium bromide (5.72 mL, 2.86 mmol, 0.5 M in THF) according to Method D. Crude product was purified by flash chromatography on silica-gel using a mixture of hexane/ethyl acetate (1:1) as eluent. Yellow solid. Yield: 138 mg, 42%. $^1$H NMR (CDCl$_3$, 500 MHz): δ$_H$ (ppm)=0.37-0.45 (m, 1H), 0.50 (dq, J=9.7, 4.8 Hz, 1H), 0.57-0.71 (m, 2H), 1.18-1.29 (m, 1H), 2.48 (br. s., 1H), 4.06 (d, J=8.2 Hz, 1H), 7.39 (dd, J=5.0, 3.2 Hz, 1H), 7.60 (dd, J=8.2, 0.6 Hz, 1H), 7.64-7.68 (m, 1H), 7.78-7.85 (m, 1H), 7.89 (dd, J=3.0, 1.4 Hz, 1H), 8.60-8.64 (m, 1H); $^{13}$C NMR (CDCl$_3$, 125 MHz): δ$_C$ (ppm)=2.8, 3.6, 19.1, 76.1, 120.0, 123.4, 126.2, 126.3, 134.5, 137.2, 141.9, 147.6, 152.8; (ESI): m/z=232.26 [M+H]$^+$.

5-(1-(1H-imidazol-1-yl)ethyl)-2-(thiophen-3-yl)pyridine (56)

Synthesized using compound 56a (227 mg, 1.11 mmol), CDI (897.0 mg, 5.53 mmol) and NMP (8 mL) according to Method E. Crude product was purified by flash chromatography on silica-gel using ethyl acetate/methanol (9:1) as eluent. Beige solid. Yield: 78 mg, 28%. $^1$H NMR (CDCl$_3$, 500 MHz): δ$_H$ (ppm)=1.75 (d, J=6.9 Hz, 3H), 5.25 (q, J=7.0 Hz, 1H), 6.79 (t, J=1.3 Hz, 1H), 6.96 (t, J=0.9 Hz, 1H), 7.21-7.28 (m, 2H), 7.40-7.52 (m, 3H), 7.74 (dd, J=2.8, 1.3 Hz, 1H), 8.34 (d, J=2.5 Hz, 1H); $^{13}$C NMR (CDCl$_3$, 125 MHz): δ$_C$ (ppm)=21.7, 54.2, 117.6, 120.2, 123.9, 126.1, 126.5, 129.9, 134.3, 134.9, 135.9, 141.4, 147.5, 153.5; (ESI): m/z=256.08 [M+H]$^+$.

5-(Cyclopropyl(1H-imidazol-1-yl)methyl)-2-(thiophen-3-yl)pyridine (57)

Synthesized using compound 57a (116 mg, 0.50 mmol), CDI (407 mg, 2.51 mmol) and NMP (5 mL) according to Method E. Crude product was purified by flash chromatography on silica-gel using ethyl acetate as eluent. Beige solid. Yield: 70 mg, 50%. $^1$H NMR (CDCl$_3$, 500 MHz): δ$_H$ (ppm)=0.49-0.60 (m, 2H), 0.83-0.91 (m, 2H), 1.53-1.64 (m, 1H), 4.47 (d, J=9.5 Hz, 1H), 6.97 (t, J=1.3 Hz, 1H), 7.12 (t, J=1.1 Hz, 1H), 7.39-7.46 (m, 2H), 7.59-7.63 (m, 1H), 7.64-7.68 (m, 1H), 7.72 (s, 1H), 7.91 (dd, J=3.2, 1.3 Hz, 1H), 8.56 (dd, J=1.6, 0.6 Hz, 1H); $^{13}$C NMR (CDCl$_3$, 125 MHz): δ$_C$ (ppm)=4.9, 5.2, 16.2, 63.8, 118.2, 120.2, 123.9, 126.1, 126.5, 129.8, 133.7, 134.9, 136.4, 141.4, 148.0, 153.5; (ESI): m/z=282.30 [M+H]$^+$.

Phenyl(6-phenylpyridin-3-yl)methanol (58a)

Synthesized using compound 43b (300 mg, 1.73 mmol) and phenylmagnesium bromide (1.73 mL, 3.46 mmol, 2 M in THF) according to Method D. Crude product was purified by flash chromatography on silica-gel using a mixture of hexane/ethyl acetate (3:1) as eluent. Yellow solid. Yield: 138 mg, 42%. $^1$H NMR (CDCl$_3$, 500 MHz): δ$_H$ (ppm)=5.91 (s, 1H), 7.29-7.34 (m, 1H), 7.35-7.50 (m, 7H), 7.68 (dd, J=8.2, 0.6 Hz, 1H), 7.73-7.78 (m, 1H), 7.94-7.99 (m, 2H), 8.68 (dd, J=1.6, 0.6 Hz, 1H); $^{13}$C NMR (CDCl$_3$, 125 MHz): δ$_C$ (ppm)=74.1, 120.3, 126.5, 126.9, 128.0, 128.7, 128.7, 128.9, 135.0, 137.6, 139.0, 143.0, 148.2, 156.7; (ESI): m/z=261.97 [M+H]$^+$.

5-((1H-imidazol-1-yl)(phenyl)methyl)-2-phenylpyridine (58)

Synthesized using compound 58a (299 mg, 1.14 mmol), CDI (928 mg, 5.72 mmol) and NMP (8 mL) according to Method E. Crude product was purified by flash chromatography on silica-gel using ethyl acetate as eluent. Beige solid. Yield: 75 mg, 21%. $^1$H NMR (CDCl$_3$, 500 MHz): $\delta_H$(ppm)=6.58 (s, 1H), 6.87-6.91 (m, 1H), 7.11-7.19 (m, 3H), 7.34-7.54 (m, 8H), 7.73 (d, J=8.2 Hz, 1H), 7.98-8.04 (m, 2H), 8.49 (d, J=2.5 Hz, 1H); $^{13}$C NMR (CDCl$_3$, 125 MHz): $\delta_C$ (ppm)=62.6, 119.0, 120.2, 126.8, 127.8, 128.7, 128.8, 129.0, 129.3, 129.8, 133.1, 136.1, 137.2, 138.0, 138.3, 149.2, 157.4; (ESI): m/z=312.01 [M+H]$^+$.

Methyl 6-phenylnicotinate (59a)

To a solution of 43b (350 mg, 1.91 mmol) in acetonitrile (20 mL) were added NIS (1.29 g, 5.73 mmol), K$_2$CO$_3$ (787 mg, 5.73 mmol) and CH$_3$OH (0.39 mL, 9.55 mmol). After stirring the reaction mixture for 15 h aqueous Na$_2$S$_2$O$_3$-solution (1 g Na$_2$S$_2$O$_3$ in 10 mL water) was added. The resultant mixture was extracted with a solution of 50% ether in hexane (4×20 mL). The combined organic phases were washed with brine and solvent was removed under vacuum. The crude product was purified by flash chromatography on silica-gel using a mixture of hexane/ethyl acetate (6:1) as eluent. White solid. Yield: 297 mg, 73%. $^1$H NMR (CDCl$_3$, 500 MHz): $\delta_H$ (ppm)=3.75 (s, 3H), 7.22-7.30 (m, 3H), 7.59 (dd, J=8.5, 0.9 Hz, 1H), 7.82-7.86 (m, 2H), 8.12 (dd, J=8.5, 2.2 Hz, 1H), 9.06 (dd, J=2.2, 0.9 Hz, 1H); $^{13}$C NMR (CDCl$_3$, 125 MHz): $\delta_C$ (ppm)=52.3, 119.8, 124.2, 127.3, 128.9, 129.9, 137.8, 138.3, 150.9, 160.9, 165.9; (ESI): m/z=214.02 [M+H]$^+$.

2-(6-Phenylpyridin-3-yl)propan-2-ol (59)

Synthesized using compound 59a (240 mg, 1.13 mmol) and methylmagnesium bromide (3.38 mL, 3.38 mmol, 1 M in THF) according to Method D. Purification by flash chromatography was not necessary. White solid. Yield: 193 mg, 80%. $^1$H NMR (CDCl$_3$, 500 MHz): $\delta_H$ (ppm)=1.65 (s, 6H), 7.39-7.45 (m, 1H), 7.45-7.51 (m, 2H), 7.70 (dd, J=8.2, 0.9 Hz, 1H), 7.89 (dd, J=8.2, 2.5 Hz, 1H), 7.97-8.02 (m, 2H), 8.81 (dd, J=2.5, 0.6 Hz, 1H); $^{13}$C NMR (CDCl$_3$, 125 MHz): $\delta_C$ (ppm)=31.7, 71.4, 119.9, 126.8, 128.7, 128.8, 133.2, 139.1, 142.5, 146.4, 155.9; (ESI): m/z=214.08 [M+H]$^+$.

Furan-2-yl(6-phenylpyridin-3-yl)methanol (60a)

Synthesized using compound 43b (650 mg, 3.75 mmol) and furan-2-ylmagnesium bromide (1.85 g, 10.8 mmol, 2 M in THF) according to Method D. Crude product was purified by flash chromatography on silica-gel using a mixture of hexane/ethyl acetate (6:1) as eluent. Yellow solid. Yield: 631 mg, 67%. $^1$H NMR (CDCl$_3$, 500 MHz): $\delta_H$(ppm)=3.62 (br. s., 1H), 5.86 (s, 1H), 6.17 (d, J=3.4 Hz, 1H), 6.33 (dd, J=3.0, 1.8 Hz, 1H), 7.33-7.51 (m, 4H), 7.69 (d, J=7.9 Hz, 1H), 7.83 (dd, J=8.2, 1.8 Hz, 1H), 7.88-7.99 (m, 2H); $^{13}$C NMR (CDCl$_3$, 125 MHz): $\delta_C$ (ppm)=66.7, 106.7, 109.3, 119.4, 126.0, 127.7, 128.0, 134.0, 134.3, 137.9, 141.8, 147.1, 154.1, 156.1; (ESI): m/z=251.87 [M+H]$^+$.

5-(Furan-2-yl(1H-imidazol-1-yl)methyl)-2-phenylpyridine (60)

Synthesized using compound 60a (631 mg, 2.51 mmol), CDI (2.04 g, 12.56 mmol) and NMP (4 mL) according to Method E. Crude product was purified by flash chromatography on silica-gel using ethyl acetate/methanol (9:1) as eluent. Brown Oil. Yield: 276 mg, 37%. $^1$H NMR (CDCl$_3$, 500 MHz): $\delta_H$ (ppm)=6.25-6.29 (m, 1H), 6.42 (dd, J=3.5, 1.9 Hz, 1H), 6.55 (s, 1H), 6.95 (t, J=1.3 Hz, 1H), 7.14 (t, J=1.1 Hz, 1H), 7.42-7.57 (m, 6H), 7.75 (dd, J=8.5, 0.6 Hz, 1H), 7.97-8.04 (m, 2H), 8.54 (dt, J=1.6, 0.8 Hz, 1H); $^{13}$C NMR (CDCl$_3$, 125 MHz): $\delta_C$ (ppm)=56.6, 110.7, 110.8, 118.6, 120.4, 126.9, 128.8, 129.4, 129.9, 131.6, 135.4, 136.8, 138.4, 143.9, 148.4, 150.1, 157.8; (ESI): m/z=301.96 [M+H]$^+$.

5-Methyl-2-phenylpyridine (61b)

Synthesized using 2-bromo-5-methyl-pyridine (2.92 g, 16.95 mmol) and phenylboronic acid (3.09 g, 25.4 mmol) according to Method C. Crude product was purified by flash chromatography on silica-gel using a mixture of hexane/ethyl acetate (8:1) as eluent. White solid. Yield: 1.99 g, 70%. $^1$H NMR (CDCl$_3$, 500 MHz): $\delta_H$ (ppm)=2.38 (s, 3H), 7.37-7.43 (m, 1H), 7.44-7.51 (m, 2H), 7.54-7.60 (m, 1H), 7.60-7.67 (m, 1H), 7.95-8.00 (m, 2H), 8.51-8.55 (m, 1H); $^{13}$C NMR (CDCl$_3$, 125 MHz): $\delta_C$ (ppm)=18.1, 120.0, 126.7, 128.6, 128.7, 131.5, 137.3, 139.4, 150.1, 154.8; (ESI): m/z=169.97 [M+H]$^+$.

5-(Bromomethyl)-2-phenylpyridine (61a)

Synthesized using compound 61b (760 mg, 4.49 mmol), NBS (878 mg, 4.93 mmol) and DBPO (54 mg, 0.23 mmol) in carbon tetrachloride according to Method A. Crude product was purified by flash chromatography on silica-gel using hexane/ethyl acetate (8:1) as eluent. White solid. Yield: 297 mg, 73%. $^1$H NMR (CDCl$_3$, 500 MHz): $\delta_H$ (ppm)=4.54 (s, 2H), 7.42-7.53 (m, 3H), 7.71-7.77 (m, 1H), 7.80-7.85 (m, 1H), 7.98-8.04 (m, 2H), 8.72-8.76 (m, 1H); $^{13}$C NMR (CDCl$_3$, 125 MHz): $\delta_C$ (ppm)=29.7, 120.6, 127.0, 128.4, 128.8, 130.1, 137.6, 138.5, 149.6, 157.36; (ESI): m/z=249.66 [M+H]$^+$.

2-Phenyl-5-(pyridin-4-ylmethyl)pyridine (61)

Synthesized using compound 61a (355 mg, 1.43 mmol) and 4-pyridineboronic acid (264 mg, 2.15 mmol) according to Method C. Crude product was purified by flash chromatography on silica-gel using a mixture of hexane/ethyl acetate (2:1) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Beige solid. Yield: 140 mg, 40%. $^1$H NMR (CDCl$_3$, 500 MHz): $\delta_H$ (ppm)=3.77 (s, 2H), 6.88-6.93 (m, 2H), 7.15-7.21 (m, 1H), 7.21-7.31 (m, 3H), 7.45 (dd, J=8.2, 0.9 Hz, 1H), 7.72-7.78 (m, 2H), 8.28-8.33 (m, 2H), 8.33-8.37 (m, 1H); $^{13}$C NMR (CDCl$_3$, 125 MHz): $\delta_C$ (ppm)=38.0, 120.3, 124.0, 126.7, 128.7, 128.9, 132.7, 137.1, 138.9, 148.7, 149.9, 150.0, 156.0; (ESI): m/z=246.85 [M+H]$^+$.

2-Phenyl-5-(pyridin-3-ylmethyl)pyridine (62)

Synthesized using compound 61a (100 mg, 0.40 mmol) and 3-pyridineboronic acid (74 mg, 0.61 mmol) according to Method C. Crude product was purified by flash chromatography on silica-gel using a mixture of hexane/ethyl acetate (2:1) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Beige solid. Yield: 32 mg, 32%. $^1$H NMR (CDCl$_3$, 500 MHz): δ$_H$ (ppm)=3.80 (s, 2H), 6.99-7.06 (m, 1H), 7.15-7.20 (m, 1H), 7.21-7.35 (m, 4H), 7.45 (d, J=8.2 Hz, 1H), 7.72-7.77 (m, 2H), 8.28 (dd, J=4.7, 1.3 Hz, 1H), 8.36 (d, J=1.9 Hz, 1H), 8.33 (d, J=1.9 Hz, 1H); $^{13}$C NMR (CDCl$_3$, 125 MHz): δ$_C$ (ppm)=35.9, 120.4, 123.6, 126.8, 128.7, 128.9, 133.6, 135.4, 136.2, 137.0, 139.0, 148.1, 149.9, 150.1, 155.9; (ESI): m/z=246.98 [M+H]$^+$.

4-((6-Phenylpyridin-3-yl)methyl)isoquinoline (63)

Synthesized using compound 61a (109 mg, 0.44 mmol) and isoquinolin-4-ylboronic acid (114 mg, 0.66 mmol) according to Method C. Crude product was purified by flash chromatography on silica-gel using a mixture of hexane/ethyl acetate (3:1) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Beige solid. Yield: 20 mg, 19%. $^1$H NMR (CDCl$_3$, 500 MHz): δ$_H$ (ppm)=4.43 (s, 2H), 7.37-7.54 (m, 4H), 7.59-7.65 (m, 2H), 7.65-7.75 (m, 1H), 7.89-8.07 (m, 4H), 8.48 (s, 1H), 8.65-8.70 (m, 1H), 9.23 (s, 1H); $^{13}$C NMR (CDCl$_3$, 125 MHz): δ$_C$ (ppm)=33.2, 120.3, 123.1, 126.7, 127.2, 128.4, 128.6, 128.6, 128.7, 128.9, 130.7, 133.6, 134.6, 136.7, 139.0, 143.7, 149.7, 152.3, 155.7; (ESI): m/z=296.95 [M+H]$^+$.

5-Methyl-2-phenylpyrimidine (64b)

To a solution of benzamidine hydrochloride (500 mg, 3.19 mmol) and 3-ethoxy-2-methylacrylaldehyde (400 mg, 3.51 mmol) in Methanol (10 mL) was added a NaOMe-solution (30 percent in methanol) dropwise under stirring over 30 minutes. After stirring for 4 hours water (20 mL) was added and mixture was stirred for further 30 minutes at room temperature. After filtration the obtained precipitate was washed with water and dried. White solid. Yield: 220 mg, 41%. $^1$H NMR (CDCl$_3$, 500 MHz): δ$_H$ (ppm)=2.34 (s, 3H), 7.44-7.54 (m, 3H), 8.37-8.45 (m, 2H), 8.64 (d, J=0.6 Hz, 2H); $^{13}$C NMR (CDCl$_3$, 125 MHz): δ$_C$ (ppm)=15.7, 128.1, 128.5, 128.8, 130.6, 137.9, 157.6, 162.7; (ESI): m/z=170.97 [M+H]$^+$.

5-(Bromomethyl)-2-phenylpyrimidine (64a)

Synthesized using compound 64b (205 mg, 1.20 mmol), NBS (236 mg, 1.32 mmol) and DBPO (14.6 mg, 0.06 mmol) in carbon tetrachloride according to Method A. Crude product was purified by flash chromatography on silica-gel using hexane/ethyl acetate (10:1) as eluent. Product was used directly in the next step without further characterization. White solid. Yield: 89 mg, 30%. (ESI): m/z=250.68 [M+H]$^+$.

5-((1H-imidazol-1-yl)methyl-2-phenylpyrimidine (64)

Synthesized using compound 64a (70 mg, 0.28 mmol), imidazole (76 mg, 1.12 mmol) and K$_2$CO$_3$ (195 mg, 1.41 mmol) in acetonitrile according to Method B. Crude product was purified by flash chromatography on silica-gel using ethyl acetate as eluent. After flash chromatography the product was recrystallized in ethyl acetate. Light yellow solid. Yield: 62 mg, 94%. $^1$H NMR (CDCl$_3$, 500 MHz): δ$_H$ (ppm)=5.17 (s, 2H), 6.94 (t, J=1.3 Hz, 1H), 7.15 (t, J=1.1 Hz, 1H), 7.47-7.54 (m, 3H), 7.61 (s, 1H), 8.41-8.46 (m, 2H), 8.63 (s, 2H); $^{13}$C NMR (CDCl$_3$, 125 MHz): δ$_C$ (ppm)=46.0, 118.8, 127.0, 128.2, 128.7, 130.7, 131.1, 136.8, 137.2, 156.2, 164.8; (ESI): m/z=236.92 [M+H]$^+$.

3-Methyl-6-Phenylpyridazine (65b)

Synthesized using 3-chloro-6-methylpyridazine (1.00 g, 7.78 mmol) and phenylboronic acid (1.42 g, 11.67 mmol) according to Method C. Crude product was purified by flash chromatography on silica-gel using a mixture of hexane/ethyl acetate (2:1) as eluent. White solid. Yield: 1.00 g, 76%. $^1$H NMR (CDCl$_3$, 500 MHz): δ$_H$ (ppm)=2.76 (s, 3H), 7.39 (d, J=8.5 Hz, 1H), 7.46-7.55 (m, 3H), 7.76 (d, J=8.5 Hz, 1H), 8.03-8.09 (m, 2H); $^{13}$C NMR (CDCl$_3$, 125 MHz): δ$_C$ (ppm)=22.0, 123.9, 126.9, 127.2, 128.9, 129.7, 134.4, 136.4, 157.2, 158.5; (ESI): m/z=170.96 [M+H]$^+$.

3-(Bromomethyl)-6-phenylpyridazine (65a)

Synthesized using compound 65b (982 mg, 5.77 mmol), NBS (1.13 g, 6.35 mmol) and DBPO (70 mg, 0.29 mmol) in carbon tetrachloride according to Method A. Crude product was purified by flash chromatography on silica-gel using hexane/ethyl acetate (4:1) as eluent. Product was used directly in the next step without further characterization. Orange solid. Yield: 53 mg, 4%. (ESI): m/z=250.67 [M+H]$^+$.

3-((1H-imidazol-1-yl)methyl)-6-phenylpyridazine (65)

Synthesized using compound 65a (40 mg, 0.16 mmol), imidazole (44 mg, 0.64 mmol) and K$_2$CO$_3$ (111 mg, 0.80 mmol) in acetonitrile according to Method B. Crude product was purified by flash chromatography on silica-gel using ethyl acetate as eluent. After flash chromatography the solid was washed with ethyl acetate. Light orange solid. Yield: 22 mg, 58%. $^1$H NMR (CDCl$_3$, 500 MHz): δ$_H$ (ppm)=5.58 (s, 2H), 7.08 (s, 1H), 7.17-7.26 (m, 2H), 7.55-7.61 (m, 3H), 7.72 (s, 1H), 7.88 (d, J=8.8 Hz, 1H), 8.09-8.14 (m, 2H); $^{13}$C NMR (CDCl$_3$, 125 MHz): δ$_C$ (ppm)=50.9, 119.6, 125.1, 125.5, 127.4, 129.4, 130.7, 130.8, 135.8, 137.8, 157.2, 159.3; (ESI): m/z=236.91 [M+H]$^+$.

5-((6-Phenylpyridin-3-yl)methyl)pyrimidine (66)

Synthesized using compound 61a (219 mg, 0.88 mmol) and pyrimidine-5-boronic acid (164 mg, 1.32 mmol) according to Method C. Crude product was purified by flash chromatography on silica-gel using a mixture of hexane/ethyl acetate (1:1) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. White solid. Yield: 43 mg, 20%. $^1$H NMR (CDCl$_3$, 500 MHz): δ$_H$ (ppm)=4.02 (s, 2H), 7.39-7.44 (m, 1H), 7.44-7.56 (m, 3H), 7.70 (dd, J=8.2, 0.9 Hz, 1H), 7.95-8.00 (m, 2H), 8.58-8.67 (m, 3H), 9.13 (s, 1H); $^{13}$C NMR (CDCl$_3$, 125 MHz): δ$_C$ (ppm)=33.4, 120.5, 126.8, 128.8, 129.1, 132.2, 133.3, 136.9, 138.7, 149.7, 156.4, 156.9, 157.3; (ESI): m/z=247.83 [M+H]$^+$.

2-Phenyl-5-(pyridin-4-ylmethyl)pyrimidine (67)

Synthesized using compound 64a (102 mg, 0.41 mmol) and 4-pyridineboronic acid (76 mg, 0.61 mmol) according to Method C. Crude product was purified by flash chromatography on silica-gel using a mixture of hexane/ethyl acetate (1:2) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. White solid. Yield: 57 mg, 56%. $^1$H NMR (CDCl$_3$, 500 MHz): $\delta_H$ (ppm)=3.98 (s, 2H), 7.10-7.16 (m, 2H), 7.46-7.53 (m, 3H), 8.41-8.46 (m, 2H), 8.54-8.60 (m, 2H), 8.64 (s, 2H); $^{13}$C NMR (CDCl$_3$, 125 MHz): $\delta_C$ (ppm)=35.6, 123.8, 128.0, 128.5, 128.6, 129.6, 130.7, 137.1, 147.5, 150.2, 157.4, 163.4; (ESI): m/z=247.80 [M+H]$^+$.

2-Phenyl-5-(pyrimidin-5-ylmethyl)pyrimidine (68)

Synthesized using compound 64a (102 mg, 0.41 mmol) and pyrimidine-5-boronic acid (76 mg, 0.61 mmol) according to Method C. Crude product was purified by flash chromatography on silica-gel using a mixture of hexane/ethyl acetate (1:2) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. White solid. Yield: 41 mg, 40%. $^1$H NMR (CDCl$_3$, 500 MHz): $\delta_H$ (ppm)=4.00 (s, 2H), 7.46-7.55 (m, 3H), 8.39-8.47 (m, 2H), 8.63-8.71 (m, 4H), 9.15 (s, 1H); $^{13}$C NMR (CDCl$_3$, 125 MHz): $\delta_C$ (ppm)=31.1, 128.1, 128.6, 129.1, 130.9, 132.2, 137.0, 156.9, 157.2, 157.6, 163.7; (ESI): m/z=248.83 [M+H]$^+$.

2-Phenyl-5-(pyridin-3-ylmethyl)pyrimidine (69)

Synthesized using compound 64a (100 mg, 0.41 mmol) and pyridine-3-boronic acid (74 mg, 0.60 mmol) according to Method C. Crude product was purified by flash chromatography on silica-gel using a mixture of hexane/ethyl acetate (1:2) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Light orange solid. Yield: 72 mg, 71%. $^1$H NMR (CDCl$_3$, 500 MHz): $\delta_H$ (ppm)=3.76 (s, 2H), 7.00-7.05 (m, 1H), 7.23-7.29 (m, 4H), 8.16-8.22 (m, 2H), 8.27-8.36 (m, 2H), 8.40-8.43 (m, 2H); $^{13}$C NMR (CDCl$_3$, 125 MHz): $\delta_C$ (ppm)=33.5, 123.7, 128.0, 128.6, 130.5, 130.7, 134.2, 136.1, 137.2, 148.4, 150.0, 157.3, 163.3; (ESI): m/z=247.92 [M+H]$^+$.

4-((2-Phenylpyrimidin-5-yl)methyl)isoquinoline (70)

Synthesized using compound 64a (85 mg, 0.34 mmol) and isoquinolin-4-ylboronic acid (104 mg, 0.60 mmol) according to Method C. Crude product was purified by flash chromatography on silica-gel using a mixture of hexane/ethyl acetate (3:1) as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Orange solid. Yield: 68 mg, 67%. $^1$H NMR (CDCl$_3$, 500 MHz): $\delta_H$ (ppm)=4.40 (s, 2H), 7.44-7.51 (m, 3H), 7.61-7.67 (m, 1H), 7.67-7.74 (m, 1H), 7.87 (dd, J=8.4, 0.8 Hz, 1H), 8.02-8.06 (m, 1H), 8.37-8.42 (m, 2H), 8.49 (s, 1H), 8.66 (s, 2H), 9.24 (s, 1H); $^{13}$C NMR (CDCl$_3$, 125 MHz): $\delta_C$ (ppm)=30.9, 122.8, 127.4, 127.5, 127.9, 128.6, 128.6, 128.6, 130.4, 130.6, 131.0, 134.3, 137.2, 143.6, 152.7, 157.0, 163.1; (ESI): m/z=297.91 [M+H]$^+$.

2-Methyl-5-phenylpyrazine (71b)

To a stirred solution of propylenediamine (2.94 g, 0.04 mol) in ethanol was added phenylglyoxal-monohydrate (5.00 g, 0.03 mol) at 0° C. within 30 minutes. After stirring for 1.5 hours at room temperature KOH (2.10 g, 0.04 mol) was added and the reaction mixture was refluxed for 12 hours. Then the solvent was removed under vacuum and the residue was extracted with ether. The organic phases were washed with brine and dried over MgSO$_4$. Crude product was purified by flash chromatography on silica-gel using a mixture of hexane/ethyl acetate (7:3→3:7) as eluent. After flash chromatography the product was recrystallized from hexane. White solid. Yield: 780 mg, 15%. $^1$H NMR (CDCl$_3$, 500 MHz): $\delta_H$ (ppm)=2.57 (s, 3H), 7.38-7.50 (m, 3H), 7.91-7.99 (m, 2H), 8.43-8.49 (m, 1H), 8.87 (d, J=1.5 Hz, 1H); $^{13}$C NMR (CDCl$_3$, 125 MHz): $\delta_C$ (ppm)=21.2, 126.6, 128.9, 129.4, 136.5, 140.9, 143.8, 149.8, 151.9; (ESI): m/z=170.94 [M+H]$^+$.

2-(Bromomethyl)-5-phenylpyrazine (71a)

Synthesized using compound 71b (724 mg, 4.25 mmol), NBS (832 mg, 4.68 mmol) and DBPO (52 mg, 0.21 mmol) in carbon tetrachloride according to Method A. Crude product was purified by flash chromatography on silica-gel using a mixture of hexane/ethyl acetate (3:1) as eluent. Product was used directly in the next step without further characterization. Yellow solid. Yield: 571 mg, 54%. (ESI): m/z=250.80 [M+H]$^+$.

2-((1H-imidazol-1-yl)methyl)-5-phenylpyrazine (71)

Synthesized using compound 71a (100 mg, 0.40 mmol), imidazole (109 mg, 1.60 mmol) and K$_2$CO$_3$ (276 mg, 2.00 mmol) in DMF according to Method B. Crude product was purified by flash chromatography on silica-gel using ethyl acetate as eluent. Light yellow solid. Yield: 69 mg, 73%. $^1$H NMR (CDCl$_3$, 500 MHz): $\delta_H$ (ppm)=5.50 (s, 2H), 7.24 (t, J=1.3 Hz, 1H), 7.33 (t, J=1.1 Hz, 1H), 7.64-7.74 (m, 3H), 7.86 (s, 1H), 8.17-8.23 (m, 2H), 8.63 (d, J=1.3 Hz, 1H), 9.18 (d, J=1.6 Hz, 1H); $^{13}$C NMR (CDCl$_3$, 125 MHz): $\delta_C$ (ppm)=50.0, 119.2, 126.9, 129.1, 130.2, 130.3, 135.7, 137.5, 141.5, 142.3, 152.3; (ESI): m/z=236.91 [M+H]$^+$.

5-((4-Methylpyridin-3-yl)methyl)-2-phenylpyridine (72)

Synthesized using compound 61a (100 mg, 0.40 mmol) and 4-methylpyridine-3-boronic acid (83 mg, 0.61 mmol) according to Method C. Crude product was purified by flash chromatography on silica-gel using ethyl acetate as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Light yellow solid. Yield: 54 mg, 52%. $^1$H NMR (CDCl$_3$, 500 MHz): $\delta_H$ (ppm)=2.22-2.29 (m, 3H), 4.02 (s, 2H), 7.11 (d, J=5.0 Hz, 1H), 7.37-7.51 (m, 4H), 7.64 (dd, J=8.2, 0.6 Hz, 1H), 7.95-

8.01 (m, 2H), 8.38-8.46 (m, 2H), 8.52-8.57 (m, 1H); $^{13}$C NMR (CDCl$_3$, 125 MHz): $\delta_C$(ppm)=19.3, 33.8, 120.5, 125.7, 126.9, 129.0, 129.1, 133.2, 133.8, 136.8, 139.2, 146.1, 148.7, 149.9, 150.7, 155.9; (ESI): m/z=260.85 [M+H]$^+$.

5-((5-Methylpyridin-3-yl)methyl)-2-phenylpyridine (73)

Synthesized using compound 61a (70 mg, 0.28 mmol) and 5-methylpyridine-3-boronic acid (58 mg, 0.42 mmol) according to Method C. Crude product was purified by flash chromatography on silica-gel ethyl acetate as eluent. After flash chromatography the product was solved in ethyl acetate and a few drops of conc. HCl and water were added. After stirring for 30 minutes the phases were separated and water phase was neutralized with aqueous Na$_2$CO$_3$-solution (2M). After extraction with ethyl acetate and drying over MgSO$_4$ the solvent was removed under vacuum. Light yellow solid. Yield: 56 mg, 77%. $^1$H NMR (CDCl$_3$, 500 MHz): $\delta_H$(ppm)=2.30 (d, J=0.6 Hz, 3H), 3.98 (s, 2H), 7.28-7.32 (m, 1H), 7.38-7.44 (m, 1H), 7.44-7.55 (m, 3H), 7.67 (dd, J=8.0, 0.8 Hz, 1H), 7.96-8.01 (m, 2H), 8.36 (d, J=1.6 Hz, 1H), 8.33 (d, J=1.6 Hz, 1H), 8.58 (dd, J=1.6, 0.6 Hz, 1H); $^{13}$C NMR (CDCl$_3$, 125 MHz): $\delta_C$ (ppm)=18.3, 35.7, 120.4, 126.7, 128.7, 128.9, 133.1, 133.8, 134.8, 136.8, 137.0, 139.0, 147.2, 148.6, 149.8, 155.8; (ESI): m/z=260.84 [M+H]$^+$.

The invention claimed is:

1. A compound that selectively inhibits CYP11B1, wherein the compound
   is a compound comprising pyridine and het groups of formula (2):

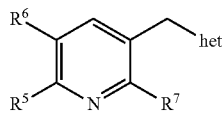

(2)

wherein the pyridine group is bonded to a carbon in Het and wherein,

Het is imidazolyl, pyridyl, isoxazolyl, or isothiazolyl, wherein Het is substituted with, C$_6$-C$_{13}$ aryl, and wherein C$_6$-C$_{13}$ aryl can optionally be substituted with R$^3$, wherein where multiple substitution with R$^3$ is possible, the substituents can be independently selected from R$^3$, R$^3$ is C$_1$-C$_{12}$ alkyl, haloalkyl, C$_1$-C$_5$ alkoxy, hydroxy, C$_6$-C$_{13}$ aryl, halogen, amino, amido, ester, ether, C(O)R$^4$, OC(O)R$^4$, SO$_2$R$^4$, SO$_2$NHR$^4$, CN, NO$_2$ or OAc, R$^4$ is H, OH, C$_1$-C$_5$ alkoxy, alkyl or aryl, R$^5$ is H, R$^6$ is H, C$_1$-C$_{12}$ alkyl, haloalkyl, cycloalkyl, C$_1$-C$_5$ alkoxy, hydroxy, halogen, alkenyl, cycloalkylene, alkynyl, naphthyl, furanyl, thiophen, benzo[b]thiophen, CN, NO$_2$, OAc, amino, amido, C(O)R$^4$, OC(O)R$^4$, trityl; which may be unsubstituted or substituted further with R$^3$, wherein where multiple substitution with R$^3$ occurs, the substituents are independently selected from R$^3$, R$^7$ is H or a pharmaceutically acceptable derivative.

2. A composition comprising a compound according to claim 1 and a pharmaceutically acceptable carrier.

3. The compound according to claim 1 wherein R$^6$ is C$_1$-C$_{12}$ alkyl, C$_1$-C$_5$ alkoxy, or hydroxy.

4. The compound according to claim 3 wherein R$^6$ is OMe or OEt.

5. The compound according to claim 3 wherein R$^6$ is methyl or ethyl.

6. The compound according to claim 3 wherein R$^6$ is hydroxy.

7. The compound according to claim 1 wherein R$^3$ is unsubstituted phenyl.

* * * * *